(12) United States Patent
Pinto

(10) Patent No.: US 7,713,982 B2
(45) Date of Patent: May 11, 2010

(54) XANTHINES WITH HM74A RECEPTOR ACTIVITY

(75) Inventor: Ivan Leo Pinto, Stevenage (GB)

(73) Assignee: Smithkline Beecham Corporation, King of Prussia, PA (US)

( * ) Notice: Subject to any disclaimer, the term of this patent is extended or adjusted under 35 U.S.C. 154(b) by 459 days.

(21) Appl. No.: 10/589,474

(22) PCT Filed: Feb. 10, 2005

(86) PCT No.: PCT/EP2005/001449

§ 371 (c)(1),
(2), (4) Date: Aug. 14, 2006

(87) PCT Pub. No.: WO2005/077950

PCT Pub. Date: Aug. 25, 2005

(65) Prior Publication Data

US 2007/0135456 A1    Jun. 14, 2007

(30) Foreign Application Priority Data

Feb. 14, 2004  (GB)  ................. 0403282.7
Oct. 22, 2004  (GB)  ................. 0423562.8
Dec. 24, 2004  (GB)  ................. 0428375.0

(51) Int. Cl.
  C07D 473/06   (2006.01)
  A61K 31/522   (2006.01)
  A61P 9/10     (2006.01)
  A61P 3/06     (2006.01)
  A61P 3/10     (2006.01)
  C07D 473/04   (2006.01)

(52) U.S. Cl. ................. 514/263.34; 544/271; 544/272; 544/273

(58) Field of Classification Search ................. 544/271; 514/263.34
  See application file for complete search history.

(56) References Cited

U.S. PATENT DOCUMENTS

| | | | | |
|---|---|---|---|---|
| 2,797,220 | A | * | 6/1957 | Blicke ................. 544/271 |
| 5,473,070 | A | | 12/1995 | Underiner et al. |
| 5,780,476 | A | | 7/1998 | Underiner et al. |
| 5,807,861 | A | | 9/1998 | Klein et al. |
| 5,981,535 | A | * | 11/1999 | Spicer et al. ........... 514/263.34 |
| 6,043,250 | A | | 3/2000 | Klein et al. |
| 6,100,271 | A | | 8/2000 | Klein et al. |
| 6,103,730 | A | | 8/2000 | Klein et al. |
| 6,133,274 | A | | 10/2000 | Underiner et al. |
| 6,469,017 | B1 | | 10/2002 | Klaus et al. |
| 6,693,105 | B1 | | 2/2004 | Underiner et al. |
| 6,774,130 | B2 | | 8/2004 | Klein et al. |
| 6,780,865 | B1 | | 8/2004 | Porubek et al. |
| 6,878,715 | B1 | | 4/2005 | Klein et al. |
| 2003/0207901 | A1 | | 11/2003 | Underiner et al. |
| 2004/0077645 | A1 | | 4/2004 | Himmelsbach et al. |
| 2005/0032748 | A1 | | 2/2005 | Klein et al. |
| 2005/0049262 | A1 | | 3/2005 | Klein et al. |
| 2006/0205711 | A1 | | 9/2006 | Himmelsbach et al. |
| 2009/0209561 | A1 | | 8/2009 | Hatley et al. |

FOREIGN PATENT DOCUMENTS

| | | |
|---|---|---|
| EP | 0 389 282 | 9/1990 |
| EP | 1171442 B1 | 7/2005 |
| WO | WO 92/09203 | 6/1992 |
| WO | WO 93/16699 | 9/1993 |
| WO | WO 93/17684 | 9/1993 |
| WO | WO 94/11001 | 5/1994 |
| WO | WO 94/22449 | 10/1994 |
| WO | WO 94/22863 | 10/1994 |
| WO | WO 94/24133 | 10/1994 |
| WO | WO 95/20589 | 8/1995 |
| WO | WO 95/22546 | 8/1995 |
| WO | WO 99/20280 | 4/1999 |
| WO | WO 9936073 | 7/1999 |
| WO | WO 02/24698 | 3/2002 |
| WO | WO 02/68420 | 9/2002 |
| WO | WO 02/084298 | 10/2002 |
| WO | WO 00/61583 | 10/2003 |
| WO | WO 06/045564 | 5/2006 |

OTHER PUBLICATIONS

Arch, Jonathan et al., "Inhibition of Type 4 Cyclic Nucleotide Phosphodiesterase by 8-Chloraxanthines" Archiv Der Pharmazie (Weinheim, Germany) 329(4), 1996, pp. 205-208 Coden: Arpmas; ISSN: 0365-6233, Compounds 2, 19.

(Continued)

Primary Examiner—Mark L Berch
(74) Attorney, Agent, or Firm—Grace C. Hsu; John Lemanowicz; Charles Kinzig

(57) ABSTRACT

The present invention relates to a therapeutically active xanthine derivative compound of formula (I):

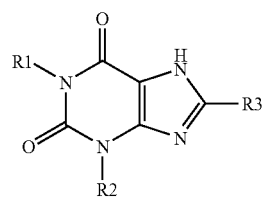

corresponding pharmaceutical formulations containing, manufacture processes for, methods or uses of such compounds in therapy, in particular for treatment of diseases where under-activation of the HM74A receptor contributes to such diseases or where activation of the HM74A receptor will be beneficial.

20 Claims, No Drawings

OTHER PUBLICATIONS

Jacobson, Kenneth et al., "Effect of Trifluoromethyl and Other Substituents on Activity of Xanthines at Adenosine Receptors", J. of Med. Chem., vol. 36, No. (18), 1993, pp. 2639-2644 Coden: JMCMAR; ISSN: 0022-2623, cited in the application, compound 28.

Katsushima et al., "Structure-Activity Relationships of 8-Cycloalkyl_1, 3-Dipropylxanthines as Antagonists of Adenosine Receptors", J. of Med. Chem., American Chemical Society, Washington, DC, US, vol. 33, Jul. 1, 1990, pp. 1906-1910.

Kattus, Albert A., et al., "Diuretic Activity of Compounds Related to Xanthines, Uracils, and Triazines as Determined in Dogs", Bulletin of the Johns Hopkins Hospital, 1951, 89, 1-8 Coden: JHHBAI; ISSN: 0097-1383.

Smellie, F. W., et al., "Alkylxanthines: Inhibition of Adenosine-Elicited Accumulation of Cyclic AMP in Brain Slices and of Brain Phosphodiesterase Activity", 1979, Life Sciences, vol. 24, No. 26, pp. 2475-2481.

U. S. Appl. No. 12/063,434, Feb. 9, 2009, Hatley et al.

* cited by examiner

XANTHINES WITH HM74A RECEPTOR ACTIVITY

The present invention relates to therapeutically active compounds which are xanthine derivatives, processes for the manufacture of said derivatives, pharmaceutical formulations containing the active compounds and the use of the compounds in therapy, particularly in the treatment of diseases where under-activation of the HM74A receptor contributes to the disease or where activation of the receptor will be beneficial.

Dyslipidaemia is a general term used to describe individuals with aberrant lipoprotein profiles. Clinically, the main classes of compounds used for the treatment of patients with dyslipidaemia, and therefore at risk of cardiovascular disease are the statins, fibrates, bile-acid binding resins and nicotinic acid. Nicotinic acid (Niacin, a B vitamin) has been used clinically for over 40 years in patients with various forms of dyslipidaemia. The primary mode of action of nicotinic acid is via inhibition of hormone-sensitive triglyceride lipase (HSL), which results in a lowering of plasma non-esterified fatty acids (NEFA) which in turn alters hepatic fat metabolism to reduce the output of LDL and VLDL (low and very low density lipoprotein). Reduced VLDL levels are thought to lower cholesterol ester transfer protein (CETP) activity to result in increased HDL (high density lipoprotein) levels which may be the cause of the observed cardiovascular benefits. Thus, nicotinic acid produces a very desirable alteration in lipoprotein profiles; reducing levels of VLDL and LDL whilst increasing HDL. Nicotinic acid has also been demonstrated to have disease modifying benefits, reducing the progression and increasing the regression of atherosclerotic lesions and reducing the number of cardiovascular events in several trials.

The observed inhibition of HSL by nicotinic acid treatment is mediated by a decrease in cellular cyclic adenosine monophosphate (cAMP) caused by the G-protein-mediated inhibition of adenylyl cyclase. Recently, the G-protein coupled receptors HM74 and HM74A have been identified as receptors for nicotinic acid (PCT patent application WO02/84298; Wise et. al. J Biol Chem., 2003, 278 (11), 9869-9874). The DNA sequence of human HM74A may be found in Genbank; accession number AY148884. Two further papers support this discovery, (Tunaru et. al. Nature Medicine, 2003, 9(3), 352-255 and Soga et. al. Biochem Biophys Res Commun., 2003, 303 (1) 364-369), however the nomenclature differs slightly. In the Tunaru paper what they term human HM74 is in fact HM74A and in the Soga paper HM74b is identical to HM74A. Cells transfected to express HM74A and/or HM74 gain the ability to elicit $G_i$ G-protein mediated responses following exposure to nicotinic acid. In mice lacking the homologue of HM74A (m-PUMA-G) nicotinic acid fails to reduce plasma NEFA levels.

Certain xanthine derivatives have been synthesised and disclosed in the prior art. For example, EP0389282 discloses xanthine derivatives as potential mediators of cerebrovascular disorders. A range of xanthine derivatives were identified as adenosine receptor antagonists by Jacobson et. al. in J. Med. Chem., 1993, 36, 2639-2644.

We now present a group of xanthine derivatives which are selective agonists of the nicotinic acid receptor HM74A and are thus of benefit in the treatment, prophylaxis and suppression of diseases where under-activation of this receptor either contributes to the disease or where activation of the receptor will be beneficial.

SUMMARY OF THE INVENTION

The present invention provides therapeutically active xanthine derivatives and the use of these derivatives in therapy, particularly in the treatment of diseases where under-activation of the HM74A receptor contributes to the disease or where activation of the receptor will be beneficial, in particular diseases of lipid metabolism including dyslipidaemia or hyperlipoproteinaemia such as diabetic dyslipidaemia and mixed dyslipidaemia, heart failure, hypercholesteraemia, cardiovascular disease including atherosclerosis, arteriosclerosis, and hypertriglyceridaemia. As such, the compounds may also find favour as therapeutics for coronary artery disease, thrombosis, angina, chronic renal failure, peripheral vascular disease and stroke, as well as the cardiovascular indications associated with type II diabetes mellitus, type I diabetes, insulin resistance, hyperlipidaemia, anorexia nervosa, obesity. The compounds may also be of use in the treatment of inflammatory diseases or conditions, as set out further below.

Intermediates, formulations, methods and processes described herein form further aspects of the invention.

DETAILED DESCRIPTION OF THE INVENTION

According to one aspect of this invention, we provide a compound of Formula (I)

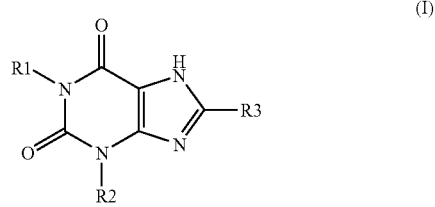

and a physiologically functional derivative thereof, wherein
$R^1$ is selected from: hydrogen and $C_{1-4}$ alkyl which may be optionally substituted with one or more groups selected from CN and $CF_3$;
$R^2$ is selected from: $C_{3-10}$ unsubstituted alkyl, $C_{1-10}$ alkyl substituted with one or more groups selected from fluorine and CN, $C_5$ alkenyl, unbranched $C_4$ alkenyl, and $C_{1-4}$ alkyl substituted with cycloalkyl;
and $R^3$ is selected from halogen and CN;
with the proviso that:
(i) when $R^3$ represents Cl, and $R^1$ represents ethyl, $R^2$ is other than propyl;
(ii) when $R^3$ represents Br, and $R^1$ represents propyl, $R^2$ is other than propyl;
(iii) when $R^3$ represents Cl or Br, and $R^1$ represents butyl, $R^2$ is other than butyl; and
(iv) when $R^1$ represents $C_{1-4}$ alkyl, $CH_2CN$, or $(CH_2)_3CF_3$, $R^2$ is other than branched alkyl.

The compounds are of use in the treatment of diseases where under-activation of the HM74A receptor contributes to the disease or where activation of the receptor will be beneficial, in particular diseases of lipid metabolism including dyslipidaemia or hyperlipoproteinaemia such as diabetic dyslipidaemia and mixed dyslipidaemia, heart failure, hypercholesteraemia, cardiovascular disease including atherosclerosis, arteriosclerosis, and hypertriglyceridaemia. As such, the compounds may also find favour as therapeutics for coronary artery disease, thrombosis, angina, chronic renal failure, peripheral vascular disease and stroke, as well as the cardiovascular indications associated with type II diabetes mellitus, type I diabetes, insulin resistance, hyperlipidaemia, anorexia nervosa, obesity. As such the compounds of the present invention may find use as agonists or partial agonists of HM74A (HM74A modulators).

In particular embodiments, $R^1$ is selected from: hydrogen, $C_{1-4}$ alkyl, $CH_2CN$ and $(CH_2)_3CF_3$; In more particular embodiments $R^1$ is selected from: hydrogen and methyl.

In certain embodiments, $R^2$ is selected from: $C_{3-10}$ unsubstituted alkyl, $C_{1-6}$alkyl with one or more CN substitutions, $C_{1-10}$ alkyl with one or more fluorine substitutions, $C_5$ alkenyl, unbranched $C_4$ alkenyl, and $C_{1-4}$ alkyl substituted with cycloalkyl. Particularly $R^2$ is selected from: $C_{3-10}$ unsubstituted alkyl; $(CH_2)_{1-5}CN$; $C_{2-5}$ alkyl with one or more fluorine substitutions; $C_5$ alkenyl; and $C_{1-4}$ alkyl substituted with cycloalkyl. More particularly $R^2$ is selected from $C_{4-6}$ unsubstituted n-alkyl, for example pentyl; $(CH_2)_{1-3}CN$, for example, $(CH_2)CN$ or $(CH_2)_3CN$; $C_{3-4}$ alkyl with one or more fluorine substitutions, in particular where the terminal carbon is fully saturated with fluorine, for example $(CH_2)_{2-3}CF_3$; and $C_5$ alkenyl, in particular, where there is only one double bond, for example where the double bond is located between the fourth and fifth carbons (terminal alkenyl).

In particular embodiments, $R^3$ represents halogen. More particularly, $R^3$ is selected from: chlorine and bromine. Most particularly, $R^3$ represents chlorine.

It is to be understood that the present invention includes any combination of particular embodiments and covers all combinations of particular substituents described hereinabove.

Particular compounds of the present invention include:
(8-Chloro-2,6-dioxo-1,2,6,7-tetrahydro-3H-purin-3-yl)acetonitrile,
3-Butyl-8-chloro-3,7-dihydro-1H-purine-2,6-dione,
8-Chloro-1-methyl-3-pentyl-3,7-dihydro-1H-purine-2,6-dione,
8-Chloro-3-(4,4,4-trifluorobutyl)-3,7-dihydro-1H-purine-2,6-dione,
8-Bromo-1-methyl-3-pentyl-3,7-dihydro-1H-purine-2,6-dione,
8-Chloro-3-(3,3,3-trifluoropropyl)-3,7-dihydro-1H-purine-2,6-dione,
8-Chloro-1-propyl-3-(2,2,2-trifluoroethyl)-3,7-dihydro-1H-purine-2,6-dione,
3-Butyl-8-chloro-1-methyl-3,7-dihydro-1H-purine-2,6-dione,
(3-Butyl-8-chloro-2,6-dioxo-2,3,6,7-tetrahydro-1H-purin-1-yl)acetonitrile,
8-Chloro-3-(2-cyclopropylethyl)-3,7-dihydro-1H-purine-2,6-dione,
8-Chloro-1,3-bis(4,4,4-trifluorobutyl)-3,7-dihydro-1H-purine-2,6-dione,
4-(8-Chloro-1-methyl-2,6-dioxo-1,2,6,7-tetrahydro-3H-purin-3-yl)butanenitrile,
8-Chloro-1-ethyl-3-(2,2,2-trifluoroethyl)-3,7-dihydro-1H-purine-2,6-dione,
1-Methyl-2,6-dioxo-3-pentyl-2,3,6,7-tetrahydro-1H-purine-8-carbonitrile,
8-Chloro-3-propyl-1-methyl-3,7-dihydro-1H-purine-2,6-dione,
8-Chloro-3-(3-methylbutyl)-3,7-dihydro-1H-purine-2,6-dione,
8-Chloro-3-pentyl-3,7-dihydro-1H-purine-2,6-dione,
8-Chloro-3-propyl-3,7-dihydro-1H-purine-2,6-dione,
3-Butyl-1-methyl-2,6-dioxo-2,3,6,7-tetrahydro-1H-purine-8-carbonitrile,
8-Chloro-3-(4-penten-1-yl)-3,7-dihydro-1H-purine-2,6-dione,
8-Chloro-3-hexyl-3,7-dihydro-1H-purine-2,6-dione,
4-(8-Chloro-2,6-dioxo-1,2,6,7-tetrahydro-3H-purin-3-yl)butanenitrile,
8-Chloro-3-hexyl-1-methyl-3,7-dihydro-1H-purine-2,6-dione,
3-Butyl-8-chloro-1-ethyl-3,7-dihydro-1H-purine-2,6-dione,
[8-Chloro-3-(2-cyclopropylethyl)-2,6-dioxo-2,3,6,7-tetrahydro-1H-purin-1-yl]acetonitrile,
(8-Chloro-2,6-dioxo-3-propyl-2,3,6,7-tetrahydro-1H-purin-1-yl)acetonitrile,
8-Chloro-1-(4,4,4-trifluorobutyl)-3-(2,2,2-trifluoroethyl)-3,7-dihydro-1H-purine-2,6-dione,
8-Chloro-3-(2,2,2-trifluoroethyl)-3,7-dihydro-1H-purine-2,6-dione,
2,2'-(8-Chloro-2,6-dioxo-6,7-dihydro-1H-purine-1,3(2H)-diyl)diacetonitrile,
8-Chloro-1-methyl-3-(4,4,4-trifluorobutyl)-3,7-dihydro-1H-purine-2,6-dione,
8-Chloro-3-(2-cyclohexylethyl)-3,7-dihydro-1H-purine-2,6-dione,
1,3-Dibutyl-2,6-dioxo-2,3,6,7-tetrahydro-1H-purine-8-carbonitrile,
1,3-Dibutyl-8-iodo-3,7-dihydro-1H-purine-2,6-dione,
8-Chloro-3-(4-methylpentyl)-3,7-dihydro-1H-purine-2,6-dione,
8-Chloro-3-(6-methylheptyl)-3,7-dihydro-1H-purine-2,6-dione,
8-Chloro-3-octyl-3,7-dihydro-1H-purine-2,6-dione,
8-Chloro-3-decyl-3,7-dihydro-1H-purine-2,6-dione,
8-Chloro-3-(cyclohexylmethyl)-3,7-dihydro-1H-purine-2,6-dione,
(+/-)-8-Chloro-3-(3-methylpentyl)-3,7-dihydro-1H-purine-2,6-dione,
8-Chloro-3-(2-cyclopentylethyl)-3,7-dihydro-1H-purine-2,6-dione,
8-Chloro-3-(cyclopropylmethyl)-3,7-dihydro-1H-purine-2,6-dione,
(+/-)-8-Chloro-3-(2-methylbutyl)-3,7-dihydro-1H-purine-2,6-dione,
(+/-)-8-Chloro-3-(2-methylpentyl)-3,7-dihydro-1H-purine-2,6-dione,
8-Chloro-3-(cyclobutylmethyl)-3,7-dihydro-1H-purine-2,6-dione,
8-Chloro-3-(cyclopentylmethyl)-3,7-dihydro-1H-purine-2,6-dione,
8-Chloro-3-(3-cyclopropylpropyl)-3,7-dihydro-1H-purine-2,6-dione,
8-Chloro-3-(2-cyclobutylethyl)-3,7-dihydro-1H-purine-2,6-dione,
8-Chloro-3-(4-fluorobutyl)-3,7-dihydro-1H-purine-2,6-dione,
8-Chloro-3-(3-fluoropropyl)-3,7-dihydro-1H-purine-2,6-dione,
8-Chloro-3-(5-fluoropentyl)-3,7-dihydro-1H-purine-2,6-dione,
4-(8-Chloro-1-methyl-2,6-dioxo-1,2,6,7-tetrahydro-3H-purin-3-yl)butanenitrile,
3-(3-Buten-1-yl)-8-chloro-3,7-dihydro-1H-purine-2,6-dione,
6-(8-Chloro-2,6-dioxo-1,2,6,7-tetrahydro-3H-purin-3-yl)-2,2-dimethylhexanenitrile, 8-Chloro-3-(6-fluorohexyl)-3,7-dihydro-1H-purine-2,6-dione.

Throughout the present specification and the accompanying claims the words "comprise" and "include" and variations such as "comprises", "comprising", "includes" and "including" are to be interpreted inclusively. That is, these words are intended to convey the possible inclusion of other elements or integers not specifically recited, where the context allows.

As used herein, the terms "halogen" or "halo" refer to fluorine, chlorine, bromine and iodine.

As used herein, the term "alkyl" (when used as a group or as part of a group) refers to a straight or branched hydrocarbon chain unless specified otherwise, containing the specified number of carbon atoms. For example, $C_3$-$C_{10}$alkyl means a straight or branched hydrocarbon chain containing at least 3 and at most 10 carbon atoms. Examples of alkyl as used herein include, but are not limited to methyl (Me), ethyl (Et), n-propyl and i-propyl. The term "n-alkyl" refers specifically to an un-branched hydrocarbon chain.

As used herein, the term "cycloalkyl" refers to a hydrocarbon ring containing between 3 and 6 carbon atoms, comprising no heteroatoms or conjugated double bonds. Examples of cycloalkyl as used herein include, but are not limited to cyclopropyl and cyclohexyl.

As used herein, the term "alkenyl" refers to a straight or branched hydrocarbon chain containing the specified number of carbon atoms which contains one or more double bonds.

As used herein, where a group is referred to as being "substituted" with another group or having "one or more substitutions" unless a particular position for such a substitution is specified it is to be understood that a substitution may be present at any position in the group.

As used herein, the term "physiologically functional derivative" refers to any pharmaceutically acceptable derivative of a compound of the present invention, for example an amide thereof, and includes any pharmaceutically acceptable salt of a compound of formula (I), and any pharmaceutically acceptable solvate of a compound of formula (I) which, upon administration to a mammal, such as a human, is capable of providing (directly or indirectly) a compound of formula (I) or an active metabolite or residue thereof. It will be appreciated by those skilled in the art that the compounds of formula (I) may be modified to provide physiologically functional derivatives thereof at any of the functional groups in the compounds, and that the compounds of formula (I) may be so modified at more than one position.

As used herein, the term "pharmaceutically acceptable" used in relation to an ingredient (active ingredient or excipient) which may be included in a pharmaceutical formulation for administration to a patient, refers to that ingredient being acceptable in the sense of being compatible with any other ingredients present in the pharmaceutical formulation and not being deleterious to the recipient thereof.

As used herein, the term "solvate" refers to a complex of variable stoichiometry formed by a solute (in this invention, a compound of formula (I), a salt thereof or a physiologically functional derivative thereof) and a solvent. Such solvents for the purposes of the present invention may not interfere with the biological activity of the solute. The solvent used may be a pharmaceutically acceptable solvent. Examples of suitable pharmaceutically acceptable solvents include water, ethanol and acetic acid. An example of a solvent that may be used is water, in which case the solvate may be referred to as a hydrate of the solute in question.

It will be appreciated that, for pharmaceutical use, the "salt or solvate" referred to above will be a pharmaceutically acceptable salt or solvate. However, other salts or solvates may find use, for example, in the preparation of a compound of formula (I) or in the preparation of a pharmaceutically acceptable salt or solvate thereof.

Pharmaceutically acceptable salts include those described by Berge, Bighley and Monkhouse, *J. Pharm. Sci.*, 1977, 66, 1-19. Suitable pharmaceutically acceptable salts include alkali metal salts formed from the addition of alkali metal bases such as alkali metal hydroxides. Examples of suitable alkali metal salts are sodium salt or potassium salt. Other suitable pharmaceutically acceptable salts include alkaline earth metal salts such as calcium salt or magnesium salt, ammonium salts; or salts with organic bases such as ethanolamine, triethanolamine, ethylene diamine, triethylmine, choline and meglumine; or salts with amino acids such as arginine, lysine and histidine.

Compounds of formula (I) are of potential therapeutic benefit in the treatment and amelioration of the symptoms of many diseases of lipid metabolism including dyslipidaemia or hyperlipoproteinaemia such as diabetic dyslipidaemia and mixed dyslipidaemia, heart failure, hypercholesteraemia, cardiovascular disease including atherosclerosis, arteriosclerosis, and hypertriglyceridaemia, type II diabetes mellitus, type I diabetes, insulin resistance, hyperlipidaemia, anorexia nervosa, obesity. As such, the compounds may also find favour as therapeutics for coronary artery disease, thrombosis, angina, chronic renal failure, peripheral vascular disease and stroke.

Furthermore, it is also believed that the HM74 and HM74A receptors are involved in inflammation. Inflammation represents a group of vascular, cellular and neurological responses to trauma. Inflammation can be characterised as the movement of inflammatory cells such as monocytes, neutrophils and granulocytes into the tissues. This is usually associated with reduced endothelial barrier function and oedema into the tissues. Inflammation with regards to disease typically is referred to as chronic inflammation and can last up to a lifetime. Such chronic inflammation may manifest itself through disease symptoms. The aim of anti-inflammatory therapy is therefore to reduce this chronic inflammation and allow for the physiological process of healing and tissue repair to progress.

Examples of inflammatory diseases or conditions for which the compounds of the present invention may demonstrate utility include those of the joint, particularly arthritis (e.g. rheumatoid arthritis, osteoarthritis, prosthetic joint failure), or the gastrointestinal tract (e.g. ulcerative colitis, Crohn's disease, and other inflammatory bowel and gastrointestinal diseases, gastritis and mucosal inflammation resulting from infection, the enteropathy provoked by non-steroidal anti-inflammatory drugs), of the lung (e.g. adult respiratory distress syndrome, asthma, cystic fibrosis, or chronic obstructive pulmonary disease), of the heart (e.g. myocarditis), of nervous tissue (e.g. multiple sclerosis), of the pancreas, (e.g. inflammation associated with diabetes melitus and complications thereof, of the kidney (e.g. glomerulonephritis), of the skin (e.g. dermatitis, psoriasis, eczema, urticaria, burn injury), of the eye (e.g. glaucoma) as well as of transplanted organs (e.g. rejection) and multi-organ diseases (e.g. systemic lupus erythematosis, sepsis) and inflammatory sequelae of viral or bacterial infections and inflammatory conditions associated with atherosclerosis and following hypoxic or ischaemic insults (with or without reperfusion), for example in the brain or in ischaemic heart disease.

In particular, the compounds of this invention are useful in the treatment and prevention of inflammation, diabetes and cardiovascular diseases or conditions including atherosclerosis, arteriosclerosis, hypertriglyceridemia, and mixed dyslipidaemia.

Nicotinic acid has a significant side effect profile, possibly because it is dosed at high level (gram quantities daily). The most common side effect is an intense cutaneous flushing. In certain embodiments of the present invention the compounds may exhibit reduced side effects compared to nicotinic acid. HM74A has been identified as a high affinity receptor for nicotinic acid whilst HM74 is a lower affinity receptor. The compounds of the present invention may find use as selective HM74A agonists or partial agonists; in which case they will show greater affinity for HM74A than for HM74.

The potential for compounds of formula (I) to activate HM74A may be demonstrated, for example, using the following enzyme and in vitro whole cell assays:

In-vitro Testing

For transient transfections, HEK293T cells (HEK293 cells stably expressing the SV40 large T-antigen) were maintained in DMEM containing 10% foetal calf serum and 2 mM glutamine. Cells were seeded in 90 mm culture dishes and grown to 60-80% confluence (18-24 h) prior to transfection. Human HM74A (GenBank™ accession number AY148884) was subcloned in to a mammalian expression vector (pcDNA3; Invitrogen) and transfected using Lipofectamine reagent. For transfection, 9 µg of DNA was mixed with 30 µl Lipofectamine in 0.6 ml of Opti-MEM (Life Technologies Inc.) and was incubated at room temperature for 30 min prior to the addition of 1.6 ml of Opti-MEM. Cells were exposed to the Lipofectamine/DNA mixture for 5 h and 6 ml of 20% (v/v) foetal calf serum in DMEM was then added. Cells were harvested 48 h after transfection. Pertussis toxin treatment was carried out by supplementation into media at 50 ngml$^{-1}$ for 16 h. All transient transfection studies involved co-transfection of receptor together with the $G_{i/o}$ G protein, $G_{o1}\alpha$.

For generation of stable cell lines the above method was used to transfect CHO-K1 cells seeded in six well dishes grown to 30% confluence. These cells were maintained in DMEM F-12 HAM media containing 10% foetal calf serum and 2 mM glutamine. 48 h post-transfection the media was supplemented with 400 µg/ml Geneticin (G418, Gibco) for selection of antibiotic resistant cells. Clonal CHO-K1 cell lines stably expressing HM74A were confirmed by [$^{35}$S]-GTPγS binding measurements, following the addition of nicotinic acid.

P2 membrane preparation—Plasma membrane-containing P2 particulate fractions were prepared from cell pastes frozen at −80° C. after harvest. All procedures were carried out at 4° C. Cell pellets were resuspended in 1 ml of 10 mM Tris-HCl and 0.1 mM EDTA, pH 7.5 (buffer A) and by homogenisation for 20 s with a Ultra Turrax followed by passage (5 times) through a 25-gauge needle. Cell lysates were centrifuged at 1,000 g for 10 min in a microcentrifuge to pellet the nuclei and unbroken cells and P2 particulate fractions were recovered by microcentrifugation at 16,000 g for 30 min. P2 particulate fractions were resuspended in buffer A and stored at −80° C. until required.

[$^{35}$S]-GTPγS binding—assays were performed at room temperature in 384-well format based on methods described previously, (Wieland, T. and Jakobs, K. H. (1994) *Methods Enzymol.* 237, 3-13). Briefly, the dilution of standard or test compounds were prepared and added to a 384-well plate in a volume of 10 µl. Membranes (HM74A or HM74) were diluted in assay buffer (20 mM HEPES, 100 mM NaCl, 10 mM MgCl$_2$, pH7.4) supplemented with saponin (60 µg/ml), Leadseeker WGA beads (Amersham; 250 µg/well) and 10 µM GDP, so that the 20 µl volume added to each well contains 5 µg of membranes. [$^{35}$S]-GTPγS (1170 Ci/mmol, Amersham) was diluted (1:1500) in assay buffer and 20 µl added to each well. Following the addition of the radioligand, the plates were sealed, pulse spun and incubated for 4 hours at room temperature. At the end of the incubation period the plates were read on a Leadseeker machine (VIEWLUX PLUS; Perkin-Elmer) to determine the levels of specific binding.

In-vivo Testing

HM74A agonists were tested in male Spague-Dawley rats (200-250 g) which had been fasted for at least 12 hours prior to the study. The compounds were dosed intravenously (5 ml/kg) or by oral gavage (10 ml/kg). Blood samples (0.3 ml tail vein bleed) were taken pre-dose and at three times post-dose (times ranging from 15 minutes to 8 hours post-dose). Each blood sample was transferred to a heparin tube (Becton Dickinson Microtainer, PST LH) and centrifuged (10,000 g for 5 minutes) to produce a plasma sample. The plasma samples were assayed for levels of non-esterified fatty acids (NEFA) using a commercially available kit (Randox). Inhibition of plasma NEFA levels, relative to pre-dose levels, was used as a surrogate for HM74A agonist activity.

In order to determine whether HM74A compounds exhibited the flushing response associated with nicotinic acid they were dosed to anaesthetised guinea-pigs. Male Dunkin Hartley guinea pigs (300-800 g) were fasted for 12 hours prior to being anaesthetised with a mixture of Ketamine hydrochloride (Vetalar, 40 mg/kg i.m.), Xylazine (Rompun, 8 mg/kg i.m.) and sodium pentobarbitone (Sagatal, 30 mg/kg i.p.). Following anaesthesia a tracheostomy was performed and the animals were mechanically ventilated with room air (10-12 mL/kg, 60 breaths/min). A jugular vein, and a carotid artery, were cannulated for intravenous administration of test compound and collection of blood respectively. An infra-red temperature probe (Extech Instruments) was placed 3-5 mm from the tip of the left ear. Temperature measurements were recorded every minute from 5 minutes prior to test compound and up to 40 minutes post-administration of test compound. Data was automatically collected on a Psion computer before being transferred for data analysis within an Excel spreadsheet. Prior to, and at frequent time points after, compound administration, blood samples (0.3 ml) were taken via the carotid arterial cannula and transferred to Microtainer (BD) tubes containing lithium heparin. The samples were mixed thoroughly on a blood roller and then stored on ice prior to centrifugation at 1200 g for 5 minutes.

Nicotinic acid (10 mg/kg i.v.) produced a mean (±s.e.m.) increase in ear temperature equivalent to 10.42±1.44 (area under curve; arbitary units; n=6). By comparison, the compound of Example 30 (10 mg/kg i.v.) produced a mean (±s.e.m.) increase in ear temperature equivalent to 1.52±0.39 (area under curve; arbitary units; n=6), a reduction of 85%.

Compounds according to Formula (I) have been synthesised (see synthetic examples below) and tested in one or more of the assays discussed above. All of the exemplified compounds have a pEC50 of 4.9 (±0.3 log unit) or greater and an efficacy of 30% or greater. Some particular compounds are exemplified below.

General Purification and Analytical Methods:

The mass spectra (MS) were recorded on a Fisons VG Platform mass spectrometer using electrospray positive ionisation [(ES+ve to give MH$^+$ and M(NH$_4$)$^+$ molecular ions] or electrospray negative ionisation [(ES−ve to give (M−H)$^-$ molecular ion] modes.

$^1$H NMR spectra were recorded using a Bruker DPX 400 MHz spectrometer using tetramethylsilane as the external standard.

Biotage™ chromatography refers to purification carried out using equipment sold by Dyax Corporation (either the Flash 40i or Flash 150i) and cartridges pre-packed with KPSil.

Mass directed autoprep refers to methods where the material was purified by high performance liquid chromatography on a HPLCABZ+ 5 μm column (5 cm×10 mm i.d.) with 0.1% $HCO_2H$ in water and 95% MeCN, 5% water (0.5% $HCO_2H$) utilising the following gradient elution conditions: 0-1.0 minutes 5% B, 1.0-8.0 minutes 5→30% B, 8.0-8.9 minutes 30% B, 8.9-9.0 minutes 30→95% B, 9.0-9.9 minutes 95% B, 9.9-10 minutes 95→0% B at a flow rate of 8 ml minutes$^{-1}$ (System 2). The Gilson 202-fraction collector was triggered by a VG Platform Mass Spectrometer on detecting the mass of interest.

Preparative h.p.l.c. refers to methods where the material was purified by high performance liquid chromatography on a HPLCABZ+ 5 μm column (10 cm×21.2 mm i.d.) with 0.1% $HCO_2H$ in water (A) and MeCN (0.5% $HCO_2H$) (B) utilising the generic gradient elution conditions expressed as "x to y" gradient with a gradient system as follows: 0-1.45 minutes x % B, 1.45-20 minutes x→y % B, 20-24 minutes y→95% B, 24-30 minutes 95% B, 32-34 minutes 95→x % B at a flow rate of 8 ml minutes$^{-1}$. The Gilson 233 fraction collector was triggered by UV (254 nm).

SPE (solid phase extraction) refers to the use of cartridges sold by International Sorbent Technology Ltd.

Strata Phenyl SPE refers to the use of cartridges sold by Phenomenex. The compound was loaded onto a cartridge previously conditioned with MeCN and equilibrated with 5% MeCN in water. The compound was eluted with 0.1% $HCO_2H$ in water and MeCN (0.5% $HCO_2H$) in a suitable gradient on a Combiflash Optix 10.

As indicated above, compounds of Formula (I) may find use in human or veterinary medicine, in particular as activators of HM74A, in the management of dyslipidaemia and hyperlipoproteinaemia.

Thus, there is provided as a further aspect of the present invention a compound of formula (I) or a physiologically functional derivative thereof, for use in human or veterinary medicine, particularly in the treatment of disorders of lipid metabolism including dyslipidaemia or hyperlipoproteinaemia such as diabetic dyslipidaemia and mixed dyslipidaemia, heart failure, hypercholesteraemia, cardiovascular disease including atherosclerosis, arteriosclerosis, and hypertriglyceridaemia, type II diabetes mellitus, type I diabetes, insulin resistance, hyperlipidaemia, anorexia nervosa, obesity. As such, the compounds are also provided for use in the treatment of coronary artery disease, thrombosis, angina, chronic renal failure, peripheral vascular disease and stroke.

There is provided as a further aspect of the present invention a compound of formula (I) or a physiologically functional derivative thereof, for use in the manufacture of a medicament for the treatment of disorders of lipid metabolism including dyslipidaemia or hyperlipoproteinaemia such as diabetic dyslipidaemia and mixed dyslipidaemia, heart failure, hypercholesteraemia, cardiovascular disease including atherosclerosis, arteriosclerosis, and hypertriglyceridaemia, type II diabetes mellitus, type I diabetes, insulin resistance, hyperlipidaemia, anorexia nervosa, obesity. As such, the compounds are also provided for use in the treatment of coronary artery disease, thrombosis, angina, chronic renal failure, peripheral vascular disease and stroke.

It will be appreciated that references herein to treatment extend to prophylaxis, prevention of recurrence and suppression of symptoms as well as the treatment of established conditions.

According to another aspect of the invention, there is provided the use of a compound of formula (II)

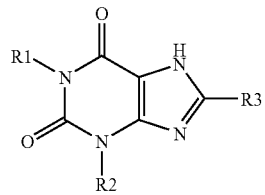

and physiologically functional derivative thereof, wherein:

$R^1$ is selected from: hydrogen and $C_{1-4}$ alkyl which may be optionally substituted with one or more groups selected from CN and $CF_3$;

$R^2$ is selected from: $C_{2-10}$ unsubstituted alkyl, $C_{1-10}$ alkyl substituted with one or more groups selected from fluorine and CN, $C_5$ alkenyl, unbranched $C_4$ alkenyl, and $C_{1-4}$ alkyl substituted with cycloalkyl;

and $R^3$ is selected from halogen and CN;

in the manufacture of a medicament for the treatment of disorders of lipid metabolism including dyslipidaemia or hyperlipoproteinaemia. In particular, the use is provided of a compound of Formula (II) in the manufacture of a medicament for the treatment of diabetic dyslipidaemia or mixed dyslipidaemia, heart failure, hypercholesteraemia, type II diabetes mellitus, type I diabetes, insulin resistance, hyperlipidaemia, anorexia nervosa, obesity, coronary artery disease, thrombosis, angina, chronic renal failure, stroke and cardiovascular disease including atherosclerosis, arteriosclerosis, and hypertriglyceridaemia.

In one embodiment of the invention, there is provided a compound of formula (II) for use in the treatment of disorders of lipid metabolism including dyslipidaemia or hyperlipoproteinaemia. In particular, the use is provided of a compound of Formula (II) in the manufacture of a medicament for the treatment of diabetic dyslipidaemia or mixed dyslipidaemia, heart failure, hypercholesteraemia, type II diabetes mellitus, type I diabetes, insulin resistance, hyperlipidaemia, anorexia nervosa, obesity, coronary artery disease, thrombosis, angina, chronic renal failure, stroke and cardiovascular disease including atherosclerosis, arteriosclerosis, and hypertriglyceridaemia.

In particular embodiments, $R^1$ is selected from: hydrogen, $C_{1-4}$ alkyl, $CH_2CN$ and $(CH_2)_3CF_3$. In more particular embodiments $R^1$ is selected from: hydrogen and methyl.

In certain embodiments $R^2$ is selected from: $C_{3-10}$ unsubstituted alkyl, $C_{1-10}$ alkyl substituted with one or more groups selected from fluorine and CN, $C_5$ alkenyl, unbranched $C_4$ alkenyl, and $C_{1-4}$ alkyl substituted with cycloalkyl. Particularly, $R^2$ is selected from: $C_{3-10}$ unsubstituted alkyl, $C_{1-6}$alkyl with one or more CN substitutions, $C_{1-10}$ alkyl with one or more fluorine substitutions, $C_5$ alkenyl, unbranched $C_4$ alkenyl, and $C_{1-4}$ alkyl substituted with cycloalkyl. More particularly $R^2$ is selected from: $C_{3-10}$ unsubstituted alkyl; $(CH_2)_{1-5}$ CN; $C_{2-5}$ alkyl with one or more fluorine substitutions; $C_5$ alkenyl; and $C_{1-4}$ alkyl substituted with cycloalkyl. Most particularly $R^2$ is selected from $C_{4-6}$ unsubstituted n-alkyl, for example pentyl; $(CH_2)_{1-3}CN$, for example, $(CH_2)CN$ or $(CH_2)_3CN$; $C_{3-4}$ alkyl with one or more fluorine substitutions, in particular where the terminal carbon is fully saturated with fluorine, for example $(CH_2)_{2-3}CF_3$; and $C_5$ alkenyl, in particular, where there is only one double bond, for example where the double bond is located between the fourth and fifth carbons (terminal alkenyl).

In particular embodiments, $R^3$ represents halogen. More particularly, $R^3$ is selected from chlorine and bromine. Most particularly, $R^3$ represents chlorine.

Particular compounds for use in the treatment of, or in the manufacture of a medicament for the treatment of disorders of lipid metabolism including dislipidaemia or hyperlipoproteinaemia include:

(8-Chloro-2,6-dioxo-1,2,6,7-tetrahydro-3H-purin-3-yl)acetonitrile,
3-Butyl-8-chloro-3,7-dihydro-1H-purine-2,6-dione,
8-Chloro-1-methyl-3-pentyl-3,7-dihydro-1H-purine-2,6-dione,
8-Chloro-3-(4,4,4-trifluorobutyl)-3,7-dihydro-1H-purine-2,6-dione,
8-Bromo-1-methyl-3-pentyl-3,7-dihydro-1H-purine-2,6-dione,
8-Chloro-3-(3,3,3-trifluoropropyl)-3,7-dihydro-1H-purine-2,6-dione,
8-Chloro-1-propyl-3-(2,2,2-trifluoroethyl)-3,7-dihydro-1H-purine-2,6-dione,
3-Butyl-8-chloro-1-methyl-3,7-dihydro-1H-purine-2,6-dione,
(3-Butyl-8-chloro-2,6-dioxo-2,3,6,7-tetrahydro-1H-purin-1-yl)acetonitrile,
8-Chloro-3-(2-cyclopropylethyl)-3,7-dihydro-1H-purine-2,6-dione,
8-Chloro-1,3-bis(4,4,4-trifluorobutyl)-3,7-dihydro-1H-purine-2,6-dione,
4-(8-Chloro-1-methyl-2,6-dioxo-1,2,6,7-tetrahydro-3H-purin-3-yl)butanenitrile,
8-Chloro-1-ethyl-3-(2,2,2-trifluoroethyl)-3,7-dihydro-1H-purine-2,6-dione,
1-Methyl-2,6-dioxo-3-pentyl-2,3,6,7-tetrahydro-1H-purine-8-carbonitrile,
8-Chloro-3-propyl-1-methyl-3,7-dihydro-1H-purine-2,6-dione,
8-Chloro-3-(3-methylbutyl)-3,7-dihydro-1H-purine-2,6-dione,
8-Chloro-3-pentyl-3,7-dihydro-1H-purine-2,6-dione,
8-Chloro-3-propyl-3,7-dihydro-1H-purine-2,6-dione,
3-Butyl-1-methyl-2,6-dioxo-2,3,6,7-tetrahydro-1H-purine-8-carbonitrile,
8-Chloro-3-(4-penten-1-yl)-3,7-dihydro-1H-purine-2,6-dione,
8-Chloro-3-hexyl-3,7-dihydro-1H-purine-2,6-dione,
4-(8-Chloro-2,6-dioxo-1,2,6,7-tetrahydro-3H-purin-3-yl)butanenitrile,
8-Chloro-3-hexyl-1-methyl-3,7-dihydro-1H-purine-2,6-dione,
3-Butyl-8-chloro-1-ethyl-3,7-dihydro-1H-purine-2,6-dione,
[8-Chloro-3-(2-cyclopropylethyl)-2,6-dioxo-2,3,6,7-tetrahydro-1H-purin-1-yl]acetonitrile,
(8-Chloro-2,6-dioxo-3-propyl-2,3,6,7-tetrahydro-1H-purin-1-yl)acetonitrile,
8-Chloro-1-(4,4,4-trifluorobutyl)-3-(2,2,2-trifluoroethyl)-3,7-dihydro-1H-purine-2,6-dione,
8-Chloro-3-(2,2,2-trifluoroethyl)-3,7-dihydro-1H-purine-2,6-dione,
2,2'-(8-Chloro-2,6-dioxo-6,7-dihydro-1H-purine-1,3(2H)-diyl)diacetonitrile,
8-Chloro-1-methyl-3-(4,4,4-trifluorobutyl)-3,7-dihydro-1H-purine-2,6-dione,
8-Chloro-3-(2-cyclohexylethyl)-3,7-dihydro-1H-purine-2,6-dione,
1,3-Dibutyl-2,6-dioxo-2,3,6,7-tetrahydro-1H-purine-8-carbonitrile,
1,3-Dibutyl-8-iodo-3,7-dihydro-1H-purine-2,6-dione,
8-Chloro-3-(4-methylpentyl)-3,7-dihydro-1H-purine-2,6-dione,
8-Chloro-3-(6-methylheptyl)-3,7-dihydro-1H-purine-2,6-dione,
8-Chloro-3-octyl-3,7-dihydro-1H-purine-2,6-dione,
8-Chloro-3-decyl-3,7-dihydro-1H-purine-2,6-dione,
8-Chloro-3-(cyclohexylmethyl)-3,7-dihydro-1H-purine-2,6-dione,
(+/−)-8-Chloro-3-(3-methylpentyl)-3,7-dihydro-1H-purine-2,6-dione,
8-Chloro-3-(2-cyclopentylethyl)-3,7-dihydro-1H-purine-2,6-dione,
8-Chloro-3-(cyclopropylmethyl)-3,7-dihydro-1H-purine-2,6-dione,
(+/−)-8-Chloro-3-(2-methylbutyl)-3,7-dihydro-1H-purine-2,6-dione,
(+/−)-8-Chloro-3-(2-methylpentyl)-3,7-dihydro-1H-purine-2,6-dione,
8-Chloro-3-(cyclobutylmethyl)-3,7-dihydro-1H-purine-2,6-dione,
8-Chloro-3-(cyclopentylmethyl)-3,7-dihydro-1H-purine-2,6-dione,
8-Chloro-3-(3-cyclopropylpropyl)-3,7-dihydro-1H-purine-2,6-dione,
8-Chloro-3-(2-cyclobutylethyl)-3,7-dihydro-1H-purine-2,6-dione,
8-Chloro-3-(4-fluorobutyl)-3,7-dihydro-1H-purine-2,6-dione,
8-Chloro-3-(3-fluoropropyl)-3,7-dihydro-1H-purine-2,6-dione,
8-Chloro-3-(5-fluoropentyl)-3,7-dihydro-1H-purine-2,6-dione,
4-(8-Chloro-1-methyl-2,6-dioxo-1,2,6,7-tetrahydro-3H-purin-3-yl)butanenitrile,
3-(3-Buten-1-yl)-8-chloro-3,7-dihydro-1H-purine-2,6-dione,
6-(8-Chloro-2,6-dioxo-1,2,6,7-tetrahydro-3H-purin-3-yl)-2,2-dimethylhexanenitrile,
8-Chloro-3-(6-fluorohexyl)-3,7-dihydro-1H-purine-2,6-dione,
8-chloro-3-ethyl-1-methyl-3,7-dihydro-1H-purine-2,6-dione.

It is to be understood that this aspect of the present invention includes any combination of particular embodiments and covers all combinations of particular substituents described herein above for compounds of Formula (II).

Additionally, the present invention provides the use of a compound of formula (I) or a physiologically functional derivative thereof, in the manufacture of a medicament for the treatment of inflammatory diseases or conditions of the joint, particularly arthritis (e.g. rheumatoid arthritis, osteoarthritis, prosthetic joint failure), or of the gastrointestinal tract (e.g. ulcerative colitis, Crohn's disease, and other inflammatory bowel and gastrointestinal diseases, gastritis and mucosal inflammation resulting from infection, the enteropathy provoked by non-steroidal anti-inflammatory drugs), of the lung (e.g. adult respiratory distress syndrome, asthma, cystic fibrosis, or chronic obstructive pulmonary disease), of the heart (e.g. myocarditis), of nervous tissue (e.g. multiple sclerosis), of the pancreas, (e.g. inflammation associated with diabetes melitus and complications thereof, of the kidney (e.g. glomerulonephritis), of the skin (e.g. dermatitis, psoriasis, eczema, urticaria, burn injury), of the eye (e.g. glaucoma) as well as of transplanted organs (e.g. rejection) and multi-organ diseases (e.g. systemic lupus erythematosis, sepsis) and inflammatory sequelae of viral or bacterial infections and inflammatory conditions associated with atherosclerosis and following hypoxic or ischaemic insults (with or without reperfusion), for example in the brain or in ischaemic heart disease.

In a further or alternative aspect there is provided a method for the treatment of a human or animal subject with a condition where under-activation of the HM74A receptor contributes to the condition or where activation of the receptor will be beneficial, which method comprises administering to said human or animal subject an effective amount of a compound of formula (I) or a physiologically acceptable salt or solvate thereof.

Again, it is to be understood that this aspect of the present invention includes any combination of particular embodiments and covers all combinations of particular substituents described herein above for compounds of Formula (I).

More particularly, the present invention provides a method for the treatment of disorders of lipid metabolism including dyslipidaemia or hyperlipoproteinaemia such as diabetic dyslipidaemia and mixed dyslipidaemia, heart failure, hypercholesteraemia, cardiovascular disease including atherosclerosis, arteriosclerosis, and hypertriglyceridaemia, type II diabetes mellitus, type I diabetes, insulin resistance, hyperlipidaemia, anorexia nervosa, obesity, which method comprises administering to said human or animal subject an effective amount of a compound of formula (I) or a physiologically acceptable salt or solvate thereof. As such, these compounds may also find favour in methods for the treatment of coronary artery disease, thrombosis, angina, chronic renal failure, peripheral vascular disease and stroke, which methods comprise administering to said human or animal subject an effective amount of a compound of formula (I).

The amount of a HM74A modulator which is required to achieve the desired biological effect will, of course, depend on a number of factors, for example, the mode of administration and the precise clinical condition of the recipient. In general, the daily dose will be in the range of 0.1 mg-1 g/kg, typically 0.1-100 mg/kg. An intravenous dose may, for example, be in the range of 0.01 mg to 0.1 g/kg, typically 0.01 mg to 10 mg/kg, which may conveniently be administered as an infusion of from 0.1 µg to 1 mg, per minute. Infusion fluids suitable for this purpose may contain, for example, from 0.01 µg to 0.1 mg, per millilitre. Unit doses may contain, for example, from 0.01 µg to 1 g of a HM74A modulator. Thus ampoules for injection may contain, for example, from 0.01 µg to 0.1 g and orally administrable unit dose formulations, such as tablets or capsules, may contain, for example, from 0.1 mg to 1 g. No toxicological effects are indicated/expected when a compound of the invention is administered in the above mentioned dosage range.

A compound of the present invention may be employed as the compound per se in the treatment of a disease where under-activation of the HM74A receptor contributes to the disease or where activation of the receptor will be beneficial, an example of this is where a compound of the present invention is presented with an acceptable carrier in the form of a pharmaceutical formulation. The carrier must, of course, be acceptable in the sense of being compatible with the other ingredients of the formulation and must not be deleterious to the recipient. The carrier may be a solid or a liquid, or both, and may be formulated with the HM74A modulator as a unit-dose formulation, for example, a tablet, which may contain from 0.05% to 95% by weight of the HM74A modulator.

The formulations include those suitable for oral, rectal, topical, buccal (e.g. sub-lingual) and parenteral (e.g. subcutaneous, intramuscular, intradermal or intravenous) administration.

There is also provided according to the invention a process for preparation of such a pharmaceutical composition which comprises mixing the ingredients.

Formulations suitable for oral administration may be presented in discrete units, such as capsules, cachets, lozenges or tablets, each containing a predetermined amount of a HM74A modulator; as a powder or granules; as a solution or a suspension in an aqueous or non-aqueous liquid; or as an oil-in-water or water-in-oil emulsion. In general, the formulations are prepared by uniformly and intimately admixing the active HM74A modulator with a liquid or finely divided solid carrier, or both, and then, if necessary, shaping the product. For example, a tablet may be prepared by compressing or moulding a powder or granules of the HM74A modulator optionally with one or more accessory ingredients. Compressed tablets may be prepared by compressing, in a suitable machine, the compound in a free-flowing form, such as a powder or granules optionally mixed with a binder, lubricant, inert diluent and/or surface active/dispersing agent(s). Moulded tablets may be made by moulding, in a suitable machine, the powdered compound moistened with an inert liquid diluent.

Tablets and capsules for oral administration may contain conventional excipients such as binding agents, for example syrup, acacia, gelatin, sorbitol, tragacanth, mucilage of starch or polyvinyl pyrrolidone; fillers, for example, lactose, microcrystalline cellulose, sugar, maize-starch, calcium phosphate or sorbitol; lubricants, for example, magnesium stearate, stearic acid, talc, polyethylene glycol or silica; disintegrants, for example, potato starch, croscarmellose sodium or sodium starch glycollate; or wetting agents such as sodium lauryl sulphate. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxymethyl cellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example almond oil, fractionated coconut oil, oily esters, propylene glycol or ethyl alcohol; or preservatives, for example, methyl or propyl p-hydroxybenzoates or sorbic acid. The preparations may also contain buffer salts, flavouring, colouring and/or sweetening agents (e.g. mannitol) as appropriate.

Formulations suitable for buccal (sub-lingual) administration include lozenges comprising a HM74A modulator in a flavoured base, usually sucrose and acacia or tragacanth, and pastilles comprising the HM74A modulator in an inert base such as gelatin and glycerin or sucrose and acacia.

Formulations of the present invention suitable for parenteral administration conveniently comprise sterile aqueous preparations of an HM74A modulator, the formulation may be isotonic with the blood of the intended recipient. These preparations could be administered intravenously, although administration may also be effected by means of subcutaneous, intramuscular, or intradermal injection. Such preparations may conveniently be prepared by admixing the HM74A modulator with water and rendering the resulting solution sterile and isotonic with the blood. Injectable compositions according to the invention will generally contain from 0.1 to 5% w/w of the HM74A modulator.

Thus, formulations of the present invention suitable for parenteral administration comprising a compound according to the invention may be formulated for parenteral administration by bolus injection or continuous infusion and may be presented in unit dose form, for instance as ampoules, vials, small volume infusions or pre-filled syringes, or in multi-dose containers with an added preservative. The compositions may take such forms as solutions, suspensions, or emulsions in aqueous or non-aqueous vehicles, and may contain formulatory agents such as anti-oxidants, buffers, antimicrobial agents and/or toxicity adjusting agents. Alternatively, the active ingredient may be in powder form for constitution with a suitable vehicle, e.g. sterile, pyrogen-free water, before use. The dry solid presentation may be prepared by filling a sterile powder aseptically into individual sterile containers or by filling a sterile solution aseptically into each container and freeze-drying.

Formulations suitable for rectal administration may be presented as unit-dose suppositories. These may be prepared by admixing a HM74A modulator with one or more conventional solid carriers, for example, cocoa butter or glycerides and then shaping the resulting mixture.

Formulations suitable for topical application to the skin may take the form of an ointment, cream, lotion, paste, gel, spray, aerosol, or oil. Carriers which may be used include vaseline, lanolin, polyethylene glycols, alcohols, and combinations of two or more thereof. The HM74A modulator is generally present at a concentration of from 0.1 to 15% w/w of the composition, for example, from 0.5 to 2%.

By topical administration as used herein, we include administration by insufflation and inhalation. Examples of various types of preparation for topical administration include ointments, creams, lotions, powders, pessaries, sprays, aerosols, capsules or cartridges for use in an inhaler or insufflator or drops (e.g. eye or nose drops).

Ointments and creams may, for example, be formulated with an aqueous or oily base with the addition of suitable thickening and/or gelling agents and/or solvents. Such bases may thus, for example, include water and/or an oil such as liquid paraffin or a vegetable oil such as arachis oil or castor oil or a solvent such as a polyethylene glycol. Thickening agents which may be used include soft paraffin, aluminium stearate, cetostearyl alcohol, polyethylene glycols, microcrystalline wax and beeswax.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents or suspending agents.

Spray compositions may be formulated, for example, as aqueous solutions or suspensions or as aerosols delivered from pressurised packs, with the use of a suitable propellant, e.g. dichlorodifluoromethane, trichlorofluoromethane, dichlorotetrafluoroethane, 1,1,1,2,3,3,3-heptafluoropropane, 1,1,1,2-tetrafluorethane, carbon dioxide or other suitable gas.

Capsules and cartridges for use in an inhaler or insufflator, of for example gelatin, may be formulated containing a powder mix of a compound of the invention and a suitable powder base such as lactose or starch.

The pharmaceutical compositions according to the invention may also be used in combination with other therapeutic agents, for example in combination with other classes of dyslipidaemic drugs (e.g. statins, fibrates, bile-acid binding resins or nicotinic acid).

The compounds of the instant invention may be used in combination with one or more other therapeutic agents for example in combination with other classes of dyslipidaemic drugs e.g. 3-hydroxy-3-methylglutaryl-coenzyme A reductase inhibitors (statins) or fibrates or bile acid binding resins or nicotinic acid. The invention thus provides, in a further aspect, the use of such a combination in the treatment of diseases where under-activation of the HM74A receptor contributes to the disease or where activation of the receptor will be beneficial and the use of a compound of formula (I) or (II) or a pharmaceutically acceptable salt, solvate or physiologically functional derivative thereof in the manufacture of a medicament for the combination therapy of disorders of lipid metabolism including dyslipidaemia or hyperlipoproteinaemia such as diabetic dyslipidaemia and mixed dyslipidaemia, heart failure, hypercholesteraemia, cardiovascular disease including atherosclerosis, arteriosclerosis, and hypertriglyceridaemia, type II diabetes mellitus, type I diabetes, insulin resistance, hyperlipidaemia, anorexia nervosa or obesity.

When the compounds of the present invention are used in combination with other therapeutic agents, the compounds may be administered either sequentially or simultaneously by any convenient route.

The combinations referred to above may conveniently be presented for use in the form of a pharmaceutical formulation and thus pharmaceutical formulations comprising a combination as defined above optimally together with a pharmaceutically acceptable carrier or excipient comprise a further aspect of the invention. The individual components of such combinations may be administered either sequentially or simultaneously in separate or combined pharmaceutical formulations.

When combined in the same formulation it will be appreciated that the two components must be stable and compatible with each other and the other components of the formulation and may be formulated for administration. When formulated separately they may be provided in any convenient formulation, conveniently in such a manner as are known for such compounds in the art.

When in combination with a second therapeutic agent active against the same disease, the dose of each component may differ from that when the compound is used alone. Appropriate doses will be readily appreciated by those skilled in the art.

The invention thus provides, in a further aspect, a combination comprising a compound of formula (I) or (II) or a physiologically acceptable salt or solvate thereof together with another therapeutically active agent.

The combination referred to above may conveniently be presented for use in the form of a pharmaceutical formulation and thus pharmaceutical formulations comprising a combination as defined above together with a pharmaceutically acceptable carrier thereof represent a further aspect of the invention.

The compounds of the present invention have useful duration of action.

The compounds of the present invention and salts and solvates thereof may be prepared by the methodology described hereinafter, constituting a further aspect of this invention.

Process A:
A process according to the invention for preparing a compound of formula (I) or formula (II) in which $R^1$ is H or is the same as $R^2$ and $R^3$ is Cl, comprises:

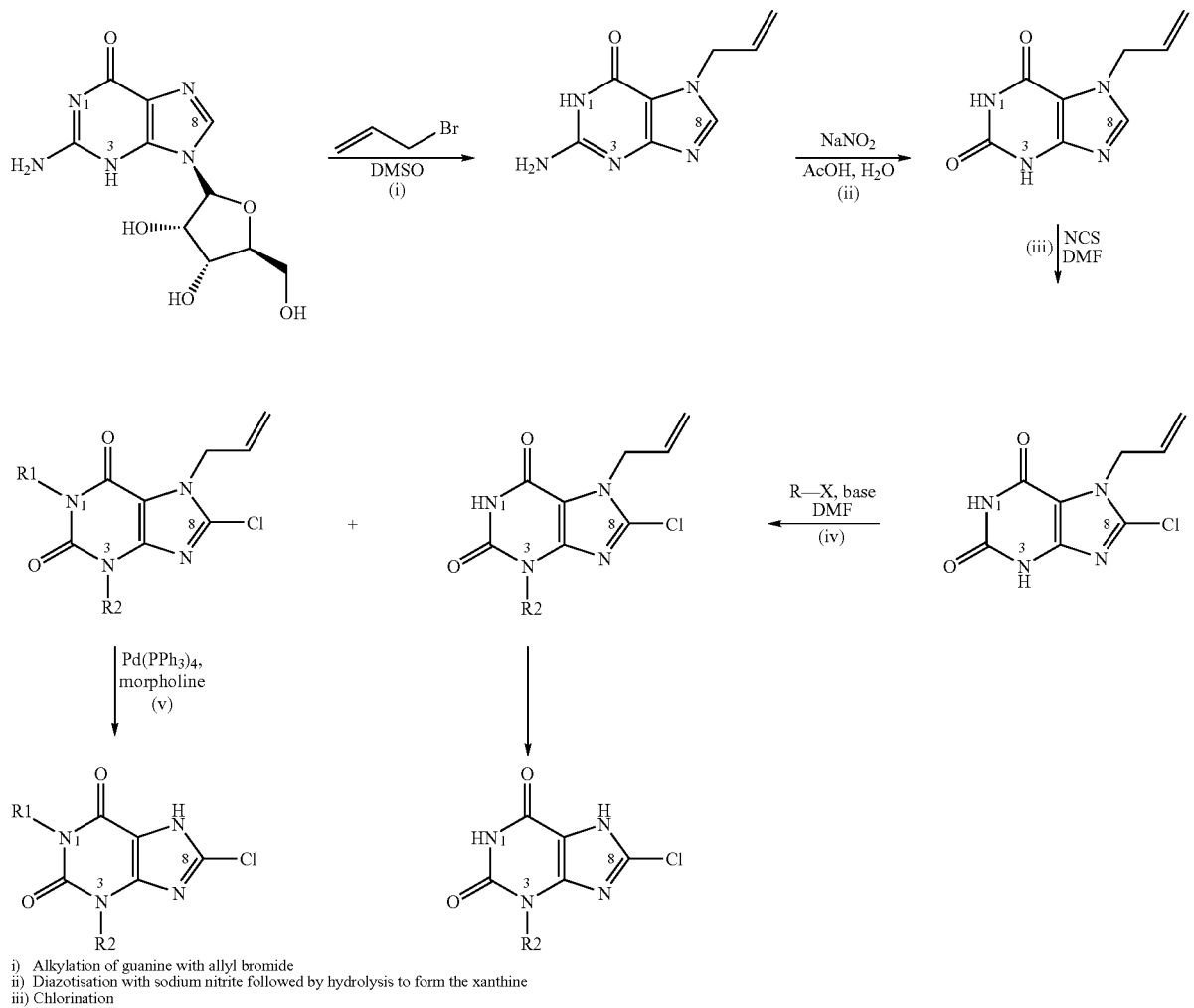

i) Alkylation of guanine with allyl bromide
ii) Diazotisation with sodium nitrite followed by hydrolysis to form the xanthine
iii) Chlorination
iv) Alkylation at N3 and/or dialkylation at N1 and N3
v) Palladium catalysed removal of the allyl group Process B:
A process according to the invention for preparing a compound of formula (I) or formula (II) in which $R^3$ is CN comprises steps (i) and (ii) of Process A followed by:

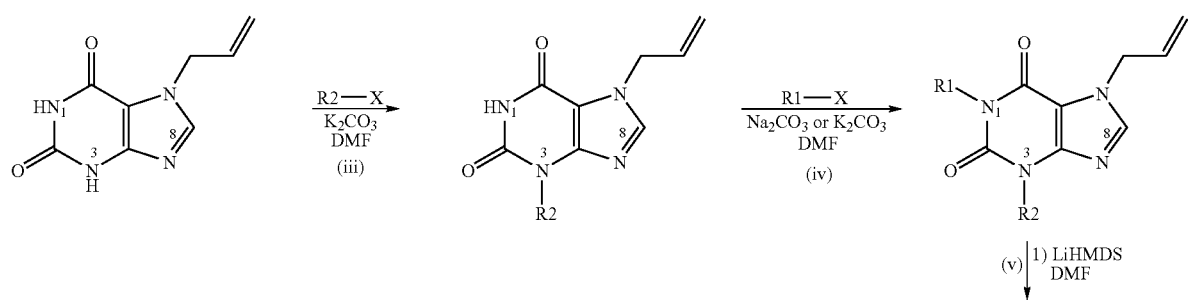

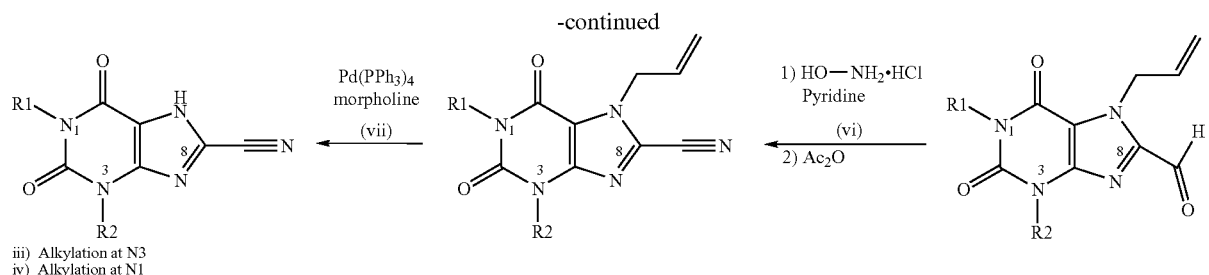

iii) Alkylation at N3
iv) Alkylation at N1
v) Formation of aldehyde at C8 by lithiation with LiHMDS and DMF quench
vi) Conversion of the aldehyde to the nitrile
vii) Palladium catalysed removal of the allyl group Process C:

A process according to the invention for preparing a compound of formula (I) or formula (II) in which $R^3$ is Cl or Br comprises steps (i) to (iv) of Process B followed by:

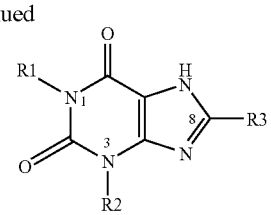

R3 = Cl or Br i) Halogenation at C8 using NCS or NBS
ii) Palladium catalysed removal of the allyl group

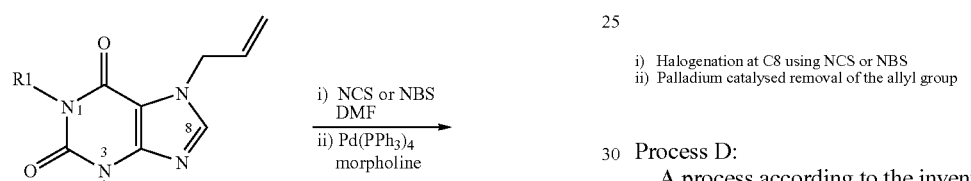

Process D:

A process according to the invention for preparing a compound of formula (I) or formula (II) in which $R^3$ is CN comprises steps (i) to (iv) of Process B followed by:

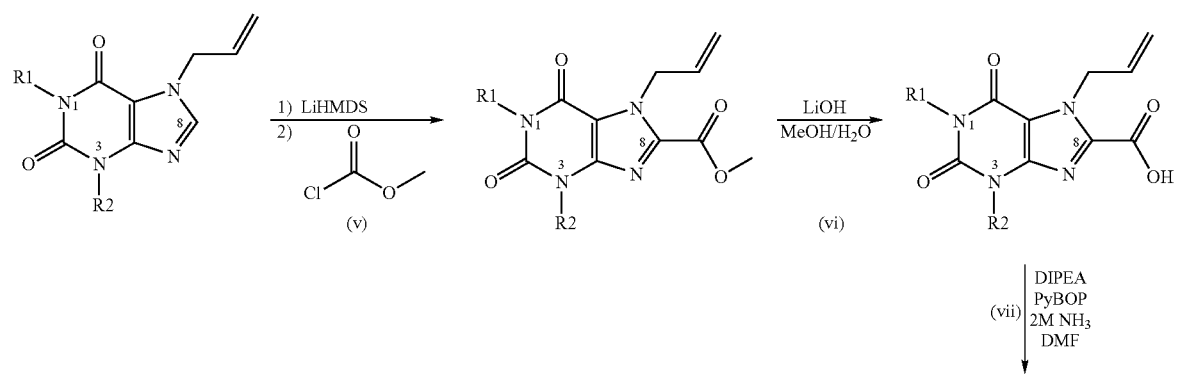

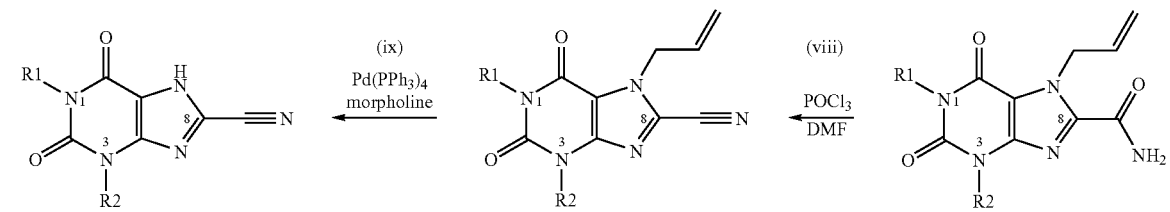

v) Formation of ester
vi) Hydrolysis of the methyl ester
vii) Conversion of the acid to the amide.
viii) Conversion of the amide to the nitrile
ix) Palladium catalysed removal of the allyl group Process E:

A process according to the invention for preparing a compound of formula (I) or formula (II) in which $R^3$ is Cl comprises:

i) Alkylation at N3
ii) Alkylation at N1
iii) Debenzylation
iv) Chlorination at C8

Process F:

A process according to the invention for preparing a compound of formula (I) or formula (II) in which $R^1$ differs from $R^2$ and $R^3$ is Cl comprises steps (i) to (iv) of Process A followed by:

v) Alkylation at N1
vi) Palladium catalysed removal of the allyl group

Process G:

A process according to the invention for preparing a compound of formula (I) or formula (II) in which $R^1$ differs from

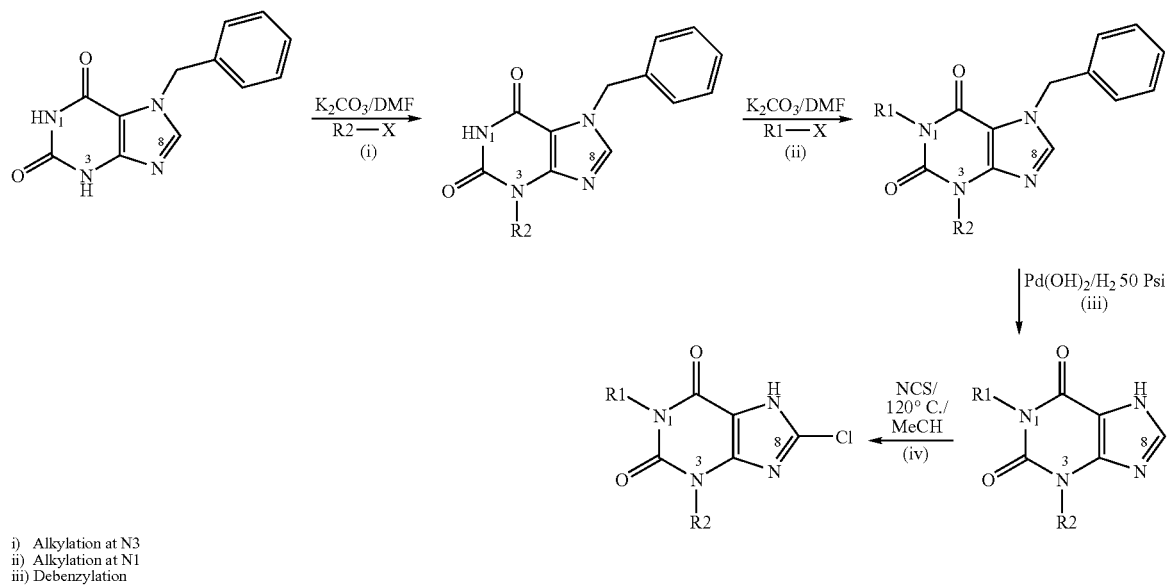

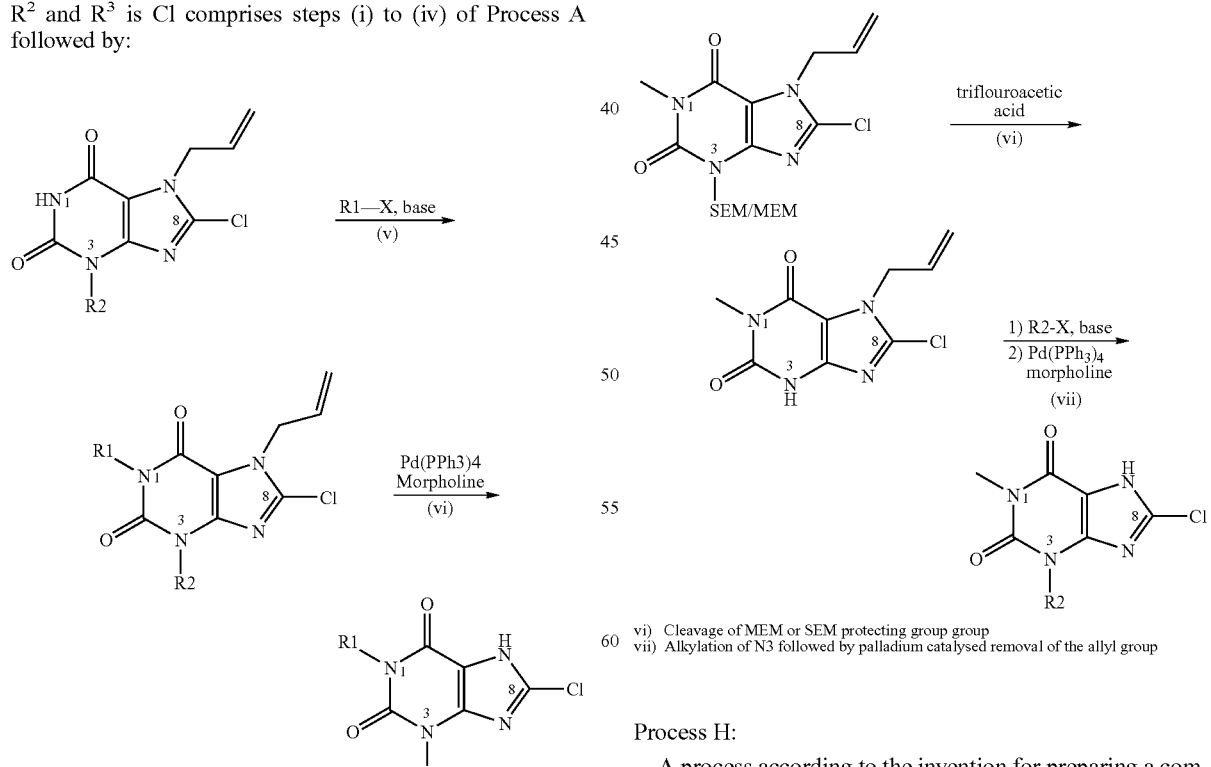

$R^2$ and $R^3$ is Cl comprises steps (i) to (v) of Process F (where $R^2$ from process F is specifically SEM or MEM) followed by:

vi) Cleavage of MEM or SEM protecting group group
vii) Alkylation of N3 followed by palladium catalysed removal of the allyl group Process H:

A process according to the invention for preparing a compound of formula (I) or formula (II) in which $R^3$ is Cl, Br, I or F comprises steps (i) to (iv) of Process B followed by:

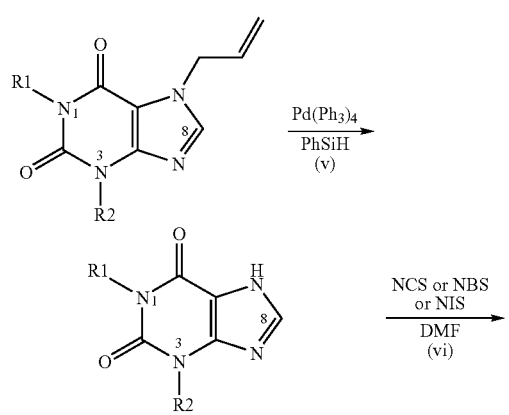
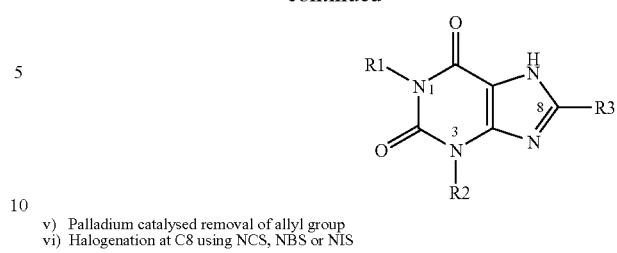

v) Palladium catalysed removal of allyl group
vi) Halogenation at C8 using NCS, NBS or NIS Process I:

A process according to the invention for preparing a compound of formula (I) or formula (II) in which $R^1$ is H or alkyl, $R^2$ is alkyl and $R^3$ is Cl comprises:

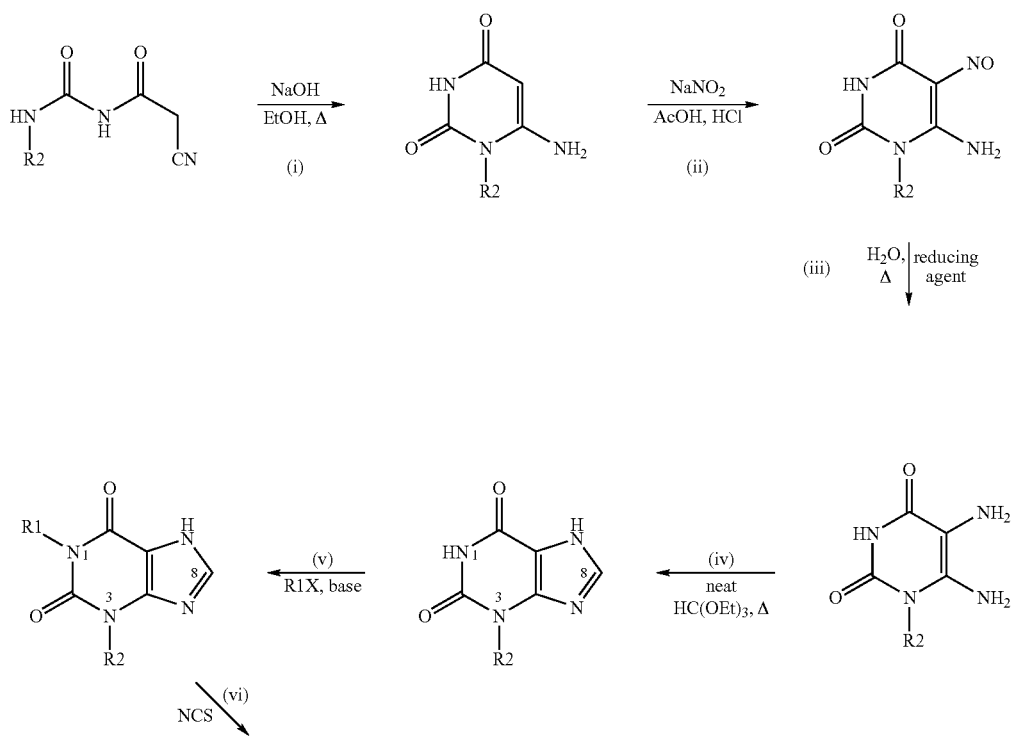

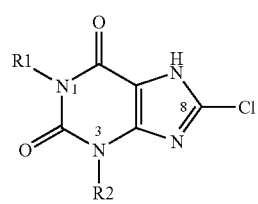

i) Pyrimidinedione formation
ii) Nitrosation
iii) Reduction using $Na_2S_2O_4$ or a similar reducing agent
iv) Xanthine formation
v) Alkylation at N1 (optional)
vi) Halogenation at C8 using NCS Where desired or necessary, as a final stage in any of the above synthetic processes, a resultant compound of formula (I) or (II) can be converted into a physiologically acceptable salt form or vice versa or converting one salt form into another physiologically acceptable salt form.

Abbreviations
THF Tetrahydrofuran
Ac Acetyl
DCM Dichloromethane
DMEM Dulbecco's Modified Eagle's Medium
HEPES 4-(2-Hydroxyethyl)piperazine-1-ethanesulphonic acid
DMSO Dimethylsulphoxide
NBS N-bromosuccinimide
NCS N-chlorosuccinimide
NIS N-iodosuccinimide
DMF Dimethylformamide
LiHMDS Lithium hexamethyldisilylamide
DBAD Dibenzylazodicarboxylate
DIPEA Diisopropylethylamine
PyBOP Benzotriazo-1-yloxytripyrrolidinophosphonium hexafluorophosphate
MEM Methoxyethyloxymethyl
SEM 2-(trimethylsilyl)ethoxymethyl
TFA Trifluoroacetic acid
RT room temperature
Δ Heat The following non-limiting examples illustrate the present invention:

SYNTHETIC EXAMPLES

Example 1

8-Chloro-3-(4-penten-1-yl)-3,7-dihydro-1H-purine-2,6-dione

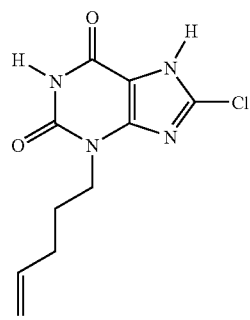

a) 2-amino-7-(2-propen-1-yl)-1,7-dihydro-6H-purin-6-one

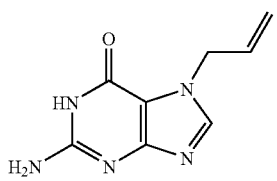

A mixture of guanosine (20 g, 0.071 mol), allyl bromide (14.7 ml, 0.169 mol) and anhydrous DMSO (100 ml) was stirred at rt, under nitrogen, for 18 hours. Concentrated HCl (50 ml of 37%) was added in one portion and the mixture stirred for 45 minutes then poured into MeOH (600 ml). The methanolic solution was neutralised with 2M NaOH(aq) solution and the resulting white precipitate collected by filtration. The white solid was dried under vacuum at 50° C. for 18 hours to afford the title compound (16 g crude, 119%). m/z 192.2[MH$^+$].

b) 7-(2-propen-1-yl)-3,7-dihydro-1H-purine-2,6-dione

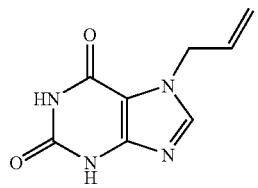

A mixture of 2-amino-7-(2-propen-1-yl)-1,7-dihydro-6H-purin-6-one (40 g, 0.209 mol) in AcOH (900 ml) and water (100 ml) was heated at 55° C. Sodium nitrite (57.74 g, 0.837 mol) in water (100 ml) was added dropwise. Care; toxic fumes. After the addition was complete (approximately 25 minutes) the reaction mixture was allowed to cool to ambient temperature and then concentrated to approximately ⅓ of its original volume. Water (500 ml) was added and the resulting precipitate collected by filtration. The residue was washed with water then dried at 50° C. over P$_2$O$_5$ and under vacuum for 2 hours to give the title compound (17.20 g). The aqueous fraction was concentrated and water added (100 ml). Again the resulting solid was filtered and dried. This gave more of the title compound (2.31 g). Combined product (19.52 g, 49%). m/z 193.2[MH$^+$].

c) 8-chloro-7-(2-propen-1-yl)-3,7-dihydro-1H-purine-2,6-dione

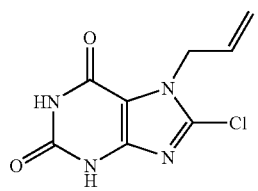

To a solution of 7-(2-propen-1-yl)-3,7-dihydro-1H-purine-2,6-dione (10.52 g, 54.7 mmol) in anhydrous DMF (60 ml) was added NCS (8.04 g, 60.2 mmol). The reaction mixture was left to stir under nitrogen at 20° C. for 6 hours. The reaction mixture was concentrated in vacuo to give an amber oil. MeOH was added and left to stand for 18 hours. The resulting residue was filtered and dried under vacuum to give the title compound (7.69 g, 62%). m/z 227.2[MH$^+$].

d) 8-Chloro-3-(4-penten-1-yl)-3,7-dihydro-1H-purine-2,6-dione

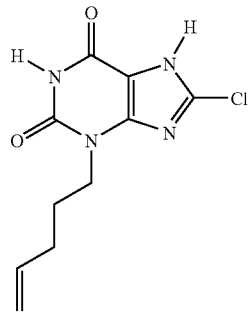

8-Chloro-7-(2-propen-1-yl)-3,7-dihydro-1H-purine-2,6-dione (0.10 g, 0.44 mmol) was dissolved in DMF (1.5 ml) containing sodium carbonate (0.12 g, 0.49 mmol) and 5-bromopentene (0.07 g, 0.49 mmol) and the mixture stirred for 18 h. On completion of alkylation, morpholine (0.5 ml) and tetrakis(triphenylphosphine)palladium (0) (0.08 g, 0.07 mmol) were added and stirring continued for 3.5 h. The reaction was diluted with ethyl acetate (10 ml) washed sequentially with 2N hydrochloric acid (2×5 ml) and brine (3×5 ml) and the organic isolated, dried (MgSO$_4$) and concentrated. The crude product was suspended in methanol (2 ml) and purified on an aminopropyl SPE (5 g) eluting with methanol first then 5% acetic acid in methanol to elute the title compound which was isolated as a white solid after concentration (0.039 g, 35%). NMR; (400MHz, d$^6$-DMSO) 1.75 (m, 2H), 2.05 (m, 2H), 3.85 (t, 2H, J=7 Hz), 4.95 (m, 1H), 5.05 (m, 1H), 5.8 (m, 1H), 11.1 (br s, 1H), one exchangeable proton not observed to $\delta_H$ 13; m/z 255[MH$^+$]

Example 2

8-Chloro-3-hexyl-3,7-dihydro-1H-purine-2,6-dione

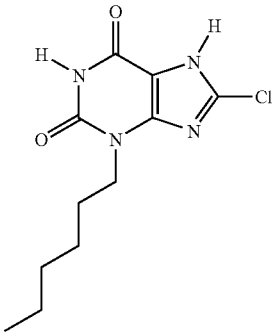

Prepared in similar fashion to Example 1 using hexyl iodide, to afford the title compound.

NMR; $\delta_H$ (400 MHz, d$^6$-DMSO) 0.85 (t, 3H, J=7 Hz), 1.25 (br s, 6H), 1.6 (m, 2H), 3.85 (t, 2H, J=8 Hz), 11.2 (br. s, 1H), one exchangeable proton not observed to $\delta_H$ 13; m/z 271 [MH$^+$]

Examples 3 and 4

(8-chloro-2,6-dioxo-1,2,6,7-tetrahydro-3H-purin-3-yl)acetonitrile and 2,2'-(8-chloro-2,6-dioxo-6,7-dihydro-1H-purine-1,3(2H)-diyl)diacetonitrile

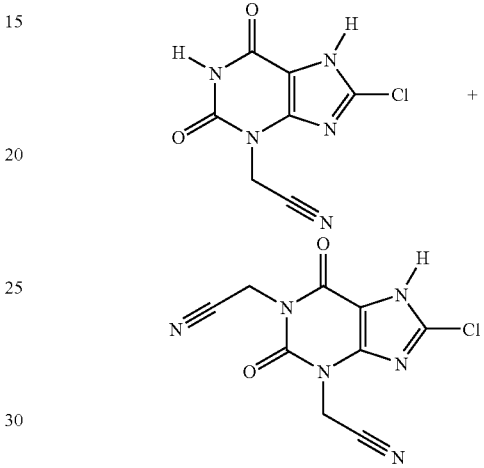

a) [8-chloro-2,6-dioxo-7-(2-propen-1-yl)-1,2,6,7-tetrahydro-3H-purin-3-yl]acetonitrile and 2,2'-[8-chloro-2,6-dioxo-7-(2-propen-1-yl)-6,7-dihydro-1H-purine-1,3(2H)-diyl]diacetonitrile

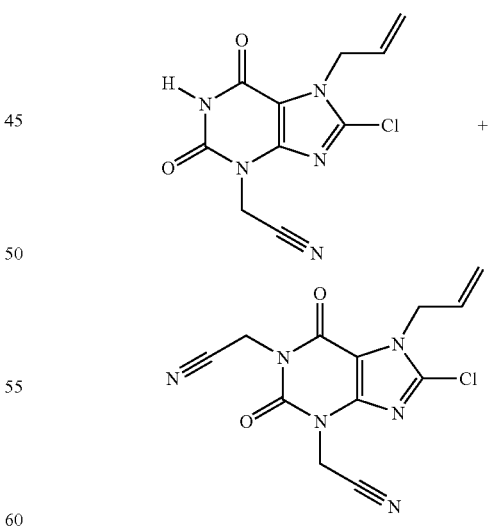

A solution of 8-chloro-7-(2-propen-1-yl)-3,7-dihydro-1H-purine-2,6-dione (0.445 g, 2.0 mmol) in DMF (8 ml) was treated with sodium carbonate (0.18 g, 1.7 mmol) and bromoacetonitrile (0.1 ml, 1.4 mmol). The stirred mixture was heated at 70° C. for 3 hours then cooled to 50° C. and treated with further bromoacetonitrile (0.06 ml, 0.8 mmol). The mixture was maintained at 50° C. for a further 2 hours and then cooled to ambient temperature and evaporated to dryness. The residue was treated with 1M aqueous hydrochloric acid (20 ml) and extracted with ethyl acetate (2×50 ml). The organic fractions were combined, dried over magnesium sulfate, filtered and evaporated. The residue was dissolved in dichloromethane (2 ml), after 20 minutes, the resulting precipitated solid (unreacted 8-chloro-7-(2-propen-1-yl)-3,7-dihydro-1H-purine-2,6-dione was filtered off and washed with further dichloromethane). The filtrate was concentrated in vacuo and subjected to flash chromatography using ethyl acetate/cyclohexane as eluant in a gradient elution from 1:3 to 4:1. To afford the two title compounds:

[8-chloro-2,6-dioxo-7-(2-propen-1-yl)-1,2,6,7-tetrahydro-3H-purin-3-yl]acetonitrile
White solid (0.084 g, 16%); m/z 266 [MH$^+$].

2,2'-[8-chloro-2,6-dioxo-7-(2-propen-1-yl)-6,7-dihydro-1H-purine-1,3(2H)-diyl]diacetonitrile
White solid (0.195 g, 32%); m/z 305 [MH$^+$].

b) (8-chloro-2,6-dioxo-1,2,6,7-tetrahydro-3H-purin-3-yl)acetonitrile

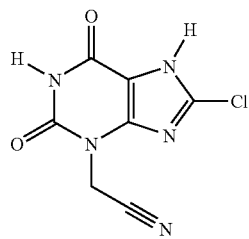

A solution of [8-chloro-2,6-dioxo-7-(2-propen-1-yl)-1,2,6,7-tetrahydro-3H-purin-3-yl]acetonitrile (0.084 g, 0.32 mmol) in THF (5 ml) was degassed by the successive application of vacuum and nitrogen pressure to the reaction mixture. The solution was subsequently treated with morpholine (0.3 ml, 3.4 mmol) and tetrakis(triphenylphosphine)palladium(0) (0.03 g, 0.03 mmol). After 2 hours, the mixture was treated with 2M aqueous hydrochloric acid (3 ml) and chloroform (5 ml). The mixture was separated and the organic phase evaporated. The product was purified from the residue using mass-directed HPLC, to afford the title compound as a white solid (0.018 g, 25%). NMR $\delta_H$ (400 MHz, d$^6$-DMSO) 4.95 (s, 2H), 11.49 (s, 1H), 14.63 (br. s, 1H); m/z 226 [MH$^+$].

c) 2,2'-(8-chloro-2,6-dioxo-6,7-dihydro-1H-purine-1,3(2H)-diyl)diacetonitrile

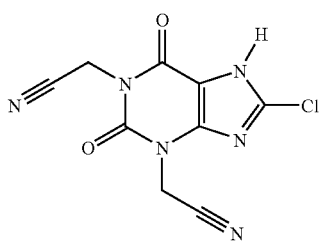

The title compound was prepared from 2,2'-[8-chloro-2,6-dioxo-7-(2-propen-1-yl)-6,7-dihydro-1H-purine-1,3(2H)-diyl]diacetonitrile using the conditions described for the synthesis of (8-chloro-2,6-dioxo-1,2,6,7-tetrahydro-3H-purin-3-yl)acetonitrile.

To afford the title compound as a white solid 0.06 g (4%); NMR $\delta_H$ (400 MHz, d$^6$-DMSO) 4.88 (s, 2H), 5.06 (s, 2H), NH not observed to $\delta_H$ 14; m/z 282 [MNH$_4^+$].

Example 5

8-chloro-3-(3,3,3-trifluoropropyl)-3,7-dihydro-1H-purine-2,6-dione

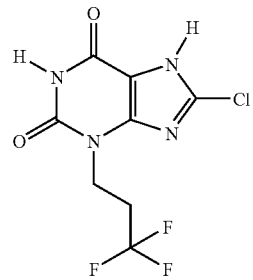

Prepared in similar fashion to Example 3 using 3-bromo-1,1,1-trifluoropropane as alkylating agent to afford title compound.

NMR $\delta_H$ (400 MHz, d$^6$-DMSO) 2.64-2.76 (m, 2H), 4.12 (t, 2H, J=7 Hz), 11.30 (s, 1H), 14.46 (br. s, 1H); m/z 283 [MH$^+$]

Example 6

8-chloro-3-(2,2,2-trifluoroethyl)-3,7-dihydro-1H-purine-2,6-dione

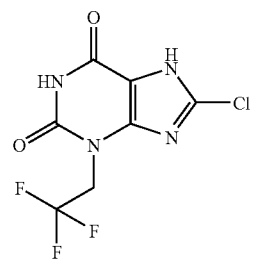

Prepared in similar fashion to Example 3 using 2-bromo-1,1,1-trifluoroethane as the alkylating agent and sodium bicarbonate as base to afford title compound.

$\delta_H$ (400 MHz, d$^4$-MeOD) 4.68 (q, 2H, J=8.5 Hz); m/z 267.1 [M−H]$^−$

Example 7 and 8

8-chloro-3-(4,4,4-trifluorobutyl)-3,7-dihydro-1H-purine-2,6-dione and 8-chloro-1,3-bis(4,4,4-trifluorobutyl)-3,7-dihydro-1H-purine-2,6-dione

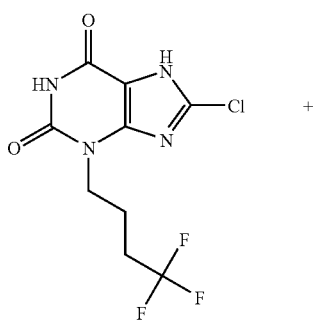

+

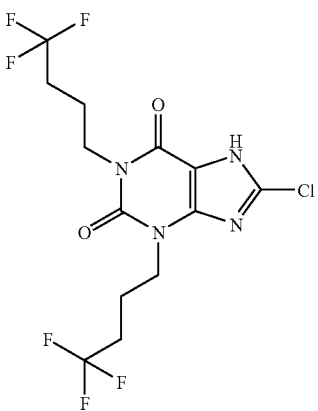

a) 8-chloro-7-(2-propen-1-yl)-3-(4,4,4-trifluorobutyl)-3,7-dihydro-1H-purine-2,6-dione and 8-chloro-7-(2-propen-1-yl)-1,3-bis(4,4,4-trifluorobutyl)-3,7-dihydro-1H-purine-2,6-dione

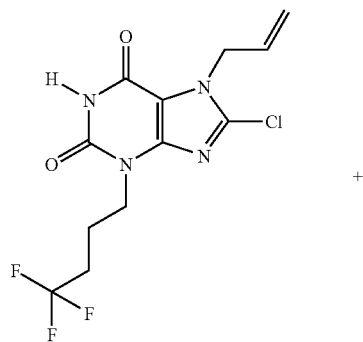

+

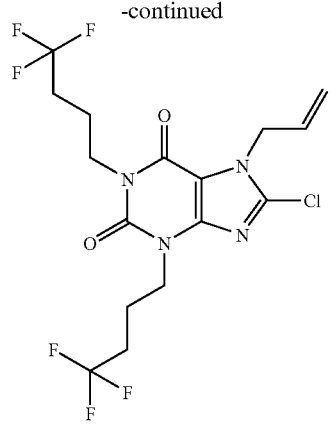

8-chloro-7-(2-propen-1-yl)-3,7-dihydro-1H-purine-2,6-dione (1.5 g, 6.64 mmol), sodium carbonate (844 mg, 7.9 mmol) and 4-bromo-1,1,1-trifluorobutane (1.39 g, 7.3 mmol) were stirred in dimethylformamide (25 ml, dry) for seven days. The reaction mixture was partitioned between ethyl acetate and water. The organic phase was separated and washed with hydrochloric acid (2N), brine, dried (MgSO$_4$) and then evaporated to dryness. The crude product was triturated with ether and the solid collected by filtration to afford 8-chloro-7-(2-propen-1-yl)-3-(4,4,4-trifluorobutyl)-3,7-dihydro-1H-purine-2,6-dione as a white solid (1.23 g, 57%). m/z 337 [MH$^+$].

The reduced filtrate was chromatographed on silica, SPE column (20 g). Elution with cyclohexane:ethylacetate (10:1 to 2:1) afforded 8-chloro-7-(2-propen-1-yl)-1,3-bis(4,4,4-trifluorobutyl)-3,7-dihydro-1H-purine-2,6-dione as a syrup (480 mg, 16%). m/z 447 [MH$^+$].

b) 8-chloro-3-(4,4,4-trifluorobutyl)-3,7-dihydro-1H-purine-2,6-dione

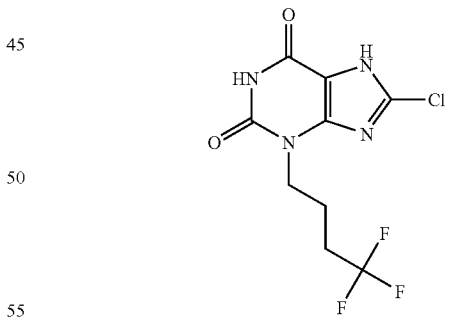

8-chloro-7-(2-propen-1yl)-3-(4,4,4-trifluorobutyl)-3,7-dihydro-1H-purine-2,6-dione (84 mg, 0.25 mmol) and morpholine (220 ul, 2.5 mmol) were degassed with nitrogen in tetrahydrofuran (3 ml) and then tetrakis(triphenylphosphine)palladium(0) (29 mg, 0.025 mmol) was added and the reaction stirred at room temperature overnight. The white precipitate was collected by filtration and washed with tetrahyrofuran and ether to afford the morpholine salt of the title compound (59 mg). This was treated with 2N HCl and methanol and the solvents evaporated to dryness before re-dissolving in DMSO/MeOH and purifying by preparative HPLC using a 10 to 40% gradient to give the title compound (11 mg, 14.9%).

NMR $\delta_H$ (400 MHz, d$^4$-MeOD) 1.92-2.03 (m, 2H), 2.19-2.33 (m, 2H), 4.06 (t, 2H, J=7 Hz); m/z 297 [MH$^+$].

c) 8-chloro-1,3-bis(4,4,4-trifluorobutyl)-3,7-dihydro-1H-purine-2,6-dione

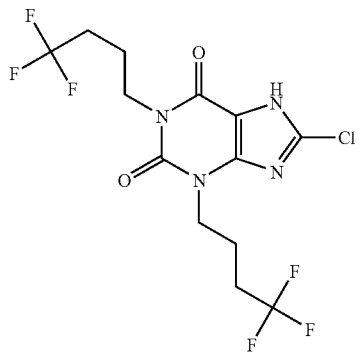

8-chloro-7-(2-propen-1-yl)-1,3-bis(4,4,4-trifluorobutyl)-3,7-dihydro-1H-purine-2,6-dione (478 mg, 1.1 mmol) and morpholine (937 ul, 11 mmol) were degassed with nitrogen in tetrahydrofuran (10 ml) and then tetrakis(triphenylphosphine)palladium(0) (123 mg, 0.11 mmol) was added and the reaction stirred at room temperature overnight. The reaction mixture was partitioned between dichloromethane and hydrochloric acid 2N. The organic phase was separated and reduced to give the crude product. This was purified by aminopropyl SPE (5 g) followed by re-crystallisation from acetonitrile to afford the title compound (75.5 mg, 16.9%). NMR. $\delta_H$ (400 MHz, CDCl$_3$) 1.96-2.13 (m, 4H), 2.15-2.29 (m, 4H), 4.15-4.23 (m, 4H), 12.94 (br. s, 1H); m/z 407 [MH$^+$].

Example 9

8-chloro-3-(2-cyclopropylethyl)-3,7-dihydro-1H-purine-2,6-dione

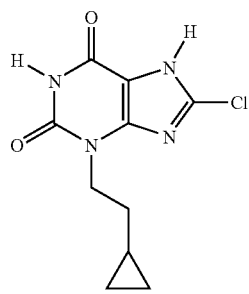

a) 8-chloro-3-(2-cyclopropylethyl)-7-(2-propen-1-yl)-3,7-dihydro-1H-purine-2,6-dione

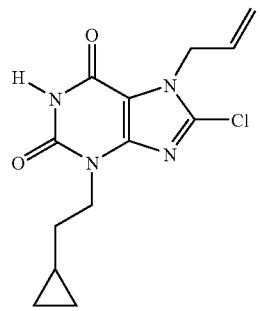

8-chloro-7-(2-propen-1-yl)-3,7-dihydro-1H-purine-2,6-dione (1.5 g, 6.64 mmol), sodium carbonate (844 mg, 7.9 mmol) and 2-cyclopropylethyl methanesulfonate (1.19 g, 7.3 mmol) were stirred in dimethylformamide (25 ml, dry) for two days at 80° C. The reaction mixture was partitioned between ethyl acetate and water. The organic phase was separated and washed with hydrochloric acid (2N), brine, dried (MgSO$_4$) and then evaporated to dryness. The crude product was triturated with ether and the solid collected by filtration to afford the title compound as a white solid (0.96 g, 49%). m/z 295 [MH$^+$].

b) 8-chloro-3-(2-cyclopropylethyl)-3,7-dihydro-1H-purine-2,6-dione

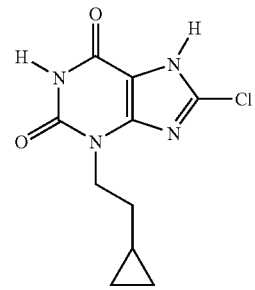

8-chloro-3-(2-cyclopropylethyl)-7-(2-propen-1-yl)-3,7-dihydro-1H-purine-2,6-dione (74 mg, 0.25 mmol) and morpholine (220 ul, 2.5 mmol) were degassed with nitrogen in tetrahydrofuran (3 ml) and then tetrakis(triphenylphosphine)palladium(0) (29 mg, 0.025 mmol) was added and the reaction stirred at room temperature overnight. The white precipitate was collected by filtration and washed with tetrahyrofuran and ether to afford the morpholine salt of the title compound (52 mg). This was treated with 2N HCl and methanol and the solvents evaporated to dryness before re-dissolving in DMSO/MeOH and purifying by preparative HPLC using a 10 to 40% gradient to give the title compound (22 mg, 34.6%).

NMR δ$_H$ (400 MHz, d$^4$-MeOD) 0.00-0.05 (m, 2H), 0.37-0.43 (m, 2H), 0.67-0.77 (m, 1H), 1.61 (q, 2H, J=7 Hz), 4.06-4.11 (m, 2H); m/z 255 [MH$^+$].

Example 10

3-butyl-8-chloro-3,7-dihydro-1H-purine-2,6-dione

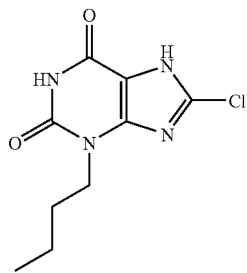

a) 3-butyl-8-chloro-7-(2-propen-1-yl)-3,7-dihydro-1H-purine-2,6-dione

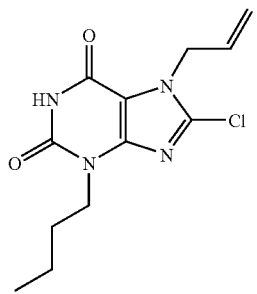

To a solution of 3-butyl-7-(2-propen-1-yl)-3,7-dihydro-1H-purine-2,6-dione (3.34 g, 13.4 mmol) in anhydrous DMF (19 ml) was added NCS (1.97 g, 14.8 mmol) and left to stir at rt under nitrogen for 22 hours. The mixture was concentrated in vacuo to give a yellow solid which was filtered and washed with methanol. The filtrate was concentrated and the process repeated. On the final wash the filtrate was purified by SPE (Si, 20 g) cartridge eluting with 1:1; EtOAc:cyclohexane. The combined solids were dried under vacuum to afford the title compound (2.42 g, 64%); m/z 283.3 [MH$^+$]

b) 3-butyl-8-chloro-3,7-dihydro-1H-purine-2,6-dione

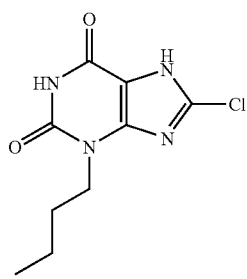

A solution of 3-butyl-8-chloro-7-(2-propen-1-yl)-3,7-dihydro-1H-purine-2,6-dione (100 mg, 0.35 mmol) in anhydrous THF (4 ml) and anhydrous DMSO (0.4 ml) was treated with Pd(PPh$_3$)$_4$ (61 mg, 0.053 mmol). The mixture was degassed under gentle vacuum, morpholine (308 uL, 3.5 mmol) was added, and left to stir at rt under nitrogen for 4 hours. The yellow 10 solution was partitioned between 2M HCl(aq) and EtOAc. The organic layer was separated, washed with brine, dried (MgSO$_4$) and concentrated. The residue was taken up in MeOH and passed down an amino-propyl SPE (5 g), eluting with MeOH followed by 5% AcOH/MeOH. The product fractions were combined and concentrated in vacuo to afford the title compound as an off white solid (30 mg, 35%). NMR; δ$_H$ (400 MHz, d$^6$-DMSO) 0.89 (t, 3H, J=7.5 Hz), 1.23-1.34 (m, 2H), 1.55-1.65 (m, 2H), 3.85 (t, 2H, J=7 Hz), 11.17 (s, 1H), 14.37 (br.s, 1H); m/z 243.3 [MH$^+$].

Example 11

8-Chloro-3-propyl-3,7-dihydro-1H-purine-2,6-dione

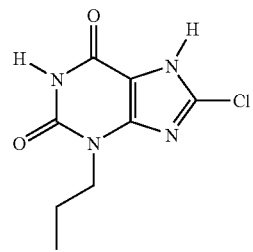

3-Propyl-3,7-dihydro-1H-purine-2,6-dione (J.Med.Chem, 1993, 36 (10), 1380-6) (0.3 g, 1.5 mmol) and N-chlorosuccinimide (0.21 g, 1.5 mmol) were dissolved in DMF (5 ml) and the solution stirred for 5 h. The solution was concentrated and the solid residues washed with methanol and filtered to provide the product as a white solid (0.148 g, 42%). NMR; δ$_H$ (400 MHz, d$^6$-DMSO) 0.85 (t, 3H, J=7 Hz), 1.65 (m, 2H), 3.8 (t, 2H, J=7 Hz), 11.2 (s, 1H), one exchangeable not observed to δ$_H$ 13; m/z 229[MH$^+$]

Example 12

8-chloro-3-pentyl-3,7-dihydro-1H-purine-2,6-dione

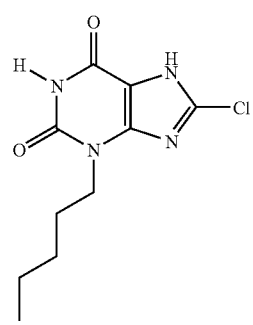

a) 8-chloro-3-pentyl-7-(2-propen-1-yl)-3,7-dihydro-1H-purine-2,6-dione

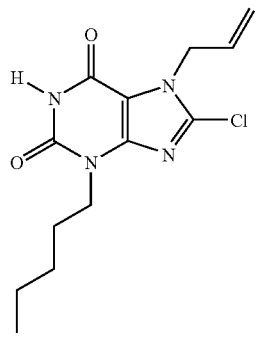

To a solution of 8-chloro-7-(2-propen-1-yl)-3,7-dihydro-1H-purine-2,6-dione (100 mg, 0.44 mmol) in anhydrous DMF (3 ml) was added sodium carbonate (0.051 g, 0.484 mmol). After 10 minutes stirring at room temperature pentyl iodide (0.063 ml, 0.484 mmol) was added and stirring continued under nitrogen at room temperature for 18 hours. The reaction mixture was diluted with water (25 ml) and extracted with EtOAc (2×25 ml). The combined organic extracts were dried (MgSO$_4$) filtered and evaporated. Purification by SPE (Si, 5 g) eluting with 4:1 EtOAc/cyclohexane afforded the title compound as a white solid (96 mg, 74%); m/z 297.2 [MH$^+$].

b) 8-chloro-3-pentyl-3,7-dihydro-1H-purine-2,6-dione

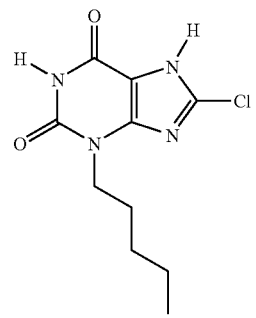

A flask containing tetrakis(triphenylphosphine)-palladium (0) (56 mg, 0.049 mmol) was flushed with nitrogen, before a solution of 8-chloro-3-pentyl-7-(2-propen-1-yl)-3,7-dihydro-1H-purine-2,6-dione (96 mg, 0.323 mmol) in anhydrous THF (1.5 ml) was added, followed by DMSO (0.1 ml) and morpholine (0.28 ml, 0.049 mmol). The resulting mixture was stirred at room temperature under nitrogen for 72 hours. The reaction mixture was dissolved in EtOAc (25 ml) and washed with 2M HCl aq. (25 ml). The organic extract was dried (MgSO$_4$) filtered and evaporated under reduced pressure. Purification by amino propyl SPE (2 g) loading and washing with methanol and then eluting the product with 5% acetic acid in methanol. Evaporation of fractions containing product afforded the title compound as a white solid (27 mg, 33%). NMR; $\delta_H$ (400 MHz, d$^6$-DMSO) 0.85 (t, 3H, J=7 Hz), 1.20-1.34 (m, 4H), 1.57-1.67 (m, 2H), 3.84 (t, 2H, J=7 Hz), 11.19 (s, 1H), 14.38 (br. s, 1H); m/z 257.2[MH$^+$].

Example 13

8-chloro-3-(3-methylbutyl)-3,7-dihydro-1H-purine-2,6-dione

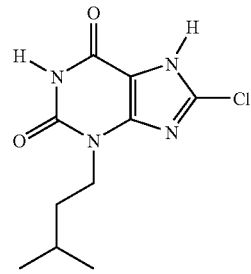

a) 8-chloro-3-(3-methylbutyl)-7-(2-propen-1-yl)-3,7-dihydro-1H-purine-2,6-dione

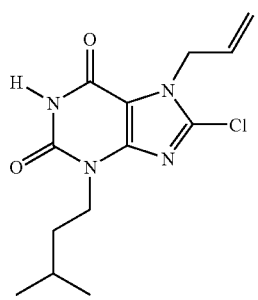

A solution of 8-chloro-7-(2-propen-1-yl)-3,7-dihydro-1H-purine-2,6-dione (1.5 g, 6.6 mmol) in DMF (40 ml) was treated with sodium carbonate (0.9 g, 8.5 mmol) and 1-bromo-3-methylbutane (1.04 g, 6.9 mmol). The stirred mixture was heated at 50° C. for 18 hours then cooled and evaporated to dryness. The residue was treated with water (60 ml) and extracted with ethyl acetate (3×80 ml). The organic fractions were combined, dried over magnesium sulfate, filtered and evaporated. The residue was triturated with a mixture of diethyl ether and cyclohexane to reveal the product as a white solid which was filtered off and dried. This gave the title compound as a white solid m/z 297[MH$^+$].

b) 8-chloro-3-(3-methylbutyl)-3,7-dihydro-1H-purine-2,6-dione

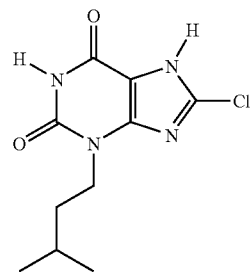

A solution of 8-chloro-3-(3-methylbutyl)-7-(2-propen-1-yl)-3,7-dihydro-1H-purine-2,6-dione (0.074 g, 0.25 mmol) in THF (2 ml) was treated with morpholine (0.035 ml, 4.0 mmol) and the mixture degassed by the repeated alternate application of vacuum and nitrogen to the reaction vessel. The mixture was then treated with a solution of tetrakis(triphenylphosphine)palladium(0) (0.03 g, 0.026 mmol) in degassed THF (0.5 ml). After 2 hours the mixture was treated with 2M aqueous hydrochloric acid (2 ml) and diethyl ether (3 ml). The precipitated product was filtered off, washed with diethyl ether and dried. This yielded the title compound as a white solid (0.036 g, 56%). NMR $\delta_H$ (400 MHz, d$^6$-DMSO); 0.91 (d, 6H, J=6.3 Hz), 1.47-1.62 (m, 3H), 3.87 (t, 2H, J=7.5 Hz), 11.19 (br. s, 1H), 14.83 (br. s, 1H); m/z 257, 259[MH$^+$].

Example 14

4-(8-chloro-2,6-dioxo-1,2,6,7-tetrahydro-3H-purin-3-yl)butanenitrile

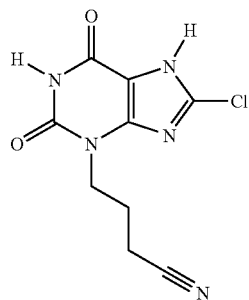

Prepared as example 13 using 4-bromobutyronitrile as alkylating agent
NMR $\delta_H$ (400 MHz, d$^6$-DMSO); 1.89-2.00 (m, 2H), 2.55 (t, 2H, J=7.0 Hz), 3.95 (t, 2H, J=6.5 Hz), 11.25 (br. s, 1H), 14.40 (br. s, 1H); m/z 254 [MH$^+$].

Example 15

8-chloro-3-(2-cyclohexylethyl)-3,7-dihydro-1H-purine-2,6-dione

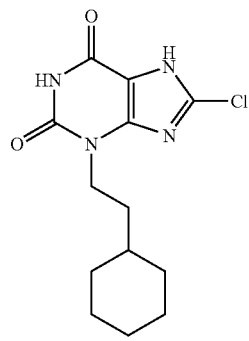

8-chloro-7-(2-propen-1-yl)-3,7-dihydro-1H-purine-2,6-dione (100 mg, 0.442 mmol) was stirred with sodium carbonate (52 mg, 0.486 mmol) in dry DMF (3 ml) for 30 min. Cyclohexylethyl bromide (93 mg, 0.486 mmol) was added, and the mixture was stirred at 37-40° C. under nitrogen for 65 h, followed by heating at 90° C. for 18 h. After cooling, the solution was degassed by evacuating and introducing nitrogen several times, and tetrakis(triphenylphosphine)palladium(0) (76 mg, 0.066 mmol) and morpholine (0.385 ml, 4.42 mmol) were added and the mixture stirred for 18 h. A further quantity of tetrakis(triphenylphosphine)palladium(0) (50 mg, 0.043 mmol) and morpholine (0.2 ml) were added and stirring continued for a further 1 h. Ethyl acetate and 2M aqueous HCl were added (ca. 10 ml each) and the organic layer separated, washed with brine and evaporated. The residue was dissolved in THF and loaded onto a 5 g aminopropyl SPE cartridge. The cartridge was washed with THF followed by MeOH, and the acidic product eluted with AcOH in MeOH (5% rising to 10%). The product thus obtained was further purified by autoprep HPLC to provide the title compound, 5.5 mg, 3%

NMR $\delta_H$ (400 MHz, d$^6$-DMSO) 0.80-0.95 (m, 2H), 1.05-1.35 (m, 4H), 1.45-1.55 (m, 2H), 1.55-1.70 (m, 3H), 1.70-1.80 (m, 2H), 3.86 (t, 2H, J=8 Hz), 11.07 (s, 1H), one exchangeable not observed. m/z 297 (MH$^+$), Example 16

3-butyl-1-methyl-2,6-dioxo-2,3,6,7-tetrahydro-1H-purine-8-carbonitrile

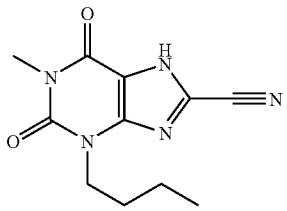

a) 3-butyl-7-(2-propen-1-yl)-3,7-dihydro-1H-purine-2,6-dione

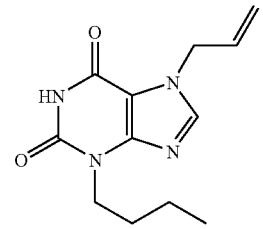

A stirred solution of 7-(2-propen-1-yl)-3,7-dihydro-1H-purine-2,6-dione (10 g, 52 mmol) in anhydrous DMF (100 ml) was treated with K$_2$CO$_3$ (7.91 g, 57.2 mmol) and, after 10 minutes, BuI (6.51 ml, 57.2 mmol). After reacting for 2 days the reaction mixture was partitioned between 2M HCl(aq) and EtOAc. The organic layer was separated, washed with brine, dried (MgSO$_4$) and concentrated in vacuo to give an off-white solid. This was washed with hot cyclohexane and dried under vacuum to give the title compound (8.87 g, 68%); m/z 249.3[MH$^+$].

b) 3-butyl-1-methyl-7-(2-propen-1-yl)-3,7-dihydro-1H-purine-2,6-dione

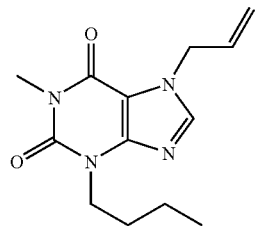

A stirred solution of 3-butyl-7-(2-propen-1-yl)-3,7-dihydro-1H-purine-2,6-dione (1.0 g, 4.03 mmol) in anhydrous DMF (10 ml) was treated with $Na_2CO_3$ (470 mg, 4.43 mmol) followed by Methyliodide (275 ul, 4.43 mmol). The mixture was heated at 35° C. for 17 hours. $K_2CO_3$ (500 mg, 3.6 mmol) and Methyliodide (275 ul, 4.43 mmol) were added and then stirred at 50° C. for a further 18 hours. The reaction mixture was allowed to cool then partitioned between 2M HCl(aq) and EtOAc. The organic layer was separated and the aqueous extracted once more with EtOAc. The combined extracts were washed with brine, dried ($MgSO_4$) and concentrated giving a yellow/brown oil (1.24 g). The product was purified by silica SPE (10 g), eluting with EtOAc/cyclohexane mixtures. The product fractions were combined and concentrated to afford the title compound as a pale yellow solid (1.11 g, quant.); m/z 263.3[MH$^+$].

c) 3-butyl-1-methyl-2,6-dioxo-7-(2-propen-1-yl)-2,3,6,7-tetrahydro-1H-purine-8-carbaldehyde

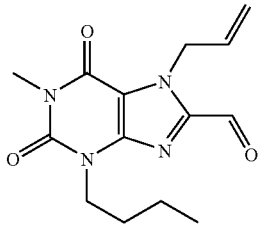

A pre-dried flask was charged with 3-butyl-1-methyl-7-(2-propen-1-yl)-3,7-dihydro-1H-purine-2,6-dione (300 mg, 1.14 mmol) and anhydrous THF (6 ml), cooled to −75° C. under nitrogen, then treated with LiHMDS (1.37 ml of a 1.0M solution in THF). The resulting solution was allowed to warm to −60° C. over 1.5 hours before the addition of anhydrous DMF (177 ul, 2.29 mmol). The solution was allowed to warm to −10° C. over 3 hours then it was quenched with sat. NH$_4$Cl (aq) solution. The mixture was partitioned between 1M HCl (aq) and EtOAc. The organic layer was separated, washed with brine, dried (MgSO$_4$) and concentrated giving a brown oil (350 mg). The product was purified by SPE (Si, 10 g) eluting with EtOAc/cyclohexane mixtures to give the title compound as a white solid (131 mg, 39%); NMR; $\delta_H$ (400 MHz, d$^6$-DMSO) 0.91 (t, 3H, J=7.5 Hz), 1.28-1.39 (m, 2H), 1.63-1.73 (m, 2H), 3.25 (s, 3H), 4.02 (t, 2H, J=7.5 Hz), 5.03 (dd, 1H, J=17 and 1 Hz), 5.17 (dd, 1H, J=10 and 1 Hz), 5.31 (app. d, 2H, J=5.5 Hz), 5.98-6.09 (m, 1H), 9.88 (s, 1H).

d) 3-butyl-1-methyl-2,6-dioxo-7-(2-propen-1-yl)-2,3,6,7-tetrahydro-1H-purine-8-carbonitrile

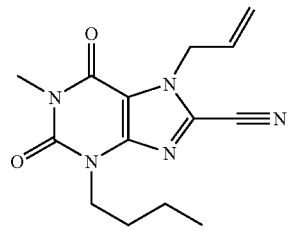

A solution of 3-butyl-1-methyl-2,6-dioxo-7-(2-propen-1-yl)-2,3,6,7-tetrahydro-1H-purine-8-carbaldehyde in anhydrous pyridine (5 ml) was treated with hydroxylamine hydrochloride (63 mg, 0.91 mmol) and heated at 50° C. for 1 hour. The mixture was allowed to cool, concentrated, and treated with acetic anhydride (5 ml) then heated at 100° C. for 2.5 hours and 125° C. for 45 minutes. Again the mixture was allowed to cool then partitioned between water and EtOAc. The organic layer was separated, washed with brine, dried (MgSO$_4$) and concentrated to afford the title compound as a yellow residue (230 mg crude, 114%); m/z 288.3[MH$^+$].

e) 3-butyl-1-methyl-2,6-dioxo-2,3,6,7-tetrahydro-1H-purine-8-carbonitrile

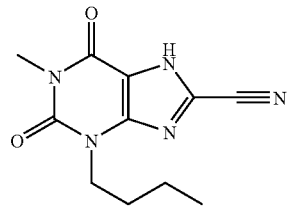

A solution of 3-butyl-1-methyl-2,6-dioxo-7-(2-propen-1-yl)-2,3,6,7-tetrahydro-1H-purine-8-carbonitrile (230 mg, 0.80 mmol) in anhydrous THF (5 ml) and anhydrous DMSO (0.5 ml) was treated with Pd(PPh$_3$)$_4$ (185 mg, 0.16 mmol). The mixture was degassed under gentle vacuum, morpholine (698 uL) added, and left to stir at rt under nitrogen for 2 hours. The yellow solution was partitioned between 2M HCl(aq) and EtOAc. The organic layer was separated, washed with brine, dried (MgSO$_4$) and concentrated. The residue was taken up in MeOH and passed down and amino-propyl SPE (5 g), eluting with MeOH followed by 5% AcOH then 10%, 20% and 30% AcOH/MeOH mixtures. The product fractions were combined and concentrated to afford a pale yellow solid (116 mg). This was washed with MeOH and the title compound a white solid was collected by filtration and dried under vacuum (55 mg, 28%). NMR; $\delta_H$ (400 MHz, d$^6$-DMSO) 0.90 (t, 3H, J=7.5 Hz), 1.25-1.35 (m, 2H), 1.59-1.68 (m, 2H), 3.24 (s, 3H), 3.96 (t, 2H, J=7 Hz), NH not observed to $\delta_H$ 15; m/z 248.2[MH$^+$].

Example 17

1-Methyl-2,6-dioxo-3-pentyl-2,3,6,7-tetrahydro-1H-purine-8-carbonitrile

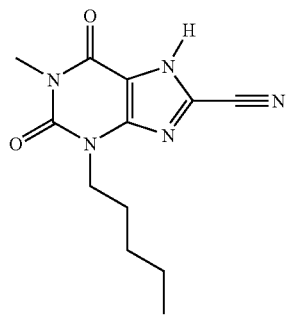

a) 3-Pentyl-7-(2-propen-1-yl)-3,7-dihydro-1H-purine-2,6-dione

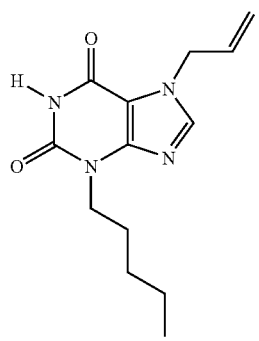

7-(2-propen-1-yl)-3,7-dihydro-1H-purine-2,6-dione (0.61 g, 3.2 mmol), sodium carbonate (0.60 g, 5.7 mmol) and pentyl iodide (0.64 g, 3.2 mmol) were stirred in DMF (5 ml) at 50° C. for 18 h. The solution was cooled, separated between ethyl acetate and brine and the organics isolated, dried (MgSO$_4$) and concentrated. Chromatography over silica (gradient elution dichloromethane to 5:1 dichloromethane/ethyl acetate) provided the title compound as a pale yellow solid (0.47 g, 56%). m/z 263[MH$^+$]

b) 1-methyl-3-pentyl-7-(2-propen-1-yl)-3,7-dihydro-1H-purine-2,6-dione

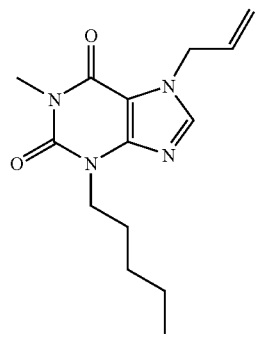

3-Pentyl-7-(2-propen-1-yl)-3,7-dihydro-1H-purine-2,6-dione (0.20 g, 0.76 mmol), potassium carbonate (0.4 g, 2.9 mmol) and methyl iodide (0.5 ml, 4.9 mmol) were stirred and heated at 50° C. in DMF (5 ml) for 3 h. The solution was allowed to cool and separated between ethyl acetate and brine. The organics were isolated, dried (MgSO$_4$) and concentrated to provide the title compound (0.21 g, 100%). m/z 277[MH$^+$]

c) 1-Methyl-2,6-dioxo-3-pentyl-7-(2-propen-1-yl)-2,3,6,7-tetrahydro-1H-purine-8-carbaldehyde

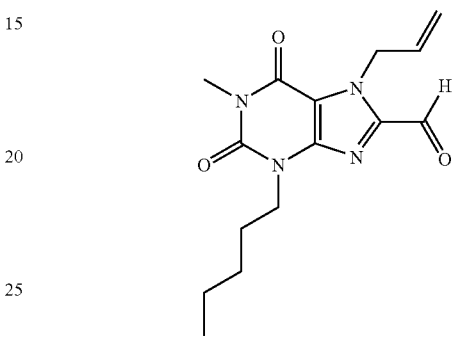

To 1-methyl-3-pentyl-7-(2-propen-1-yl)-3,7-dihydro-1H-purine-2,6-dione (1.05 g, 3.6 mmol) in THF (15 ml) at −78° C. was added LiHMDS (4 ml, 1M in hexane, 4 mmol) over 10 min and the solution stirred for 0.5 h. DMF (0.5 ml) was added and the solution stirred at −78° C. for a further 0.5 h then allowed to warm to ambient temperature with the cooling bath over 2 h. The reaction was quenched with 2N hydrochloric acid (3 ml) and partioned between ethyl acetate and brine. The organics were isolated, dried and concentrated. The crude product was chomatographed over silica (gradient elution dichloromethane to 5:1 dichloromethane/ethyl acetate) to afford the title compound as a white solid (0.35 g, 30%). m/z 305[MH$^+$]

d) 1-Methyl-2,6-dioxo-3-pentyl-7-(2-propen-1-yl)-2,3,6,7-tetrahydro-1H-purine-8-carbonitrile

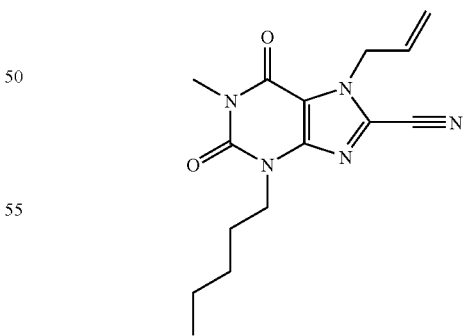

1-Methyl-2,6-dioxo-3-pentyl-7-(2-propen-1-yl)-2,3,6,7-tetrahydro-1H-purine-8-carbaldehyde (0.18 g, 0.6 mmol) and hydroxylamine hydrochloride (0.053 g, 0.76 mmol) were heated at 50° C. in pyridine (5 ml) for 1 h then cooled to ambient. Acetic anhydride (0.08 g, 0.78 mmol) was added and the solution stirred for 18 h. The solution was concentrated to provide the acetate and dissolved in acetic anhydride (3 ml) and heated to 130° C. for 3 h, cooled and concentrated to yield crude product. Chromatography over silica (eluting with dichloromethane) yielded the title compound as a clear oil (0.17 g, 95%). m/z 302[MH$^+$]

e) 1-Methyl-2,6-dioxo-3-pentyl-2,3,6,7-tetrahydro-1H-purine-8-carbonitrile

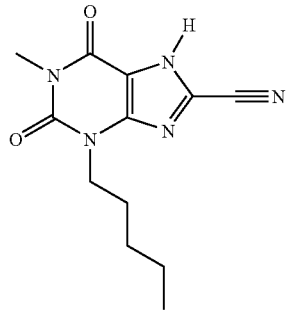

1-Methyl-2,6-dioxo-3-pentyl-7-(2-propen-1-yl)-2,3,6,7-tetrahydro-1H-purine-8-carbonitrile (0.17 g, 0.56 mmol) and morpholine (0.6 ml, 6.7 mmol) were dissolved in THF (5 ml) containing DMSO (0.5 ml). The flask containing the solution was placed under vacuum and the air replaced with nitrogen (x3). Tetrakis(triphenylphosphine)palladium (0) (0.13 g, 0.11 mmol) was added and the solution stirred for 2.5 h. The solution was separated between ethyl acetate (20 ml) and 2N hydrochloric acid (10 ml) and the organics isolated and washed with brine (3×10 ml). The organics were then washed with 2N sodium hydroxide solution (2×10 ml) and the aqueous acidified with 2N hydrochloric acid and extracted with ethyl acetate (2×10 ml). The organics were isolated, dried (MgSO$_4$) and concentrated to yield the title compound (0.026 g, 18%). NMR; δ$_H$ (400 MHz, CDCl$_3$) 0.92 (t, 3H, J=7 Hz), 1.32-1.43 (m, 4H), 1.79 (m, 2H), 3.54 (s, 3H), 4.15 (t, 2H, J=7.5 Hz,), 14.35 (br. s, 1H); m/z 262[MH$^+$]

Example 18

8-chloro-3-hexyl-1-methyl-3,7-dihydro-1H-purine-2,6-dione

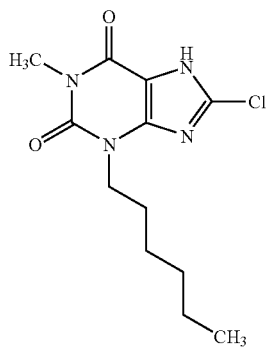

a) 8-chloro-3-({[2-(methyloxy)ethyl]oxy}methyl)-7-(2-propen-1-yl)-3,7-dihydro-1H-purine-2,6-dione

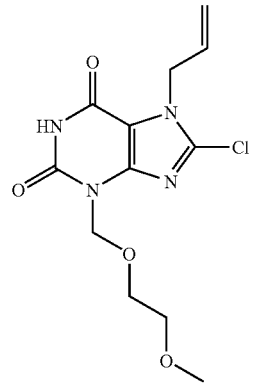

To a solution of 8-chloro-7-(2-propen-1-yl)-3,7-dihydro-1H-purine-2,6-dione (6 g, 26.5 mmol) in anhydrous DMF (30 ml) was added sodium carbonate (3.09 g, 29.15 mmol). After 10 minutes stirring at room temperature methoxyethoxymethylchloride (3.03 ml, 26.5 mmol) was added and stirring continued under nitrogen at room temperature for 66 hours. The reaction mixture was concentrated in vacuo and the residue dissolved in EtOAc (100 ml) and washed with brine (100 ml), the aqueous extract was extracted with DCM (100 ml) and the organic extracts dried (MgSO$_4$) combined and concentrated in vacuo. The residue was triturated with EtOAc and the solid filtered off. Concentration of the filtrate afforded a light brown oil that was absorbed onto silica and purified by SPE (Si, 50 g) eluting with a gradient of 1:1 EtOAc/cyclohexane-EtOAc to afford the title compound as a white solid (2 g, 24%), m/z 315.2[MH$^+$].

b) 8-chloro-1-methyl-3-({[2-(methyloxy)ethyl]oxy}methyl)-7-(2-propen-1-yl)-3,7-dihydro-1H-purine-2,6-dione

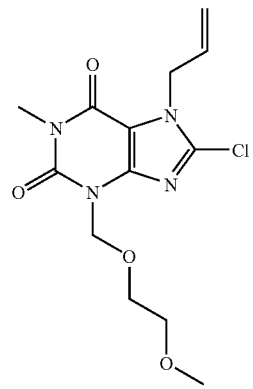

To a solution of 8-chloro-3-({[2-(methyloxy)ethyl]oxy}methyl)-7-(2-propen-1-yl)-3,7-dihydro-1H-purine-2,6-dione (2 g, 6.37 mmol) in anhydrous DMF (15 ml) was added sodium carbonate (0.743 g, 7 mmol). After 10 minutes stirring at room temperature methyliodide (0.44 ml, 7 mmol) was added and stirring continued under nitrogen at room temperature for 18 hours. The reaction mixture was concentrated in c) 8-chloro-1-methyl-7-(2-propen-1-yl)-3,7-dihydro-1H-purine-2,6-dione

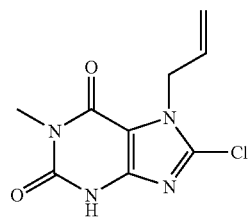

To a solution of 8-chloro-1-methyl-3-({[2-(methyloxy)ethyl]oxy}methyl)-7-(2-propen-1-yl)-3,7-dihydro-1H-purine-2,6-dione (2.9 g, 6.37 mmol) in dioxan (20 ml) and water (20 ml) was added 5M HCl (20 ml). The resulting mixture was heated at 100° C. under nitrogen for 18 hours. The reaction mixture was then concentrated in vacuo, the residue was dissolved in EtOAc (100 ml) and washed with water. The organic extract was dried (MgSO$_4$) filtered and evaporated. Purification by SPE (Si, 20 g) eluting 2:3 EtOAc/cyclohexane afforded the title compound as a white solid (1.04 g, 68%). m/z 241.1[MH$^+$].

Alternatively 8-chloro-1-methyl-7-(2-propen-1-yl)-3,7-dihydro-1H-purine-2,6-dione can be prepared with SEM protection.

a) 8-chloro-7-(2-propen-1-yl)-3-({[2-(trimethylsilyl)ethyl]oxy}methyl)-3,7-dihydro-1H-purine-2,6-dione

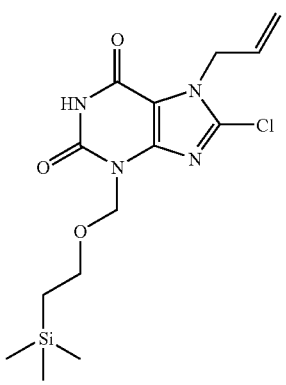

To a solution of 8-chloro-7-(2-propen-1-yl)-3,7-dihydro-1H-purine-2,6-dione (5 g, 22.1 mmol) in DMF (80 ml) was added 2-2-(trimethylsilyl)ethoxymethyl chloride (4.3 ml, 24.2 mmol) and sodium carbonate ( 2.6 g, 24.2 mmol). After stirring overnight at room temperature overnight further 2-2-(trimethylsilyl)ethoxymethyl chloride (4.3 ml, 24.2 mmol) and sodium carbonate (1.3 g, 12.1 mmol) were added and stirring continued for 2 hours. The reaction mixture was then partitioned between 5% LiCl aq and ethylacetate. The organic extract was separated, washed with brine, dried (MgSO$_4$) and concentrated. Purification by Biotage™ chromatogratphy using a silica cartridge eluting 1:4-1:2 ethyl acetate/cyclohexante afforded the title compound (3.14 g, 40%); m/z 374.2 [MNH$_4^+$].

b) 8-chloro-1-methyl-7-(2-propen-1-yl)-3-({[2-(trimethylsilyl)ethyl]oxy}methyl)-3,7-dihydro-1H-purine-2,6-dione

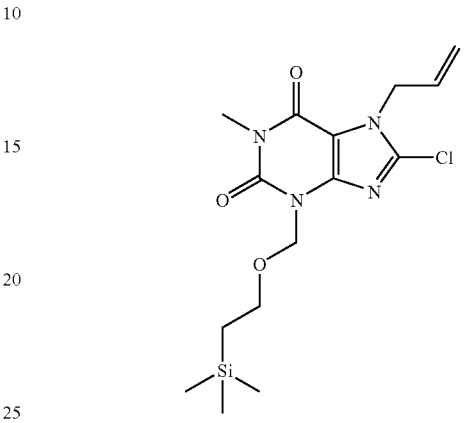

To a solution of 8-chloro-7-(2-propen-1-yl)-3-({[2-(trimethylsilyl)ethyl]oxy}methyl)-3,7-dihydro-1H-purine-2,6-dione (3.14 g, 8.82 mmol) in DMF (50 ml) was added methyl iodide (0.659 ml, 10.58 mmol) and caesium carbonate (3.45 g, 10.58 mmol) and the reaction mixture stirred overnight at room temperature. The reaction mixture was partioned between water and ethyl acetate. The organic extract was separated, washed with brine, dried (MgSO$_4$) and concentrated to afford the title compound 2.99 g (92%); m/z 388 [MNH$_4^+$].

c) 8-chloro-1-methyl-7-(2-propen-1-yl)-3,7-dihydro-1H-purine-2,6-dione

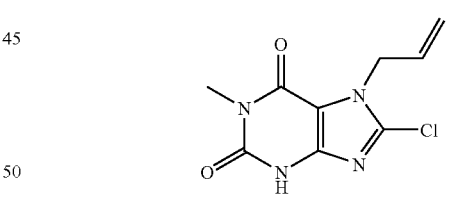

To a solution of 8-chloro-1-methyl-7-(2-propen-1-yl)-3-({[2-(trimethylsilyl)ethyl]oxy}methyl)-3,7-dihydro-1H-purine-2,6-dione (2.99 g, 8.08 mmol) in DCM (20 ml) was added TFA (10 ml) and the reaction stirred for 2.5 hours at room temperature. The reaction mixture was then concentrated and the residue treated with further DCM and evaporated once more. Purification by SPE (Si) eluting 1:9-4:1 ethylacetate/cyclohexane afforded impure product (1.31 g), which was dissolved in methanol (20 ml) and treated with sat. potassium carbonate aq. (20 ml). After stirring overnight the mixture was partitioned between water containing 2M HCl (1 ml) and ethyl acetate. The organic extract was separated, washed with brine, dried (MgSO$_4$) and concentrated to afford the title compound 0.87 g (45%); m/z 241.1 [MH$^+$].

d) 8-chloro-3-hexyl-1-methyl-3,7-dihydro-1H-purine-2,6-dione

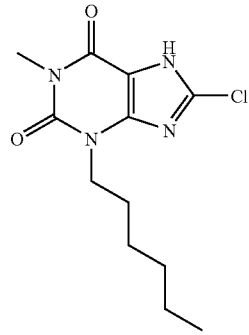

To a solution of 8-chloro-1-methyl-7-(2-propen-1-yl)-3,7-dihydro-1H-purine-2,6-dione (100 mg, 0.42 mmol) in anhydrous DMF (3 ml) was added sodium carbonate (58 mg, 0.54 mmol), after 10 minutes stirring hexyl iodide (0.08 ml, 0.54 mmol) was added and the reaction mixture stirred at room temperature under nitrogen for 90 hours. Pd(PPh$_3$)$_4$ (73 mg, 0.063 mmol) was then added and the reaction vessel evacuated and flushed with nitrogen (x3), morpholine (0.37 ml, 4.3 mmol) was added and stirring at room temperature under nitrogen continued for 4 hours. The reaction mixture was diluted with EtOAc (25 ml) and washed with 2M HCl aq. (25 ml). The organic extract was dried (MgSO$_4$) filtered and evaporated. Purification by aminopropyl SPE (5 g) loading the compound and washing with MeOH before eluting the product with 5% AcOH/MeOH afforded the title compound as a white solid (65 mg, 54%). NMR; $\delta_H$ (400 MHz, d$^6$-DMSO) ) 0.85 (t, 3H, J=7 Hz), 1.23-1.33 (m, 6H), 1.58-1.68 (m, 2H), 3.22 (s, 3H), 3.91 (t, 2H, J=7.5 Hz), 14.46 (br. s, 1H); m/z 285.3 [MH$^+$].

Example 19

8-chloro-1-methyl-3-propyl-3,7-dihydro-1H-purine-2,6-dione

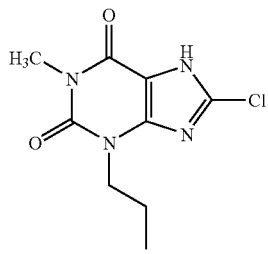

Prepared in similar fashion to Example 18 but using propyl iodide to alkylate on N3.

NMR $\delta_H$ (400 MHz, d$^6$-DMSO) 0.87 (t, 3H, J=7.5 Hz), 1.61-1.73 (m, 2H), 3.22 (s, 3H), 3.89 (t, 2H, J=7.5 Hz), 14.45 (br. s, 1H), m/z 243 [MH$^+$]

Example 20

1,3-dibutyl-2,6-dioxo-2,3,6,7-tetrahydro-1H-purine-8-carbonitrile

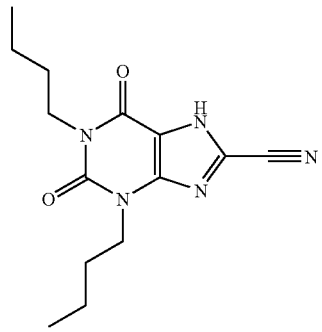

a) 1,3-dibutyl-7-(2-propen-1-yl)-3,7-dihydro-1H-purine-2,6-dione

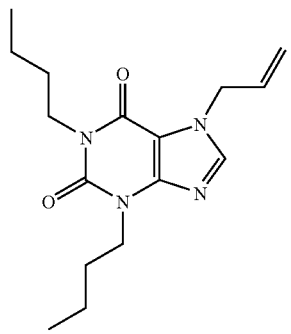

A solution of 1,3-di-N-butyl xanthine (10 g, 38 mmol) in anhydrous DMF (80 ml) was treated with K$_2$CO$_3$ (5.2 g, 38 mmol) followed by allyl bromide (3.6 ml, 42 mmol). The mixture was heated at 55° C. under nitrogen for 18 hours. After cooling to rt the mixture was partitioned between water and EtOAc. A few mls of 2M HCl(aq) was added to aid separation. The organic layer was separated and the aqueous extracted once more with EtOAc. The combined extracts were washed with brine, dried (MgSO$_4$) and concentrated to afford the title compound as an off-white solid (12.23 g, 106%). m/z 305.3[MH$^+$].

b) Methyl 1,3-dibutyl-2,6-dioxo-7-(2-propen-1-yl)-2,3,6,7-tetrahydro-1H-purine-8-carboxylate

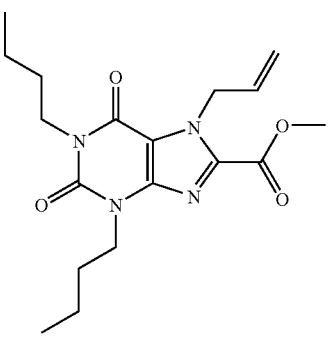

A solution of 1,3-dibutyl-7-(2-propen-1-yl)-3,7-dihydro-1H-purine-2,6-dione (3.0 g, 9.9 mmol) in anhydrous THF (30 ml) was cooled to −50° C. and treated with LiHMDS (18 ml of a 1.0M solution in THF, 17.8 mmol). After 1 hour at −50° C. methyl chloroformate (1.9 ml, 24.6 mmol) was added and the mixture allowed to warm to −30° C. over 2 hours, then quenched with sat. NH$_4$Cl (aq) solution. The mixture was partitioned between EtOAc and 1M HCl (aq). The organic layer was separated, washed with brine, dried (MgSO$_4$) and concentrated giving a dark orange oil (4.07 g). The oil was taken up in 15% EtOAc/cyclohexane and passed down a Si Biotage™ chromatography column. The product fractions were combined and concentrated to afford the title compound as a yellow solid (1.35 g, 38%). m/z 363.2 [MH$^+$].

c) 1,3-dibutyl-2,6-dioxo-7-(2-propen-1-yl)-2,3,6,7-tetrahydro-1H-purine-8-carboxylic acid

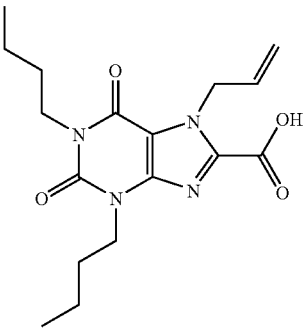

A stirred solution of methyl 1,3-dibutyl-2,6-dioxo-7-(2-propen-1-yl)-2,3,6,7-tetrahydro-1H-purine-8-carboxylate (1.30 g, 3.6 mmol) in MeOH (15 ml) was treated with LiOH (215 mg) and water (1.5 ml). After 3 hours at rt the mixture was diluted with water and the pH adjusted to ca. pH5 with 2M HCl(aq). EtOAc was added and then separated, washed with brine, dried (MgSO$_4$) and concentrated to afford the title compound as a yellow solid 85% pure (1.2 g, 88%). m/z. 349.2[MH$^+$].

d) 1,3-dibutyl-2,6-dioxo-7-(2-propen-1-yl)-2,3,6,7-tetrahydro-1H-purine-8-carboxamide

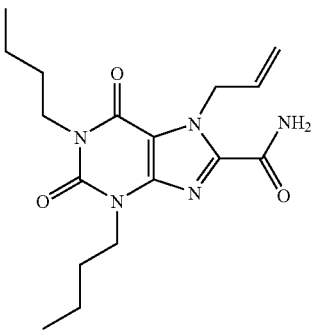

A stirred solution of 1,3-dibutyl-2,6-dioxo-7-(2-propen-1-yl)-2,3,6,7-tetrahydro-1H-purine-8-carboxylic acid (1.0 g, 2.9 mmol) in anhydrous DMF (10 ml) was sequentially treated with DIPEA (1.1 ml), PyBOP, and 2M NH$_3$ (3.6 ml). After 2 hours the product mixture was partitioned between 2M HCl(aq) and EtOAc. The organic layer was separated, washed with sat. NaHCO$_3$(aq) solution, brine, then dried (MgSO$_4$) and concentrated giving an orange oil (ca. 2 g). The product was purified by Biotage™ chromatography eluting with 5%→40% EtOAc/cyclohexane mixtures. The appropriate fractions were combined and concentrated to give the amide 90% pure (790 mg, 78%). m/z. 392.3[M+formic acid−H]$^-$.

e) 1,3-dibutyl-2,6-dioxo-7-(2-propen-1-yl)-2,3,6,7-tetrahydro-1H-purine-8-carbonitrile

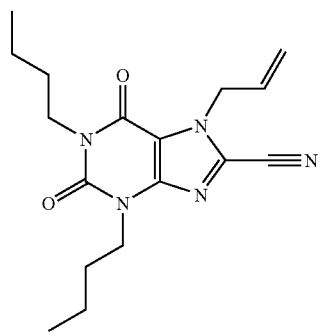

A solution of 1,3-dibutyl-2,6-dioxo-7-(2-propen-1-yl)-2,3,6,7-tetrahydro-1H-purine-8-carboxamide (300 mg) in anhydrous DMF (7 ml) at 0° C. was treated dropwise with POCl$_3$ (237 uL). The ice-bath was removed and after 2 hours the mixture was partitioned between water and Et$_2$O. The aqueous layer was re-extracted with Et$_2$O and the combined extracts separated, washed with water (x2), brine, then dried (MgSO$_4$) and concentrated, giving a yellow oil (312 mg). The oil was taken up in cyclohexane and purified by SPE (Si, 10 g) eluting with EtOAc/cyclohexane mixtures. Concentration of the product fractions gave the title compound as a colourless oil (150 mg, 53%). m/z. 330.3[MH$^+$].

f) 1,3-dibutyl-2,6-dioxo-2,3,6,7-tetrahydro-1H-purine-8-carbonitrile

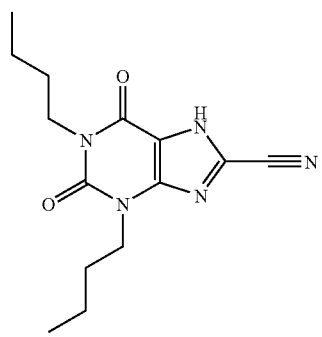

A solution of 1,3-dibutyl-2,6-dioxo-7-(2-propen-1-yl)-2,3,6,7-tetrahydro-1H-purine-8-carbonitrile (140 mg, 0.43 mmol) in anhydrous THF (4 ml) and anhydrous DMSO (0.4 ml) was treated with Pd(PPh$_3$)$_4$ (74 mg, 0.064 mmol). The mixture was degassed under gentle vacuum, morpholine (371 uL) added, and left to stir at rt under nitrogen for 4 hours.

The yellow solution was partitioned between 2M HCl(aq) and EtOAc. The organic layer was separated, washed with brine, dried (MgSO₄) and concentrated. The residue was taken up in MeOH and passed down and amino-propyl SPE (5 g), eluting with MeOH followed by 5%→50% AcOH/MeOH. The product eluted with a small impurity which was washed out, after concentrating, with cyclohexane to afford the title compound as an off-white solid (30 mg, 24%). NMR $\delta_H$ (400 MHz, d⁶-DMSO) 0.89 (app. td, 6H, J=7 and 3 Hz), 1.25-1.35 (m, 4H), 12.48-1.55 (m, 2H), 1.58-1.69 (m, 2H), 3.87 (t, 2H, J=7 Hz), 3.95 (t, 2H, J=7 Hz), NH not observed to $\delta_H$ 15; m/z 290.3[MH⁺].

Example 21

1,3-dibutyl-8-iodo-3,7-dihydro-1H-purine-2,6-dione

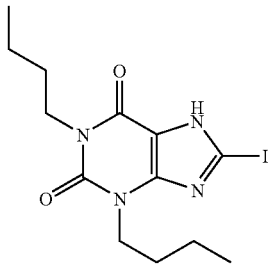

A stirred solution of 1,3-di-N-butyl xanthine (100 mg, 3.39 mmol) in anhydrous DMF (3 ml) was treated with NIS (94 mg, 3.75 mmol) and left to stir at rt. under nitrogen for 23 hours. The mixture was partitioned between sat. Na₂SO₃(aq) solution and EtOAc. The organic layer was separated, washed with brine, dried (MgSO₄) and concentrated in vacuo. The product was purified by passing down an SPE (Si, 5 g) cartridge eluting with EtOAc/cyclohexane mixtures. The product fraction was concentrated to afford the title compound as a white solid (75 mg, 51%); NMR; $\delta_H$ (400 MHz, d⁶-DMSO) (app.td, 6H, J=7.5 and 4 Hz), 1.21-1.34 (m, 4H), 1.45-1.54 (m, 2H), 1.56-1.66 (m, 2H), 3.84 (t, 2H, J=7.5 Hz), 3.93 (t, 2H, J=7.5 Hz), 14.10 (s, 1H); m/z 391.3[MH⁺].

Example 22

(3-butyl-8-chloro-2,6-dioxo-2,3,6,7-tetrahydro-1H-purin-1-yl)acetonitrile

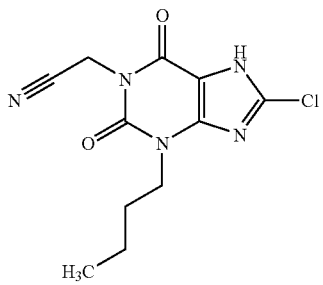

To a mixture of 3-butyl-8-chloro-7-(2-propen-1-yl)-3,7-dihydro-1H-purine-2,6-dione (200 mg, 0.707 mmol) and Cs₂CO₃ (254 mg, 0.778 mmol) in anhydrous DMF (5 ml) was added chloroacetonitrile (0.054 ml, 0.85 mmol). The mixture was heated at 50° C. for 18 hours then allowed to cool to rt and degassed under a gentle vacuum then nitrogen introduced. This was repeated twice. Pd(PPh₃)₄ (82 mg, 0.071 mmol) was added and the mixture degassed once more, before morpholine (0.617 ml, 7.07 mmol) was added and the mixture left to stir for 3 hours at rt. The mixture was partitioned between 2M HCl(aq) and EtOAc. The organic layer was separated, washed with brine, dried (MgSO₄) and concentrated. The residue was taken up in MeOH and passed down an amino-propyl SPE (5 g), eluting with MeOH followed by 5-10% AcOH/MeOH. The product fraction was concentrated giving the title compound 52 mg (26%); NMR; $\delta_H$ (400 MHz, d⁶-DMSO) 0.90 (t, 3H, J=7.5 Hz), 1.26-1.37 (m, 2H), 1.60-1.69 (m, 2H), 3.94 (t, 2H, J=7.5 Hz), 4.87 (s, 2H), 14.72 (br s, 1H); m/z 299.2 [MNH₄⁺].

Example 23

(8-chloro-2,6-dioxo-3-propyl-2,3,6,7-tetrahydro-1H-purin-1-yl)acetonitrile

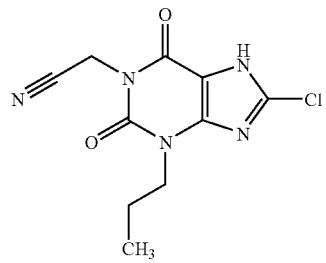

a) 8-chloro-7-(2-propen-1-yl)-3-propyl-3,7-dihydro-1H-purine-2,6-dione

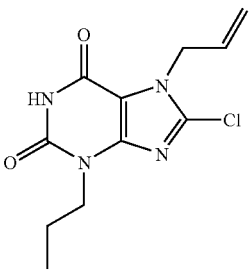

A mixture of 8-chloro-7-(2-propen-1-yl)-3,7-dihydro-1H-purine-2,6-dione (1.5 g, 6.6 mmol), 1-iodopropane (1.2 g, 6.9 mmol) and sodium carbonate (0.9 g, 8.5 mmol) in DMF (40 ml) was heated at 50° C. for 18 hours. The reaction mixture was concentrated in vacuo and the residue treated with water (60 ml) and extracted with ethyl acetate (3×80 ml). The combined organic extracts were dried (MgSO₄) filtered and evaporated. The residue was triturated with ether/cyclohexane, the solid was filtered off and dried to afford the title compound (0.82 g, 46%); m/z 269.1 [MH⁺].

b) (8-chloro-2,6-dioxo-3-propyl-2,3,6,7-tetrahydro-1H-purin-1-yl)acetonitrile

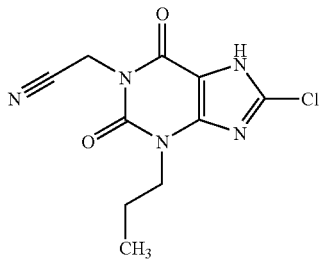

A solution of 8-chloro-7-(2-propen-1-yl)-3-propyl-3,7-dihydro-1H-purine-2,6-dione (0.067 g, 0.25 mmol) in DMF (2 ml) was treated with caesium carbonate (0.082 g, 0.25 mmol) and bromoacetonitrile (0.044 g, 0.37 mmol). The mixture was heated at 80° C. for 4 hours then cooled to ambient temperature. The DMF was removed in vacuo and the residue treated with THF (2 ml). The solvent was degassed by the successive application of vacuum and nitrogen pressure to the reaction mixture. The mixture was then treated with morpholine (0.035 ml, 0.4 mmol) and tetrakis(triphenylphosphine)palladium(0) (0.03 g, 0.026 mmol). After 2 hours the mixture was treated with 2M aqueous hydrochloric acid (2 ml) and the product extracted with chloroform (3×5 ml). The organic fractions were combined and evaporated. The residue was subjected to purification by mass-directed HPLC to afford the title compound as a white solid (0.022 g, 33%). NMR; $\delta_H$ (400 MHz, d$^6$-DMSO), 0.88 (t, 3H, J=7.5 Hz), 1.63-1.74 (m, 2H), 3.91 (t, 2H, J=7.5 Hz), 4.87 (s, 2H), NH not observed to $\delta_H$ 14; m/z 268 [MH$^+$].

Example 24

[8-chloro-3-(2-cyclopropylethyl)-2,6-dioxo-2,3,6,7-tetrahydro-1H-purin-1-yl]acetonitrile

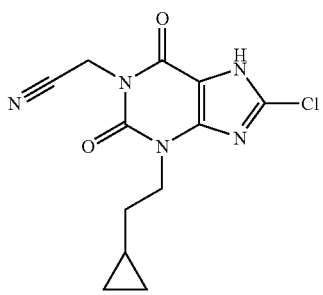

Prepared as (8-chloro-2,6-dioxo-3-propyl-2,3,6,7-tetrahydro-1H-purin-1-yl)acetonitrile (example 23) using 8-chloro-3-(2-cyclopropylethyl)-7-(2-propen-1-yl)-3,7-dihydro-1H-purine-2,6-dione.

NMR $\delta_H$ (400 MHz, d$^6$-DMSO) −0.06-0.00 (m, 2H), 0.31-0.39 (m, 2H), 0.64-0.74 (m, 1H), 1.57 (q, 2H, J=7 Hz), 4.04 (t, 2H, J=7 Hz), 4.87 (s, 2H), 14.68 (br. s, 1H); m/z 294 [MH$^+$].

Example 25

8-chloro-1-ethyl-3-(2,2,2-trifluoroethyl)-3,7-dihydro-1H-purine-2,6-dione

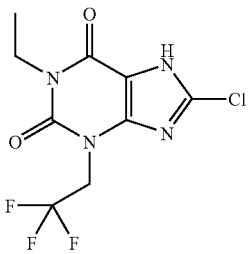

a) 8-chloro-7-(2-propen-1-yl)-3-(2,2,2-trifluoroethyl)-3,7-dihydro-1H-purine-2,6-dione

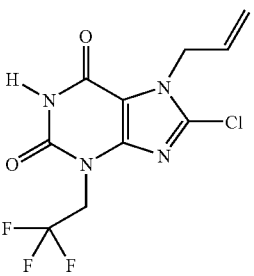

To a solution of 8-chloro-7-(2-propen-1-yl)-3,7-dihydro-1H-purine-2,6-dione (1.5 g, 6.62 mmol) in anhydrous DMF (50 ml) was added sodium bicarbonate (0.98 g, 9.25 mmol) followed by 1,1,1-trifluoro-2-iodoethane (1.20 g, 5.72 mmol) and the mixture heated with stirring for 6 h at 50° C. under an atmosphere of nitrogen. The solution was allowed to cool to ambient temperature for 10 h then heated for 48 h at 120° C. Additional 1,1,1-trifluoro-2-iodoethane (0.43 g, 2.05 mmol) was added and the mixture heated to 120° C. for a further 3 h. The solvent was removed under reduced pressure and the residue triturated with DCM then filtered.

The reaction was repeated using 8-chloro-7-(2-propen-1-yl)-3,7-dihydro-1H-purine-2,6-dione (3.80 g, 16.8 mmol), sodium bicarbonate (2.45 g, 23.1 mmol) and 1,1,1-trifluoro-2-iodoethane (4.05 g, 19.3 mmol) in anhydrous DMF (125 ml). The mixture was heated for 16 h at 120° C., the solvent removed under reduced pressure and the residue triturated with DCM then filtered.

DCM filtrates from the two runs were combined, concentrated under reduced pressure then purified using Biotage™ chromatography (eluting with cyclohexane/ethyl acetate 1:1, then 7:3) to give the title compound as a white solid (1.6 g, 23%). m/z 309 [MH$^+$].

b) 8-chloro-1-ethyl-3-(2,2,2-trifluoroethyl)-3,7-dihydro-1H-purine-2,6-dione

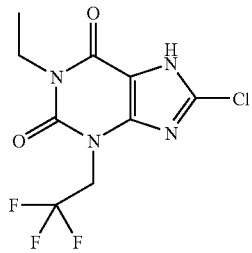

To a solution of 8-chloro-7-(2-propen-1-yl)-3-(2,2,2-trifluoroethyl)-3,7-dihydro-1H-purine-2,6-dione (0.070 g, 0.23 mmol) in anhydrous DMF (2 ml) was added caesium carbonate (0.085 g, 0.26 mmol) followed by 1-iodoethane (0.061 g, 0.39 mmol). The mixture was heated for 5 h at 80° C. then stirred for 16 h at ambient temperature under an atmosphere of nitrogen. The solvent was removed under reduced pressure using a vacuum centrifuge and the residue dissolved in anhydrous THF (2.5 ml). To the mixture was added palladium tetrakis (0.030 g, 0.026 mmol) and morpholine (0.040 g, 0.45 mmol) and the reaction mixture degassed using nitrogen then stirred at ambient temperature for 72 h. The mixture was partitioned between chloroform and 2N HCl aq., and the aqueous layer re-extracted. Organic extracts were combined and evaporated under a stream of nitrogen then purified using aminopropyl SPE (eluting with acetic acid:methanol:DCM, 1:2:2) to give the title compound as a white solid in >95% purity (0.041 g, 60%). NMR $\delta_H$ (400 MHz, d$^4$-MeOD) 1.20 (t, 3H, J=7 Hz), 4.03 (q, 2H, J=7 Hz), 4.73 (q, 2H, J=8.5 Hz), m/z 297 [MH$^+$].

Example 26

8-chloro-1-propyl-3-(2,2,2-trifluoroethyl)-3,7-dihydro-1H-Purine-2,6-dione

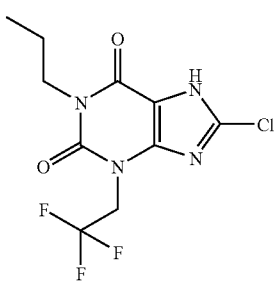

Prepared in similar fashion to Example 25 using propyl iodide to alkylate on N1.

NMR $\delta_H$ (400 MHz, CDCl$_3$) 0.99 (t, 3H, J=7.5 Hz), 1.68-1.79 (m, 2H), 4.07 (t, 2H, J=7.5 Hz), 4.77 (q, 2H, J=8.5 Hz), NH not observed to $\delta_H$ 13; m/z 311 [MH$^+$].

Example 27

8-chloro-1-(4,4,4-trifluorobutyl)-3-(2,2,2-trifluoroethyl)-3,7-dihydro-1H-purine-2,6-dione

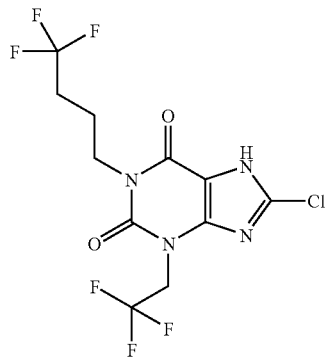

Prepared in similar fashion to Example 25 using 4-bromo-1,1,1-trifluorobutane to alkylate on N1.

NMR; $\delta_H$ (400 MHz, d$^4$-MeOD) 1.83-1.95 (m, 2H), 2.14-2.32 (m, 2H), 4.06 (t, 2H, J=7 Hz), 4.74 (q, 2H, J=8.5 Hz), m/z 377 [M−H]$^−$.

Example 28

8-Bromo-1-methyl-3-pentyl-3,7-dihydro-1H-purine-2,6-dione

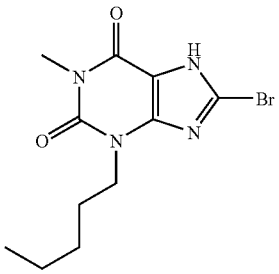

a)
1-methyl-3-pentyl-3,7-dihydro-1H-purine-2,6-dione

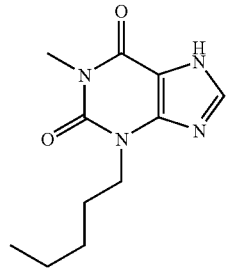

1-methyl-3-pentyl-7-(2-propen-1-yl)-3,7-dihydro-1H-purine-2,6-dione (0.45 g, 1.63 mmol), phenylsilane (0.25 ml, 2.03 mmol) and tetrakis(triphenylphosphine)palladium(0)

(0.35 g, 0.3 mmol) was dissolved in DCM (10 ml) containing acetic acid (6 ml). The air in the flask was replaced by nitrogen by evacuating the flask then filling with nitrogen (x3) and the reaction mixture heated to 45 C for 4 h. The solution was allowed to cool diluted with DCM then washed with water then saturated sodium bicarbonate solution. The organics were isolated, dried and concentrated to yield crude product. Purification by SPE (silica) eluting with ether provided the product, 0.06 g, 16%. m/z 237 [MH+].

b) 8-Bromo-1-methyl-3-pentyl-3,7-dihydro-1H-purine-2,6-dione

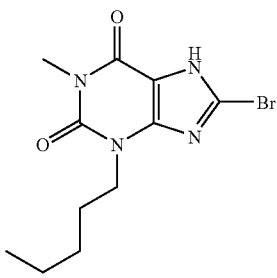

1-methyl-3-pentyl-3,7-dihydro-1H-purine-2,6-dione (0.06 g, 0.25 mmol) was dissolved in DMF (2 ml) and N-bromosuccinamide (0.045 g, 0.25 mmol) added. The mixture was stirred for 18 h, concentrated and the crude purified by eluting through an aminopropyl SPE (5 g) with first methanol then 5% acetic acid/methanol to elute product. The product was further purified by mass directed auto prep to yield the title compound as a white solid (0.01 g, 12%). NMR $\delta_H$ (400 MHz, d$^6$-DMSO) 0.86 (t, 3H, J=7 Hz), 1.21-1.35 (m, 4H), 1.59-1.68 (m, 2H), 3.22 (s, 3H), 3.91 (t, 2H, J=7.5 Hz), 14.39 (br. s, 1H); m/z 315, 317 [MH+].

Example 29

8-chloro-1-methyl-3-pentyl-3,7-dihydro-1H-urine-2,6-dione

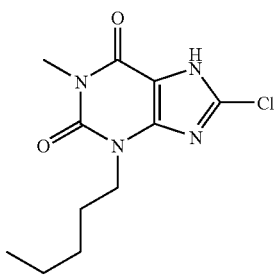

a) 8-chloro-1-methyl-3-pentyl-7-(2-propen-1-yl)-3,7-dihydro-1H-purine-2,6-dione

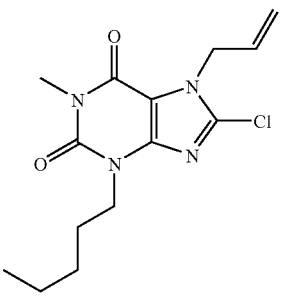

To a solution of 8-chloro-3-pentyl-7-(2-propen-1-yl)-3,7-dihydro-1H-purine-2,6-dione (3.9 g, 13.3 mmol) in DMF (35 ml) was added cesium carbonate and the mixture stirred for 10 min whereupon iodomethane (0.91 ml, 14.6 mmol) was added and the mixture stirred for 18 h. The reaction was partitioned between ethyl acetate and 2N HCl solution and the organics isolated, dried (MgSO$_4$) and concentrated. Chromatography on silica SPE eluting with cyclohexane/ethyl acetate (5%-20%) provided the product as an oil, 2.78 g, 68%. m/z 311[MH+].

b) 8-chloro-1-methyl-3-pentyl-3,7-dihydro-1H-purine-2,6-dione

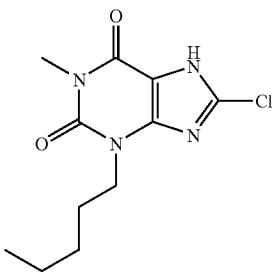

Tetrakis(triphenylphosphine)palladium (1.0, 0.90 mmol) was placed in a flask which was evacuated and then filled with nitrogen (x3). A solution of 8-chloro-1-methyl-3-pentyl-7-(2-propen-1-yl)-3,7-dihydro-1H-purine-2,6-dione (2.78 g, 8.96 mmol) in 50 ml of THF was added and the flask evacuated once more and nitrogen introduced. DMSO (4.5 ml) and morpholine (7.8 ml, 89.6 mmol) was added and the solution stirred for 5 h. The solution was partitioned between ethyl acetate and 2N HCl solution and the organic fraction washed with brine, dried (MgSO$_4$) and concentrated. The crude was purified with an aminopropyl SPE eluting with first methanol then methanol containing 0-15% acetic acid to provide the title compound as a white solid, 1.12 g, 46%. NMR $\delta_H$ (400 MHz, d$^6$-DMSO) 0.86 (t, 3H, J=7 Hz), 1.21-1.35 (m, 4H), 1.59-1.68 (m, 2H), 3.22 (s, 3H), 3.91 (t, 2H, J=7.5 Hz), NH not observed; m/z 271 [MH+].

Example 30

3-butyl-8-chloro-1-methyl-3,7-dihydro-1H-purine-2,6-dione

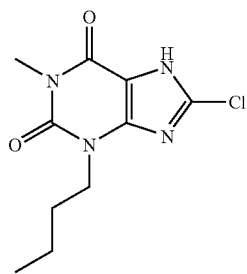

Prepared in similar fashion to Example 29 using 3-butyl-8-chloro-7-(2-propen-1-yl)-3,7-dihydro-1H-purine-2,6-dione as the starting material.

NMR $\delta_H$ (400 MHz, d⁶-DMSO) 0.88 (t, 3H, J=7 Hz), 1.25-1.35 (m, 2H), 1.6-1.66 (m, 2H), 3.22 (s, 3H), 3.91 (t, 2H, J=7.5 Hz), 14.46 (br s, 1H); m/z 257 [MH⁺].

Example 31

4-(8-chloro-1-methyl-2,6-dioxo-1,2,6,7-tetrahydro-3H-purin-3-yl)butanenitrile

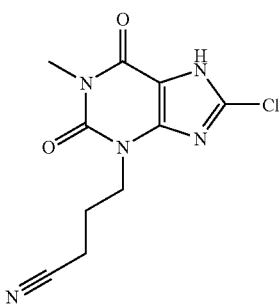

To a mixture of 8-chloro-1-methyl-7-(2-propen-1-yl)-3,7-dihydro-1H-purine-2,6-dione (70 mg, 0.292 mmol) and Na₂CO₃ (37 mg, 0.35 mmol) in DMF (3 ml) was added 4-bromobutyronitrile (0.035 ml, 0.35 mmol). The mixture was stirred at room temperature overnight, before degassing under a gentle vacuum and introducing nitrogen. Pd(PPh₃)₄ (50 mg, 0.044 mmol) and morpholine (0.254 ml, 2.92 mmol) was then added sequentially. After two hours stirring at room temperature further fresh Pd(PPh₃)₄ (50 mg, 0.044 mmol) was added and stirring continued overnight. The reaction mixture was partioned between ethyl acetate (20 ml) and water (20 ml) adding a small amount of 2M HCl to aid separation. The organic layer was separated, washed with brine, dried (MgSO₄) and concentrated. The residue was taken up in MeOH and passed down an amino-propyl SPE (5 g), eluting with MeOH followed by 3-5% AcOH/MeOH. The product fraction was concentrated to afford the title compound 39.7 mg (51%); NMR; $\delta_H$ (400 MHz, d⁶-DMSO) 1.91-2.00 (m, 2H), 2.55 (t, 2H, J=7 Hz), 3.22 (s, 3H), 4.03 (t, 2H, J=7 Hz), 14.49 (br.s, 1H); m/z 268.1 [MH⁺].

Example 32

8-chloro-1-methyl-3-(4,4,4-trifluorobutyl)-3,7-dihydro-1H-purine-2,6-dione

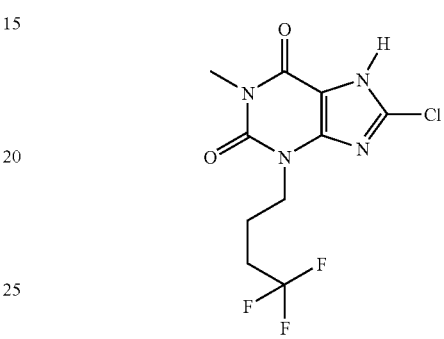

A solution of 8-chloro-1-methyl-7-(2-propen-1-yl)-3,7-dihydro-1H-purine-2,6-dione (0.048 g, 0.2 mmol) in THF (1 ml) was treated with caesium carbonate (0.78 g, 0.24 mmol) and 4-bromo-1,1,1-trifluorobutane (0.044 g, 0.25 mmol). The mixture was stirred at ambient temperature for 1 hour then heated at 50° C. for 4 hours and then cooled. The mixture was degassed by alternately applying vacuum and nitrogen pressure to the mixture and then treated with morpholine (0.17 ml, 2 mmol) and tetrakis(triphenylphosphine)palladium(0) (0.023 g, 0.02 mmol). After 2 hours the mixture was treated cautiously with 2M aqueous hydrochloric acid (2 ml) and the product extracted with chloroform (2×4 ml). The combined organics were evaporated and the product purified by reverse-phase mass directed HPLC to afford the title compound 6.2 mg (10%); NMR; $\delta_H$ (400 MHz, d⁶-DMSO); 1.84-1.92 (m, 2H), 2.28-2.35 (m, 2H), 3.22 (s, 3H), 3.99-4.03 (m, 2H) 14.31 (br.s, 1H); m/z 311.2[MH⁺].

Example 33

3-butyl-8-chloro-1-ethyl-3,7-dihydro-1H-purine-2,6-dione

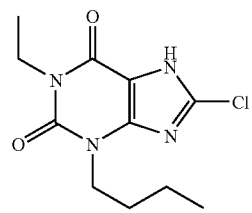

a) 3-butyl-7-(phenylmethyl)-3,7-dihydro-1H-purine-2,6-dione

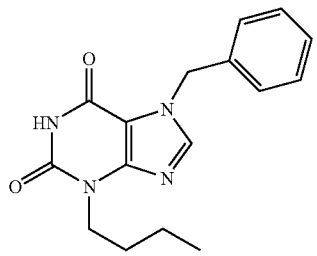

7-benzyl-3,7-dihydro-1H-purine-2,6-dione (17.14 g, 70.8 mmol) [Synthetic Communications, 20(16), 2459-2467, 1990] and potassium carbonate (11.43 g, 82.8 mmol) were suspended in DMF (400 mL) at 40° C. After stirring for thirty minutes, butyl iodide (8.76 mL, 77.0 mmol) was added, and the mixture was stirred at 40° C. overnight. 50% Aqueous acetic acid (60 mL) was added, and the solution was concentrated under reduced pressure. The residue was suspended in water (500 mL), and the products were extracted into chloroform. The organics were collected, concentrated, and product was isolated using flash chromatography eluting with 1% methanol in dichloromethane to provide the product (9.49 g, 45%); $^1$H NMR (400 MHz; CDCl$_3$) δ: 0.95 (3H, t), 1.34-1.41 (2H, m), 1.70-1.78 (2H, m), 4.05 (2H, t), 5.46 (2H, s), 7.31-7.40 (5H, m), 7.56 (1H, s), 8.21 (1H, br.s); m/z 299[MH$^+$].

b) 3-butyl-1-ethyl-7-(phenylmethyl)-3,7-dihydro-1H-purine-2,6-dione

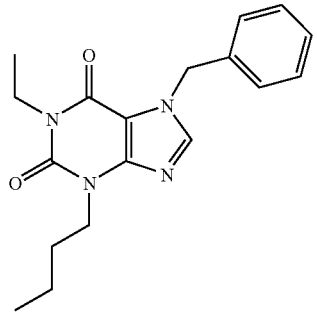

3-butyl-7-(phenylmethyl)-3,7-dihydro-1H-purine-2,6-dione (0.429 g, 1.24 mmol) and potassium carbonate (0.256 g, 1.85 mmol) were suspended in DMF (8 mL), iodoethane (0.113 mL, 1.42 mmol) was added. The reaction mixture was stirred at ambient temperature overnight. The reaction mixture was evaporated to dryness and the residue was partitioned between water and ethyl acetate. The organic layer was washed with water, followed by brine, dried over anhydrous sodium sulphate and concentrated under reduced pressure to yield the title compound; $^1$H NMR (400 MHz; CDCl$_3$) δ: 0.96 (3H, t), 1.25 (3H, t), 1.36-1.45 (2H, m), 1.72-1.76 (2H, m), 4.05-4.13 (4H, m), 5.50 (2H, s), 7.32-7.40 (5H, m), 7.52 (1H, s); m/z 327[MH$^+$].

c) 3-Butyl-1-ethyl-3,7-dihydro-1H-purine-2,6-dione

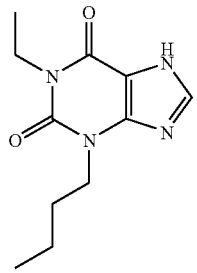

3-butyl-1-ethyl-7-(phenylmethyl)-3,7-dihydro-1H-purine-2,6-dione (0.353 g, 1.08 mmol) was dissolved in acetic acid (30 mL), 20% palladium hydroxide on carbon (0.238 g) was added, and the mixture was shaken under hydrogen (at 50 psi) overnight. The catalyst was removed by filtration through Celite® and washed with acetic acid. The filtrate was concentrated under reduced pressure to yield the title compound (0.227g, 89%); $^1$H NMR (400 MHz; CDCl$_3$) δ: 0.97 (3H, t), 1.28 (3H, t), 1.38-1.47 (2H, m), 1.74-1.82 (2H, m), 4.12-4.17 (4H, m), 7.80 (1H, s); m/z 237[MH$^+$].

d) 3-Butyl-8-chloro-1-ethyl-3,7-dihydro-1H-purine-2,6-dione

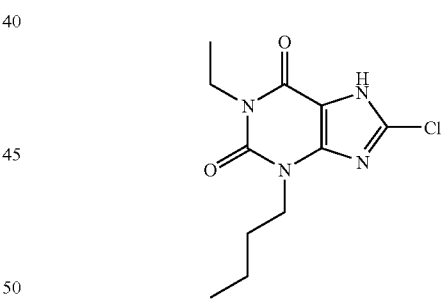

3-Butyl-1-ethyl-3,7-dihydro-1H-purine-2,6-dione (100 mg, 0.42 mmol) and NCS (56 mg, 0.42 mmol) were suspended in MeCN (5 mL) and heated at 120° C. under microwave irradiation. The reaction mixture was concentrated under reduced pressure and the title compound isolated using HPLC. [HPLC conditions used for the purification: 23 minute run time. Solvents: 0.1% TFA in MeCN and 0.1% TFA in water. MeCN increased from 5% to 95% linearly over 15 minutes. Held at 95% for 2 min. Then decreased to 5% linearly over 1 min., equilibrated at 5% for 5 minutes before next injection.]; $^1$H NMR (400 MHz; CDCl$_3$) δ: 0.97 (3H, t), 1.31 (3H, t), 1.38-1.45 (2H, m), 1.72-1.80 (2H, m), 4.09-4.20 (4H, m), 13.40 (1H, br.s); m/z 271 [MH$^+$].

Example 34

8-Chloro-3-(4-methylpentyl)-3,7-dihydro-1H-purine-2,6-dione

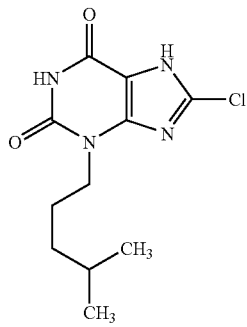

From 1-bromo-4-methylpentane (81 mg)
Recrystallised from MeOH
Yield 34.8 mg (29%), NMR; (400 MHz, d$^6$-DMSO) δ$_H$ 0.83 (d, 6H, J=8 Hz), 1.12-1.22 (m, 2H), 1.55 (septet, 1H, J=8 Hz), 1.58-1.68 (m, 2H), 3.83 (t, 2H, J=7.5 Hz), 11.20 (s, 1H); m/z 271 [MH$^+$]

Example 35

6-(8-Chloro-2,6-dioxo-1,2,6,7-tetrahydro-3H-purin-3-yl)-2,2-dimethylhexanenitrile

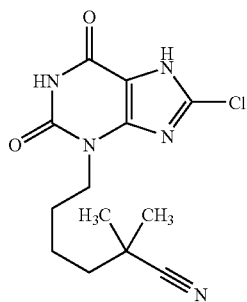

From 6-bromo-2,2-dimethylhexanenitrile (100 mg)
Recrystallised from MeOH.
Yield 48.5 mg (35%); NMR; (400 MHz, d$^6$-DMSO) δ$_H$ 1.27 (s, 6H), 1.35-1.44 (m, 2H), 1.54-1.59 (m, 2H), 1.63-1.72 (m, 2H), 3.88 (t, 2H, J=7 Hz), 11.24 (s, 1H); m/z 310 [MH$^+$]

Example 36

8-chloro-3-(6-methylheptyl)-3,7-dihydro-1H-purine-2,6-dione

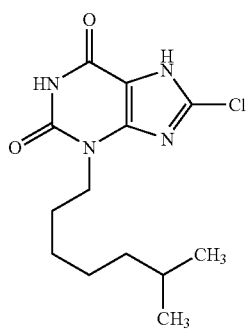

From 1-bromo-6-methylheptane (95 mg)
Recrystallised from MeOH.
Yield 36 mg (27%), NMR; (400 MHz, d$^6$-DMSO) δ$_H$ 0.83 (d, 6H, J=7.5 Hz), 1.10-1.17 (m, 2H), 1.20-1.34 (m, 4H), 1.48 (septet, 1H, J=7.5 Hz), 1.58-1.68 (m, 2H), 3.84 (t, 2H, J=8 Hz), 11.22 (s, 1H); m/z 299 [MH$^+$]

Example 37

8-Chloro-3-octyl-3,7-dihydro-1H-purine-2,6-dione

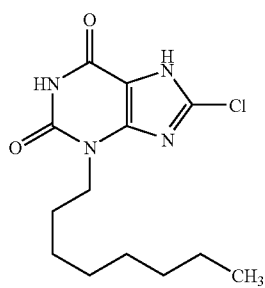

8-Chloro-3,7-dihydro-1H-purine-2,6-dione (100 mg, 0.44 mmol) was stirred with sodium carbonate (52 mg, 0.49 mmol) in dry DMF (3 ml) for 20 min., then 1-iodooctane (118 mg, 0.49 mmol) was added and the mixture was stirred under nitrogen at 40 C for 65 h. After cooling to room temperature, the mixture was thoroughly degassed by evacuating the vessel and refilling with nitrogen several times. Tetrakis(triphenylphosphine)palladium(0) (102 mg, 0.09 mmol) was added, the mixture degassed again and then morpholine (0.385 ml, 4.4 mmol) added and stirring continued for 6.5 h. 2M HCl and EtOAc were added, and the 2-phase system was filtered. The product was present predominantly in the filtered solid, which was recrystallised from THF-acetonitrile, followed by MeOH, with filtration, to afford the pure title compound.

Yield 48 mg (36%); NMR; (400 MHz, d$^6$-DMSO) δ$_H$ 0.84 (t, 3H, J=7 Hz), 1.18-1.30 (m, 10H), 1.57-1.66 (m, 2H), 3.84 (t, 2H, J=7.5 Hz), 11.22 (s, 1H); m/z 299 [MH$^+$]

Example 38

8-Chloro-3-decyl-3,7-dihydro-1H-purine-2,6-dione

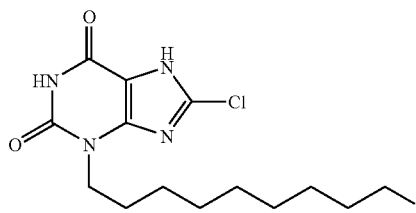

Prepared by the method of Example 37, starting from 1-bromodecane (108 mg). Further purification was achieved by recrystallisation from MeOH followed by mass-directed autoprep.

Yield 2 mg (1.4%); NMR; (400 MHz, $d^4$-methanol) $\delta_H$ 0.89 (t, 3H, J=7 Hz), 1.26-1.38 (m, 14H), 1.68-1.76 (m, 2H), 3.97 (t, 2H, J=7.5 Hz); m/z 327 [MH$^+$].

Example 39

8-Chloro-3-(cyclohexylmethyl)-3,7-dihydro-1H-purine-2,6-dione

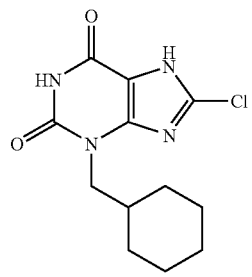

Prepared in a similar manner to Example 37, from (bromomethyl)cyclohexane (87 mg) except that an additional heating period at 80 C for 18 h was performed.

Recrystallised from MeOH.

Yield 31 mg (25%); NMR; (400 MHz, $d^6$-DMSO) $\delta_H$ 0.90-1.02 (m, 2H), 1.08-1.20 (m, 3H), 1.53-1.69 (m, 5H), 1.77-1.87 (m, 1H), 3.70 (d, 2H, J=7.5 Hz), 11.21 (s, 1H); m/z 283 [MH$^+$]

General Method for Examples 40-46

To 8-chloro-3,7-dihydro-1H-purine-2,6-dione (100 mg, 0.442 mmol) in dry THF (3 ml) was added the alcohol (0.442 mmol). The mixture was stirred at 0 C as a solution of dibenzyl azodicarboxylate (280 mg of 94% purity, 0.88 mmol) in dry THF (2 ml) was added, followed by a solution of triphenylphosphine (232 mg, 0.88 mmol) in dry THF, added portionwise over 5 min. After a further 30 min at 0 C, stirring was continued at room temperature for 18 h. The mixture was thoroughly degassed by evacuating and refilling the vessel with nitrogen several times, then tetrakis(triphenylphosphine)palladium(0) (102 mg, 0.088 mmol) was added followed by morpholine (0.385 ml, 4.42 mmol) and stirring was continued for 4.5 h. EtOAc and 2M HCl were added, and the mixture filtered to remove a yellow precipitated solid. The filtrate was separated and the organic phase concentrated and redissolved in a mixture of THF and MeOH. This solution was passed down an aminopropyl SPE, eluting with THF-MeOH (1:1) followed by MeOH and then 5% AcOH in DCM-MeOH (1:1). The product fractions thus obtained were concentrated and recrystallised from MeOH to afford the pure title compound.

Example 40

(+/−)-8-Chloro-3-(3-methylpentyl)-3,7-dihydro-1H-purine-2,6-dione

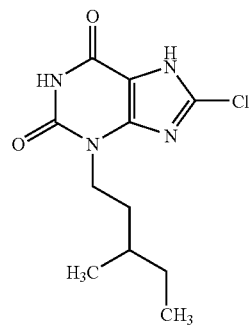

From (+/−)-3-methyl-1-pentanol 45 mg
Yield 20.2 mg (17%); NMR; (400 MHz, $d^6$-DMSO) $\delta_H$ 0.83 (t, 3H, J=7.5 Hz), 0.90 (d, 3H, J=6.5 Hz), 1.12-1.21 (m, 1H), 1.30-1.48 (m, 3H), 1.58-1.68 (m, 1H), 3.87 (t, 2H, J=7.5 Hz), 11.21 (s, 1H); m/z 271 [MH$^+$].

Example 41

8-Chloro-3-(2-cyclopentylethyl)-3,7-dihydro-1H-purine-2,6-dione

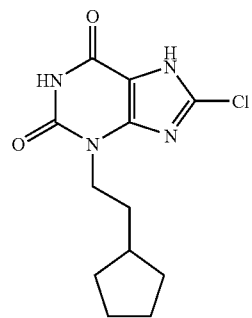

From 2-cyclopentylethanol 50 mg
Yield 24.6 mg (20%); NMR; (400 MHz, $d^6$-DMSO) $\delta_H$ 1.04-1.15 (m, 2H), 1.40-1.67 (m, 6H), 1.70-1.82 (m, 3H), 3.86 (t, 2H, J=7.5 Hz), 11.22 (s, 1H); m/z 283 [MH$^+$]

Example 42

8-Chloro-3-(cyclopropylmethyl)-3,7-dihydro-1H-purine-2,6-dione

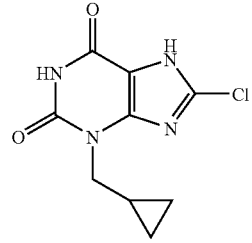

From cyclopropylmethanol 32 mg

Yield 22.3 mg (21%); NMR; (400 MHz, d⁶-DMSO) $\delta_H$ 0.34-0.40 (m, 2H), 0.40-0.48 (m, 2H), 1.17-1.27 (m, 1H), 3.74 (d, 2H, J=7.5 Hz), 11.23 (s, 1H); m/z241 [MH⁺].

Example 43

(+/−)-8-Chloro-3-(2-methylbutyl)-3,7-dihydro-1H-purine-2,6-dione

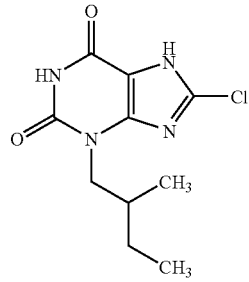

From (+/−)-2-methyl-1-butanol 39 mg

Yield 12 mg (9.5%); NMR; (400 MHz, d⁶-DMSO) $\delta_H$ 0.81 (d, 3H, J=7 Hz), 0.86 (t, 3H, J=7.5 Hz), 1.06-1.17 (m, 1H), 1.30-1.41 (m, 1H), 1.90-2.00 (m, 1H), 3.68 (dd, 1H, J=13.5 and 8 Hz), 3.75 (dd, 1H, J=13.5 and 7.5 Hz), 11.22 (s, 1H); m/z 257 [MH⁺]

Example 44

(+/−)-8-Chloro-3-(2-methylpentyl)-3,7-dihydro-1H-purine-2,6-dione

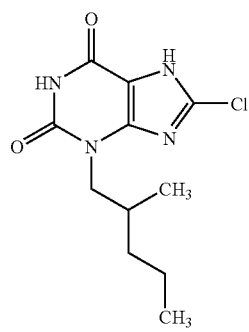

From (+/−)-2-methyl-1-pentanol 45 mg

Yield 22.4 mg (19%); NMR; (400 MHz, d⁶-DMSO) $\delta_H$ 0.81 (d, 3H, J=7 Hz), 0.84 (t, 3H, J=7.5 Hz), 1.05-1.16 (m, 1H), 1.16-1.43 (m, 3H), 1.98-2.09 (m, 1H), 3.67 (dd, 1H, J=13.5 and 8 Hz), 3.74 (dd, 1H, J=13.5 and 7 Hz), 11.22 (s, 1H); m/z 271 [MH⁺]

Example 45

8-Chloro-3-(cyclobutylmethyl)-3,7-dihydro-1H-purine-2,6-dione

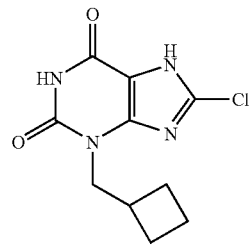

From cyclobutylmethanol 38 mg

Yield 30.5 mg (27%); NMR; (400 MHz, d⁶-DMSO) $\delta_H$ 1.73-1.85 (m, 4H), 1.86-1.97 (m, 2H), 2.66-2.79 (m, 1H), 3.90 (d, 2H, J=7.5 Hz), 11.22 (s, 1H); m/z 255 [MH⁺]

Example 46

8-chloro-3-(cyclopentylmethyl)-3,7-dihydro-1H-purine-2,6-dione

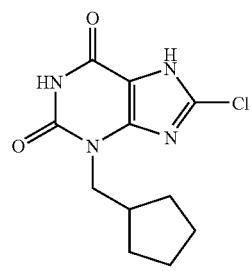

From cyclopentylmethanol 44 mg

Yield 15 mg (13%); NMR; (400 MHz, d⁶-DMSO) $\delta_H$ 1.20-1.32 (m, 2H), 1.42-1.54 (m, 2H), 1.54-1.66 (m, 4H), 2.32-2.45 (m, 1H), 3.79 (d, 2H, J=8 Hz), 11.22 (s, 1H); m/z 269 [MH⁺]

Example 47

8-chloro-3-(3-cyclopropylpropyl)-3,7-dihydro-1H-purine-2,6-dione

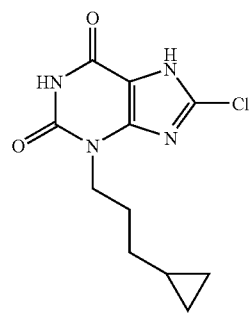

From 3-cyclopropyl-1-propanol (P. J. Wagner, J. Amer. Chem. Soc., 1981, 103, 3837-3841) (44 mg).

Yield 27.7 mg (23%); NMR; (400 MHz, d⁶-DMSO) $\delta_H$ −0.03-+0.03 (m, 2H), 0.34-0.40 (m, 2H), 0.65-0.75 (m, 1H), 1.15-1.23 (m, 2H),1.66-1.76 (m, 2H), 3.87 (t, 2H, J=7 Hz), 11.15 (s, 1H); m/z 269 [MH⁺]

Example 48

8-chloro-3-(2-cyclobutylethyl)-3,7-dihydro-1H-purine-2,6-dione

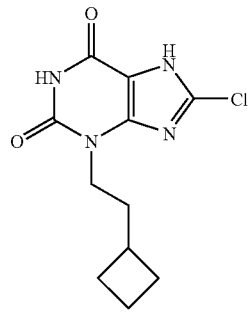

From 2-cyclobutylethanol (P. Vergnon, Eur. J. Med. Chem., 1975, 10, 65-71) (44 mg).

Yield 21.5 mg (18%); NMR; (400 MHz, d⁶-DMSO) $\delta_H$ 1.53-1.64 (m, 2H), 1.68-1.85 (m, 4H), 1.93-2.03 (m, 2H), 2.19-2.30 (m, 1H), 3.78 (t, 2H, J=7 Hz), 11.20 (s,1H); m/z 269 [MH⁺]

Example 49

8-chloro-3-(4-fluorobutyl)-3,7-dihydro-1H-purine-2,6-dione

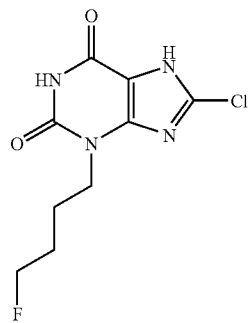

a) 8-chloro-3-(4-fluorobutyl)-7-(2-propen-1-yl)-3,7-dihydro-1H-purine-2,6-dione

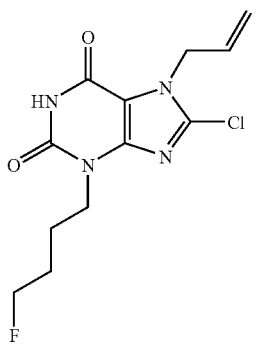

To a solution of 8-chloro-7-(2-propen-1-yl)-3,7-dihydro-1H-purine-2,6-dione (200 mg, 0.88 mmol, 1eq) in anhydrous DMSO (1 ml) in a 1.5 ml microwave vial equipped with a stirrer was added sodium bicarbonate (113 mg, 1.07 mmol, 1.2eq) followed by 1-bromo-4-fluorobutane (114 ul, 165 mg, 1.06 mmol, 1.2eq). The vial was sealed and heated with stirring using a microwave, maintaining the temperature at 120° C. for 25 min with a maximum power output of 300 W. The resulting dark brown solution was diluted with methanol (1 ml) and purified by mass directed autopreparative HPLC to give the title compound as a white solid (159 mg, 60%). m/z 301.3[MH⁺]

8-chloro-3-(4-fluorobutyl)-3,7-dihydro-1H-purine-2,6-dione

To a suspension of 8-chloro-3-(4-fluorobutyl)-7-(2-propen-1-yl)-3,7-dihydro-1H-purine-2,6-dione (100 mg, 0.33 mmol, 1eq) in anhydrous DCM (2 ml) was added palladium tetrakis (38 mg, 0.033 mmol, 10% bw), followed by acetic acid (115 ul, 121 mg, 2.01 mmol, 6eq) and phenyl silane (410 ul, 360 mg, 3.33 mmol, 10eq). The resulting light yellow solution was stirred at ambient temperature for 16 h to give a dark purple solution. The solvent was removed under a stream of nitrogen and the residue dissolved in a DMSO/methanol solution (3 ml, 2:1) with heating. The gelatinous mixture was allowed to cool to ambient temperature, filtered then purified by mass directed autopreparative HPLC to give the title compound as a white solid (35 mg, 43%). m/z 261.2[MH⁺] NMR (400 MHz, MeOD), $\delta_H$ 4.45 (2H, dt, J=47 and 6 Hz), 4.03 (2H, t, J=7 Hz), 1.90-1.65 (4H, m).

The following compounds were prepared in similar fashion and purified by preparative or mass directed autopreparative HPLC as appropriate:

Example 50
8-chloro-3-(3-fluoropropyl)-3,7-dihydro-1H-purine-2,6-dione

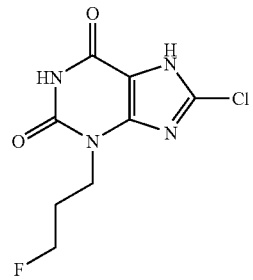

NMR (400 MHz, MeOD), $\delta_H$ 4.51 (2H, dt, J=47 and 6 Hz), 4.11 (2H, t, J=7 Hz), 2.18-2.03 (2H, m). m/z 247 [MH⁺]

Example 51

8-chloro-3-(5-fluoropentyl)-3,7-dihydro-1H-purine-2,6-dione

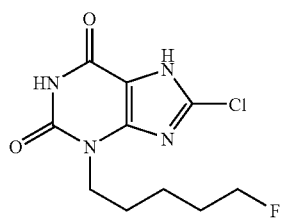

NMR (400 MHz, MeOD), $\delta_H$ 4.41 (2H, dt, J=48 and 6 Hz), 3.99 (2H, t, J=8 Hz), 1.84-1.63 (4H, m), 1.52-1.40 (2H, m). m/z 273.29 [MH⁻]

Example 52

3-(3-buten-1-yl)-8-chloro-3,7-dihydro-1H-purine-2,6-dione

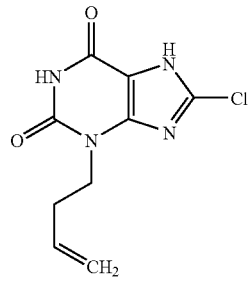

8-chloro-3,7-dihydro-1H-purine-2,6-dione (100 mg, 0.44 mmol) was stirred with sodium carbonate (52 mg, 0.49 mmol) in dry DMF (3 ml) for 45 min., then 4-bromo-1-butene (66 mg, 0.49 mmol) was added and the mixture was stirred under nitrogen at 40 C for 65 h. After cooling to room temperature, the mixture was thoroughly degassed by evacuating the vessel and refilling with nitrogen several times. Tetrakis(triphenylphosphine)palladium(0) (102 mg, 0.09 mmol) was added, the mixture degassed again and then morpholine (0.385 ml, 4.4 mmol) added and stirring continued for 6.5 h. 2M HCl and EtOAc were added, and the 2-phase system was filtered to remove a yellow precipitated solid. The organic phase of the filtrate was separated and evaporated. The residue was dissolved with warming in THF-MeOH (1:1) and loaded onto an aminopropyl SPE (5 g) which was eluted with THF-MeOH (1:1) followed by MeOH and then 5% AcOH in MeOH-DCM (1:1). The product fraction was further purified by mass-directed autoprep to afford the title compound.

Yield 27.5 mg (26%), NMR; (400 MHz, d⁶-DMSO) $\delta_H$ 2.40 (dt, 2H, J=7 and 6 Hz), 3.93 (t, 2H, J=7 Hz), 4.97-5.07 (m, 2H), 5.74-5.85 (m, 1H), 11.22 (s, 1H); m/z 241 [MH⁺]

Example 53

8-chloro-3-(6-fluorohexyl)-3,7-dihydro-1H-purine-2,6-dione

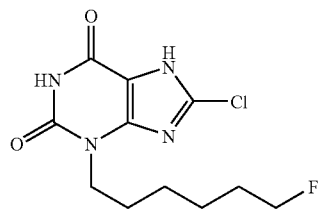

NMR (400 MHz, MeOD), $\delta_H$ 4.40 (2H, dt, 48 and 6 Hz), 3.98 (2H, t, 8 Hz), 1.80-1.60 (4H, m), 1.52-1.35 (4H, m). m/z 287 [MH⁻]

Example 54

8-chloro-3-ethyl-1-methyl-3,7-dihydro-1H-purine-2,6-dione

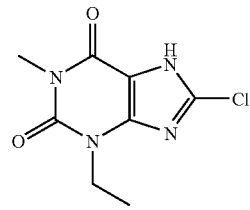

a) 8-chloro-3-({[2-(methyloxy)ethyl]oxy}methyl)-7-(2-propen-1-yl)-3,7-dihydro-1H-purine-2,6-dione

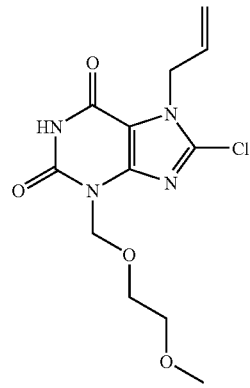

To a solution of 8-chloro-7-(2-propen-1-yl)-3,7-dihydro-1H-purine-2,6-dione (6 g, 26.5 mmol) in anhydrous DMF (30 ml) was added sodium carbonate (3.09 g, 29.15 mmol). After 10 minutes stirring at room temperature methoxyethoxymethylchloride (3.03 ml, 26.5 mmol) was added and stirring continued under nitrogen at room temperature for 66 hours. The reaction mixture was concentrated in vacuo and the residue dissolved in EtOAc (100 ml) and washed with brine (100 ml), the aqueous extract was extracted with DCM (100 ml) and the organic extracts dried (MgSO₄) combined and concentrated in vacuo. The residue was triturated with EtOAc and the solid filtered off. Concentration of the filtrate afforded a light brown oil that was absorbed onto silica and purified by SPE (Si, 50 g) eluting with a gradient of 1:1 EtOAc/cyclohexane-EtOAc to afford the title compound as a white solid (2 g, 24%). m/z 315.2[MH⁺]

b) 8-chloro-1-methyl-3-({[2-(methyloxy)ethyl]oxy}methyl)-7-(2-propen-1-yl)-3,7-dihydro-1H-purine-2,6-dione

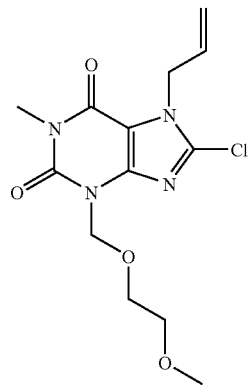

To a solution of 8-chloro-3-({[2-(methyloxy)ethyl]oxy}methyl)-7-(2-propen-1-yl)-3,7-dihydro-1H-purine-2,6-dione (2 g, 6.37 mmol) in anhydrous DMF (15 ml) was added sodium carbonate (0.743 g, 7 mmol). After 10 minutes stirring at room temperature methyliodide (0.44 ml, 7 mmol) was added and stirring continued under nitrogen at room temperature for 18 hours. The reaction mixture was concentrated in vacuo and the residue dissolved in EtOAc (100 ml) and washed with brine (100 ml). The organic extract was dried (MgSO$_4$) filtered and evaporated to afford the title compound as a tan oil (85% pure) (2.98 g, quant.), m/z 329.2[MH$^+$]

c) 8-chloro-1-methyl-7-(2-propen-1-yl)-3,7-dihydro-1H-purine-2,6-dione

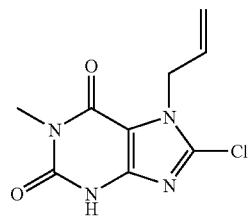

To a solution of 8-chloro-1-methyl-3-({[2-(methyloxy)ethyl]oxy}methyl)-7-(2-propen-1-yl)-3,7-dihydro-1H-purine-2,6-dione (2.9 g, 6.37 mmol) in dioxan (20 ml) and water (20 ml) was added 5M HCl aq. (20 ml). The resulting mixture was heated at 100° C. under nitrogen for 18 hours. The reaction mixture was then concentrated in vacuo, the residue was dissolved in EtOAc (100 ml) and washed with water. The organic extract was dried (MgSO$_4$) filtered and evaporated. Purification by SPE (Si, 20 g) eluting 2:3 EtOAc/cyclohexane afforded the title compound as a white solid (1.04 g, 68%). m/z 241.1[MH$^+$].

d) 8-chloro-3-ethyl-1-methyl-3,7-dihydro-1H-purine-2,6-dione

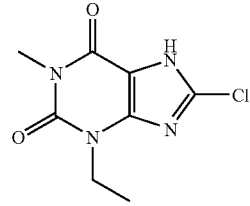

To a solution of 8-chloro-1-methyl-7-(2-propen-1-yl)-3,7-dihydro-1H-purine-2,6-dione (100 mg, 0.42 mmol) in anhydrous DMF (3 ml) was added sodium carbonate (58 mg, 0.54 mmol), after 10 minutes stirring ethyl iodide (0.043 ml, 0.54 mmol) was added and the reaction mixture stirred at room temperature under nitrogen for 90 hours. Pd(PPh$_3$)$_4$ (73 mg, 0.063 mmol) was then added and the reaction vessel evacuated and flushed with nitrogen (x3), morpholine (0.37 ml, 4.3 mmol) was added and stirring at room temperature under nitrogen continued for 4 hours. The reaction mixtue was diluted with EtOAc (25 ml) and washed with 2M HCl aq. (25 ml). The organic extract was dried (MgSO$_4$) filtered and evaporated. Purification by aminopropyl SPE (5 g) loading the compound and washing with MeOH before eluting the product with 5% AcOH/MeOH afforded the title compound as a white solid (67 mg, 70%). NMR; d$_H$ (400 MHz, d$^6$-DMSO) 1.20 (t, 3H, J=7 Hz), 3.22 (s, 3H), 3.97(q, 2H, J=7 Hz), 14.46 (1H, br s); m/z 227.2[M−H]$^−$.

All publications, including but not limited to patents and patent applications, cited in this specification are herein incorporated by reference as if each individual publication were specifically and individually indicated to be incorporated by reference herein as though fully set forth.

The invention claimed is:
1. A compound which is 8-chloro-3-pentyl-3,7-dihydro-1H-purine-2,6-dione:

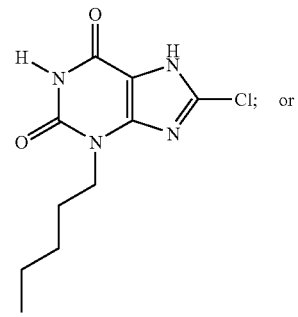

a pharmaceutically acceptable salt thereof.

2. A compound which is 8-chloro-3-pentyl-3,7-dihydro-1H-purine-2,6-dione.

3. A pharmaceutical formulation, which comprises a compound according to claim 1, and one or more physiologically acceptable diluents, excipients or carriers.

4. A method for treatment of coronary artery disease, which comprises administering a therapeutically effective amount of a compound of claim 1 to a human subject in need thereof.

5. A pharmaceutical formulation, which comprises a compound according to claim 2, and one or more physiologically acceptable diluents, excipients or carriers.

6. A method for treatment of atherosclerosis, which comprises administering a therapeutically effective amount of a compound of claim 1 to a human subject in need thereof.

7. A method for treatment of mixed dyslipidaemia, which comprises administering a therapeutically effective amount of a compound of claim 1 to a human subject in need thereof.

8. A method for treatment of diabetic dyslipidaemia, which comprises administering a therapeutically effective amount of a compound of claim 1 to a human subject in need thereof.

9. A method for treatment of hyperlipidaemia, which comprises administering a therapeutically effective amount of a compound of claim 1 to a human subject in need thereof.

10. A method for treatment of hyperlipoproteinaemia, which comprises administering a therapeutically effective amount of a compound of claim 1 to a human subject in need thereof.

11. A method for treatment of hypercholesteraemia, which comprises administering a therapeutically effective amount of a compound of claim 1 to a human subject in need thereof.

12. A method for treatment of hypertriglyceridaemia, which comprises administering a therapeutically effective amount of a compound of claim 1 to a human subject in need thereof.

13. A method for treatment of coronary artery disease, which comprises administering a therapeutically effective amount of a compound of claim 2 to a human subject in need thereof.

14. A method for treatment of atherosclerosis, which comprises administering a therapeutically effective amount of a compound of claim 2 to a human subject in need thereof.

15. A method for treatment of mixed dyslipidaemia, which comprises administering a therapeutically effective amount of a compound of claim 2 to a human subject in need thereof.

16. A method for treatment of diabetic dyslipidaemia, which comprises administering a therapeutically effective amount of a compound of claim 2 to a human subject in need thereof.

17. A method for treatment of hyperlipidaemia, which comprise administering a therapeutically effective amount of a compound of claim 2 to a human subject in need thereof.

18. A method for treatment of hyperlipoproteinaemia, which comprises administering a therapeutically effective amount of a compound of claim 2 to a human subject in need thereof.

19. A method for treatment of hypercholesteraemia, which comprises administering a therapeutically effective amount of a compound of claim 2 to a human subject in need thereof.

20. A method for treatment of hypertriglyceridaemia, which comprises administering a therapeutically effective amount of a compound of claim 2 to a human subject in need thereof.

* * * * *